US006927046B1

(12) United States Patent
Hanke et al.

(10) Patent No.: US 6,927,046 B1
(45) Date of Patent: Aug. 9, 2005

(54) INCREASED LYSINE PRODUCTION BY GENE AMPLIFICATION USING CORYNEFORM BACTERIA

(75) Inventors: Paul D. Hanke, Aurora, IL (US); Lhing-Yew Li-D'Elia, Savoy, IL (US); Holly J. Walsh, Roanoke, VA (US); Corey M. Crafton, Decatur, IL (US); P. John Rayapati, Decatur, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 19 days.

(21) Appl. No.: 09/722,441

(22) Filed: Nov. 28, 2000

Related U.S. Application Data

(60) Provisional application No. 60/184,130, filed on Feb. 22, 2000, and provisional application No. 60/173,707, filed on Dec. 30, 1999.

(51) Int. Cl.[7] .............................................. C12P 13/04
(52) U.S. Cl. ................. 435/106; 435/320.1; 435/252.3; 435/252.32; 435/254.11; 435/325; 435/419; 536/23.2; 536/23.7
(58) Field of Search .............................. 536/23.2, 23.7, 536/23.1; 435/106, 320.1, 252.3, 252.32, 254.11, 325, 419, 115

(56) References Cited

U.S. PATENT DOCUMENTS

| | | | |
|---|---|---|---|
| 2,979,439 A | 4/1961 | Kinoshita et al. | 195/47 |
| 3,565,951 A | 2/1971 | Ishida et al. | 260/527 |
| 3,687,810 A | 8/1972 | Kurihara et al. | 195/29 |
| 3,700,557 A | 10/1972 | Nakayama et al. | 195/29 |
| 3,707,441 A | 12/1972 | Shiio et al. | 195/29 |
| 3,708,395 A | 1/1973 | Nakayama et al. | 195/29 |
| 3,825,472 A | 7/1974 | Kubota et al. | 195/29 |
| 3,959,075 A | 5/1976 | Inuzuka et al. | 195/29 |
| 4,169,763 A | 10/1979 | Nakayama et al. | 435/115 |
| 4,346,170 A | 8/1982 | Sano et al. | 435/115 |
| 4,489,160 A | 12/1984 | Katsumata et al. | 435/253 |
| 4,500,640 A | 2/1985 | Katsumata et al. | 435/253 |
| 4,514,502 A | 4/1985 | Miwa et al. | 435/253 |
| 4,559,308 A | 12/1985 | Nutter et al. | 435/317 |
| 4,560,654 A | 12/1985 | Miwa et al. | 435/115 |
| 4,601,983 A | 7/1986 | Nakamori et al. | 435/115 |
| 4,617,267 A | 10/1986 | Katsumata et al. | 435/91 |
| 4,710,471 A | 12/1987 | Katsumata et al. | 435/253 |
| 4,757,009 A | 7/1988 | Sano et al. | 435/106 |
| 4,778,762 A | 10/1988 | Miwa et al. | 435/320 |
| 4,822,738 A | 4/1989 | Miwa et al. | 435/252.3 |
| 4,861,722 A | 8/1989 | Sano et al. | 435/252.32 |
| 4,954,441 A | 9/1990 | Katsumata et al. | 435/115 |
| 4,980,285 A | 12/1990 | Sano et al. | 435/108 |
| 5,034,318 A | 7/1991 | Miwa et al. | 435/108 |
| 5,034,319 A | 7/1991 | Azuma et al. | 435/114 |
| 5,158,891 A | 10/1992 | Takeda et al. | 435/320.1 |
| 5,236,831 A | 8/1993 | Katsumata et al. | 433/106 |
| 5,243,039 A | 9/1993 | Schendel et al. | 536/23.2 |
| 5,380,657 A | 1/1995 | Schaefer et al. | 435/172.3 |
| 5,426,050 A | 6/1995 | Morinaga et al. | 435/252.32 |
| 5,426,052 A | 6/1995 | Flickinger et al. | 536/23.2 |
| 5,498,532 A | 3/1996 | Katsumata et al. | 435/106 |
| 5,547,864 A | 8/1996 | Kawasaki et al. | 435/170 |
| 5,556,776 A | 9/1996 | Tsuchiya et al. | 435/106 |
| 5,591,577 A | 1/1997 | Tsuchiya et al. | 435/6 |
| 5,597,727 A | 1/1997 | Kohama et al. | 435/252.32 |
| 5,605,793 A | 2/1997 | Stemmer | 435/6 |
| 5,631,150 A | 5/1997 | Harkki et al. | 435/105 |
| 5,633,154 A | 5/1997 | Schaefer et al. | 435/172.3 |
| 5,640,803 A | 6/1997 | Kloepper et al. | 47/57.6 |

(Continued)

FOREIGN PATENT DOCUMENTS

| | | |
|---|---|---|
| EP | 0 733 710 A1 | 9/1996 |
| EP | 0 754 756 A1 | 1/1997 |
| EP | 0 811 682 A2 | 12/1997 |
| EP | 0 854 189 A2 | 7/1998 |
| EP | 1 108 790 A2 | 6/2001 |
| WO | WO 96/34961 | 11/1996 |
| WO | WO 00/63388 | 10/2000 |

OTHER PUBLICATIONS

Archer, J. and Sinskey, A.J., "The DNA sequence and minimal replicon of the *Corynebacterium glutamicum* plasmid pSR1: evidence of a common ancestry with plasmids from *C. diphtheriae*," *J. Gen. Microbiol.* 139:1753–1759, (1993).

(Continued)

*Primary Examiner*—P. Achutamuthy
*Assistant Examiner*—Kathleen Kerr
(74) *Attorney, Agent, or Firm*—Craig G. Cochenour; Duane A. Stewart III; Buchanan Ingersoll PC

(57) ABSTRACT

The invention provides methods to increase the production of an amino acid from Corynebacterium species by way of the amplification of amino acid biosynthetic pathway genes in a host cell chromosome. In a preferred embodiment, the invention provides methods to increase the production of L-lysine in *Corynebacterium glutamicum* by way of the amplification of L-lysine biosynthetic pathway genes in a host cell chromosome. The invention also provides novel processes for the production of an amino acid by way of the amplification of amino acid biosynthetic pathway genes in a host cell chromosome and/or by increasing promoter strength. In a preferred embodiment, the invention provides processes to increase the production of L-lysine in *Corynebacterium glutamicum* by way of the amplification of L-lysine biosynthetic pathway genes in a host cell chromosome. The invention also provides novel isolated nucleic acid molecules for L-lysine biosynthetic pathway genes of *Corynebacterium glutamicum* such as a naturally occurring, feedback-sensitive form of aspartokinase (ask) resulting from a threonine to isoleucine mutation at amino acid residue 380 in the ask gene of ATCC 21529, aspartate-semialdehyde dehydrogenase (asd), dihydrodipicolinate synthase (dapA), dihydrodipicolinate reductase (dapB), diaminopimelate dehydrogenase (ddh), and diaminopimelate decarboxylase (lysA).

52 Claims, 36 Drawing Sheets

U.S. PATENT DOCUMENTS

| | | |
|---|---|---|
| 5,643,790 A | 7/1997 | Morinaga et al. ......... 435/252.3 |
| 5,650,304 A | 7/1997 | Ishii et al. .................. 435/115 |
| 5,661,012 A | 8/1997 | Sano et al. ................. 435/115 |
| 5,688,671 A | 11/1997 | Sugimoto et al. ........... 435/115 |
| 5,693,781 A | 12/1997 | Zupancic et al. .......... 536/24.1 |
| 5,700,661 A | 12/1997 | Katsumata et al. ........ 435/69.1 |
| 5,707,828 A | 1/1998 | Sreekrishna et al. ....... 435/69.1 |
| 5,726,299 A | 3/1998 | Zupancic et al. .......... 536/24.1 |
| 5,759,828 A | 6/1998 | Tal et al. ................. 435/172.3 |
| 5,766,925 A | 6/1998 | Sugimoto et al. ...... 435/252.32 |
| 5,773,691 A | 6/1998 | Falco et al. .................. 800/205 |
| 5,804,414 A | 9/1998 | Moriya et al. ............. 435/69.1 |
| 5,834,231 A | 11/1998 | Stoddard et al. ............. 435/42 |
| 5,846,790 A | 12/1998 | Kimura et al. .............. 435/110 |
| 5,876,983 A | 3/1999 | Sugimoto et al. ........... 435/106 |
| 5,888,783 A | 3/1999 | Tomita et al. .............. 435/115 |
| 5,919,670 A | 7/1999 | Okamoto et al. ........... 435/106 |
| 5,919,694 A | 7/1999 | Sugimoto et al. ...... 435/252.33 |
| 5,929,221 A | 7/1999 | Kimura et al. ............. 536/23.1 |
| 5,965,391 A | 10/1999 | Reinscheid et al. ........ 435/69.1 |
| 6,004,773 A | 12/1999 | Araki et al. .................. 435/41 |
| 6,027,920 A | 2/2000 | Joliff et al. ................. 435/69.7 |
| 6,057,299 A | 5/2000 | Henderson .................. 514/44 |
| 6,090,597 A | 7/2000 | Hirano et al. ............... 435/115 |
| 6,200,785 B1 | 3/2001 | Kreutzer et al. ............ 435/115 |
| 6,221,636 B1 | 4/2001 | Hayakawa et al. ......... 435/115 |

OTHER PUBLICATIONS

Ben–Samoun, K. et al., "Positively regulated expression of the *Escherichia coli* araBAD promoter in *Corynebacterium glutamicum*," *FEMS Microbiol. Lett.* 174:125–130, (May 1999).

Bowie, J.U. et al., "Deciphering the Message in Protein Sequences: Tolerance to Amino Acid Substitutions," *Science* 247:1306–1310, (1990).

Brutlag, D.L. et al., "Improved sensitivity of biological sequence database searches," *Comp. App. Biosci.* 6:237–245, (1990).

Copeland, R.A., "Cooperativity in Enzyme Catalysis," in *Enzymes. A Practical Introduction to Structure, Mechanism, and Data Analysis*, pp. 279–296, Wiley–VCH, New York (1996).

Cremer, J. et al., "Control of the Lysine Biosynthesis Sequence in *Corynebacterium glutamicum* as Analyzed by Overexpression of the Individual Corresponding Genes," *Appl. Environ. Microbiol.* 57:1746–1752, (1991).

Cremer, J. et al., "Regulation of enzymes of lysine biosynthesis in *Corynebacterium glutamicum*," *J. Gen. Microbiol.* 134:3221–3229, (1988).

Follettie, M. et al., "Gene Structure and Expression of the *Corynebacterium flavum* N13 ask–asd Operon," *J. Bacteriol.* 175:4096–4103, (1993).

Jobling, M.G. and Homes, R.K., "Construction of vectors with the p15a replicon, kanamycin resistance, inducible lacZα and pUC18 or pUC19 multiple cloning sites," *Nucleic Acids Res.* 18:5315–5316, (1990).

Kleeman, A. et al., "Amino Acids," in *Ullmann's Encyclopedia of Industrial Chemistry*, vol. A2, pp. 57–97, Weinham: VCH–Verlasgsgesellschaft (1985).

Liebl, W. et al., "Transfer of *Brevibacterium divaricatum* DSM 20297$^T$, '*Brevibacterium flavum*' DSM 20411, '*Brevibacterium lactofermentum*' DSM 20412 and DSM 1412, and *Corynebacterium lilium* DSM 20137$^T$ to *Corynebacterium glutamicum* and Their Distinction by rRNA Gene Restriction Patterns," *Int. J. Syst. Bacteriol.* 41:255–260, (1991).

Lonsdale, D.M. et al., "pFC1 to pFC7: A Novel Family of Combinatorial Cloning Vectors," *Plant Mol. Biol. Rep.* 13:343–345, (1995).

Malumbres, M. and Martin, J.F., "Molecular control mechanisms of lysine and threonine biosynthesis in amino acid–producing corynebacteria: Redirecting carbon flow," *FEMS Microbiol. Lett.* 143:103–114, (1996).

Marcel, T. et al., "Nucleotide sequence and organization of the upstream region of the *Corynbacterium glutamicum* lysA gene," *Mol. Microbiology* 4:1819–1830, (1990).

Nakayama, K. et al., "Microbial Production of Essential Amino Acids with *Corynebacterium glutamicum* Mutants," in *Nutritional Improvement of Food and Feed Proteins*, Friedman, ed., Plenum Press, New York, NY, pp. 649–661 (1978).

Oguiza, J.A. et al., "A Gene Encoding Arginyl–tRNA Synthetase Is Located in the Upstream Region of the lysA Gene in *Brevibacterium lactofermentum*: Regulation of argS–lysA Cluster Expression by Arginine," *J. Bacteriol.* 175:7356–7362, (1993).

Pátek, M. et al., "Promoters from *Corynebacterium glutamicum*: cloning, molecular analysis and search for a consensus motif," *Microbiology* 142:1297–1309, (1996).

Pátek, M. et al., "Identification and transcriptional analysis of the dapB–ORF2–dapA–ORF4 operon of *Corynebacterium glutamicum*, encoding two enzymes involved in L–lysine synthesis," *Biotechnol. Lett.* 19:1113–1117, (Nov. 1997).

"pPMG–LIC Bacterial Cloning Vector and Cloning Kit," in *1999 Research Products Catalog*, BD Pharmingen, p. 839 (1999).

Record, M.T. et al., "*Escherichia coli* RNA Polymerase (Eσ$^{70}$), Promoters, and the Kinetics of the Steps of Transcription Initiation," in *Escherichia coli and Salmonella: Cellular and Molecular Biology*, American Society for Microbiology Press, pp. 792–821 (1996).

Reinscheid, D.J. et al., "Cloning, sequence analysis, expression and inactivation of the *Corynebacterium glutamicum* pta–ack operon encoding phophotransacetylase and acetate kinase," *Microbiology* 145:503–513, (Feb. 1999).

Sahm, H. et al., "Construction of L–lysine–, L–threonine–, or L–isoleucine–overproducing strains of *Corynebacterium glutamicum*," *Ann. N.Y. Acad. Sci.* 782:25–39, The New York Academy of Sciences (1996).

Schäfer, A. et al., "Small mobilizable multi–purpose cloning vectors derived from the *Escherichia coli* plasmids pK18 and pK19: selection of defined deletions in the chromosome of *Corynebacterium glutamicum*", *Gene* 145:69–73, (1994).

Van Walsem, H.J. and Thompson, M.C., "Simulated moving bed in the production of lysine," *J. Biotechnol.* 59:127–132, (1997).

Wendisch, V.F. et al., "Regulation of acetate metabolism in *Corynebacterium glutamicum*: transcriptional control of the isocitrate lyase and malate synthase genes," *Arch. Microbiol.* 168:262–269, (1997).

Derwent WPI, English language abstract of document AN1 (WO 00/63388) (Oct. 26, 2000), Accession No. 2000–687179/200067.

English language translation of claims of document AN1 (WO 00/63388) (Oct. 26, 2000).

English language translation of claims 10 and 11 only of document AN1 (WO 00/63388) (Oct. 26, 2000).

Serebrijski, I. et al., "Multicopy Suppression by asd Gene and Osmotic Stress–Dependent Complementation by Heterologous proA in proA Mutants," *J. Bact.* 177:7255–7260, (1995).

Kalinowski, J. et al., "Aspartokinase genes lysCα and lysCβ overlap and are adjacent to the aspartate β–semialdehyde dehydrogenase gene asd in *Corynebacterium glutamicum*," *Mol. Gen. Genet.* 224:317–324, (1990).

Serwold–Davis, T.M. et al., "Transformation of *Corynebacterium diphtheriae, Corynebacterium ulcerans, Corynebacterium glutamicum*, and *Escherichia coli* with the *C. diphtheriae* plasmid pNG2," *Proc. Natl. Acad. Sci. USA* 84:4964–4968, (1987).

Pisabarro, A., et al., "A Cluster of Three Genes (dapA, orf2, and dapB) of *Brevibacterium lactofermentum* Encodes Dihydrodipicolinate Synthase, Dihydrodipicolinate Reductase, and a Third Polypeptide of Unknown Funtion," *J. Bacteriol.* 175:2743–2749, (1993).

Yeh, P., et al., "Nucleotide sequence of the lysA gene of *Cornyebacterium glutamicum* and possible mechanisms for modulation of its expression," *Mol. Gen. Genet.* 212:112–119, (1988).

Database EMBL Acc. No. 221502, Pisabarro, A., et al. (Aug. 16, 1993).

Database EMBL Acc. No. AX122246, Nakagawa, S., et al. (May 11, 2001).

Database EMBL Acc. No. AX123535, Nakagawa, S., et al. (May 11, 2001).

Database EMBL Acc. No. AX125746, Nakagawa, S., et al. (May 10, 2001).

International Search Report for International Patent Application No. PCT/US00/35617, mailed Oct. 25, 2001.

Nucleotide sequence of ATCC21529 ask (SEQ ID NO:1)

```
   1  GTGGCCCTGG TCGTACAGAA ATATGGCGGT TCCTCGCTTG AGAGTGCGGA
  51  ACGCATTAGA AACGTCGCTG AACGGATCGT TGCCACCAAG AAGGCTGGAA
 101  ATGATGTCGT GGTTGTCTGC TCCGCAATGG AGACACCAC GGATGAACTT
 151  CTAGAACTTG CAGCGGCAGT GAATCCCGTT CCGCCAGCTC GTGAAATGGA
 201  TATGCTCCTG ACTGCTGGTG AGCGTATTTC TAACGCTCTC GTCGCCATGG
 251  CTATTGAGTC CCTTGGCGCA GAAGCTCAAT CTTTCACTGG CTCTCAGGCT
 301  GGTGTGCTCA CCACCGAGCG CCACGGAAAC GCACGCATTG TTGACGTCAC
 351  ACCGGGTCGT GTGCGTGAAG CACTCGATGA GGGCAAGATC TGCATTGTTG
 401  CTGGTTTTCA GGGTGTTAAT AAAGAAACCC GCGATGTCAC CACGTTGGGT
 451  CGTGGTGGTT CTGACACCAC TGCAGTTGCG TTGGCAGCTG CTTTGAACGC
 501  TGATGTGTGT GAGATTTACT CGGACGTTGA CGGTGTGTAT ACCGCTGACC
 551  CGCGCATCGT TCCTAATGCA CAGAAGCTGG AAAAGCTCAG CTTCGAAGAA
 601  ATGCTGGAAC TTGCTGCTGT TGGCTCCAAG ATTTTGGTGC TGCGCAGTGT
 651  TGAATACGCT CGTGCATTCA ATGTGCCACT TCGCGTACGC TCGTCTTATA
 701  GTAATGATCC CGGCACTTTG ATTGCCGGCT CTATGGAGGA TATTCCTGTG
 751  GAAGAAGCAG TCCTTACCGG TGTCGCAACC GACAAGTCCG AAGCCAAAGT
 801  AACCGTTCTG GGTATTTCCG ATAAGCCAGG CGAGGCTGCC AAGGTTTTCC
 851  GTGCGTTGGC TGATGCAGAA ATCAACATTG ACATGGTTCT GCAGAAcgtc
 901  tcctctgtGG AAGACGGCAC CACCGACATC ACGTTCACCT GCCCTCGCGC
 951  TGACGGACGC CGTGCGATGG AGATCTTGAA GAAGCTTCAG GTTCAGGGCA
1001  ACTGGACCAA TGTGCTTTAC GACGACCAGG TCGGCAAAGT CTCCCTCGTG
1051  GGTGCTGGCA TGAAGTCTCA CCCAGGTGTT ACCGCAGAGT TCATGGAAGC
1101  TCTGCGCGAT GTCAACGTGA ACATCGAATT GATTTCCATC TCTGAGATCC
1151  GCATTTCCGT GCTGATCCGT GAAGATGATC TGGATGCTGC TGCACGTGCA
1201  TTGCATGAGC AGTTCCAGCT GGGCGGCGAA GACGAAGCCG TCGTTTATGC
1251  AGGCACCGGA CGCTAA
```

FIG. 2

Amino Acid Sequence of ATTC21529 ask (SEQ ID NO:2)

```
      GTGGCCCTGGTCGTACAGAAATATGGCGGTTCCTCGCTTGAGAGTGCGGAACGCATTAGA
  1   ---------+---------+---------+---------+---------+---------+  60
       M  A  L  V  V  Q  K  Y  G  G  S  S  L  E  S  A  E  R  I  R

AACGTCGCTGAACGGATCGTTGCCACCAAGAAGGCTGGAAATGATGTCGTGGTTGTCTGC
 61   ---------+---------+---------+---------+---------+---------+ 120
       N  V  A  E  R  I  V  A  T  K  K  A  G  N  D  V  V  V  V  C

TCCGCAATGGGAGACACCACGGATGAACTTCTAGAACTTGCAGCGGCAGTGAATCCCGTT
121   ---------+---------+---------+---------+---------+---------+ 180
       S  A  M  G  D  T  T  D  E  L  L  E  L  A  A  A  V  N  P  V

CCGCCAGCTCGTGAAATGGATATGCTCCTGACTGCTGGTGAGCGTATTTCTAACGCTCTC
181   ---------+---------+---------+---------+---------+---------+ 240
       P  P  A  R  E  M  D  M  L  L  T  A  G  E  R  I  S  N  A  L

GTCGCCATGGCTATTGAGTCCCTTGGCGCAGAAGCTCAATCTTTCACTGGCTCTCAGGCT
241   ---------+---------+---------+---------+---------+---------+ 300
       V  A  M  A  I  E  S  L  G  A  E  A  Q  S  F  T  G  S  Q  A

GGTGTGCTCACCACCGAGCGCCACGGAAACGCACGCATTGTTGACGTCACACCGGGTCGT
301   ---------+---------+---------+---------+---------+---------+ 360
       G  V  L  T  T  E  R  H  G  N  A  R  I  V  D  V  T  P  G  R

GTGCGTGAAGCACTCGATGAGGGCAAGATCTGCATTGTTGCTGGTTTTCAGGGTGTTAAT
361   ---------+---------+---------+---------+---------+---------+ 420
       V  R  E  A  L  D  E  G  K  I  C  I  V  A  G  F  Q  G  V  N

AAAGAAACCCGCGATGTCACCACGTTGGGTCGTGGTGGTTCTGACACCACTGCAGTTGCG
421   ---------+---------+---------+---------+---------+---------+ 480
       K  E  T  R  D  V  T  T  L  G  R  G  G  S  D  T  T  A  V  A

TTGGCAGCTGCTTTGAACGCTGATGTGTGTGAGATTTACTCGGACGTTGACGGTGTGTAT
481   ---------+---------+---------+---------+---------+---------+ 540
       L  A  A  A  L  N  A  D  V  C  E  I  Y  S  D  V  D  G  V  Y

ACCGCTGACCCGCGCATCGTTCCTAATGCACAGAAGCTGGAAAAGCTCAGCTTCGAAGAA
541   ---------+---------+---------+---------+---------+---------+ 600
       T  A  D  P  R  I  V  P  N  A  Q  K  L  E  K  L  S  F  E  E

ATGCTGGAACTTGCTGCTGTTGGCTCCAAGATTTTGGTGCTGCGCAGTGTTGAATACGCT
601   ---------+---------+---------+---------+---------+---------+ 660
       M  L  E  L  A  A  V  G  S  K  I  L  V  L  R  S  V  E  Y  A
```

FIG.3A

```
     CGTGCATTCAATGTGCCACTTCGCGTACGCTCGTCTTATAGTAATGATCCCGGCACTTTG
661  ---------+---------+---------+---------+---------+---------+ 720
     R  A  F  N  V  P  L  R  V  R  S  S  Y  S  N  D  P  G  T  L

ATTGCCGGCTCTATGGAGGATATTCCTGTGGAAGAAGCAGTCCTTACCGGTGTCGCAACC
721  ---------+---------+---------+---------+---------+---------+ 780
     I  A  G  S  M  E  D  I  P  V  E  E  A  V  L  T  G  V  A  T

GACAAGTCCGAAGCCAAAGTAACCGTTCTGGGTATTTCCGATAAGCCAGGCGAGGCTGCC
781  ---------+---------+---------+---------+---------+---------+ 840
     D  K  S  E  A  K  V  T  V  L  G  I  S  D  K  P  G  E  A  A

AAGGTTTTCCGTGCGTTGGCTGATGCAGAAATCAACATTGACATGGTTCTGCAGAAcgtc
841  ---------+---------+---------+---------+---------+---------+ 900
     K  V  F  R  A  L  A  D  A  E  I  N  I  D  M  V  L  Q  N  V tcctctgtGGAAGACGGCACCACCGACATCACGTTCACCTGCCCTCGCGCTGACGGACGC
901  ---------+---------+---------+---------+---------+---------+ 960
     S  S  V  E  D  G  T  T  D  I  T  F  T  C  P  R  A  D  G  R CGTGCGATGGAGATCTTGAAGAAGCTTCAGGTTCAGGGCAACTGGACCAATGTGCTTTAC
961  ---------+---------+---------+---------+---------+---------+ 1020
     R  A  M  E  I  L  K  K  L  Q  V  Q  G  N  W  T  N  V  L  Y GACGACCAGGTCGGCAAAGTCTCCCTCGTGGGTGCTGGCATGAAGTCTCACCCAGGTGTT
1021 ---------+---------+---------+---------+---------+---------+ 1080
     D  D  Q  V  G  K  V  S  L  V  G  A  G  M  K  S  H  P  G  V ACCGCAGAGTTCATGGAAGCTCTGCGCGATGTCAACGTGAACATCGAATTGATTTCCATC
1081 ---------+---------+---------+---------+---------+---------+ 1140
     T  A  E  F  M  E  A  L  R  D  V  N  V  N  I  E  L  I  S  I TCTGAGATCCGCATTTCCGTGCTGATCCGTGAAGATGATCTGGATGCTGCTGCACGTGCA
1141 ---------+---------+---------+---------+---------+---------+ 1200
     S  E  I  R  I  S  V  L  I  R  E  D  D  L  D  A  A  A  R  A TTGCATGAGCAGTTCCAGCTGGGCGGCGAAGACGAAGCCGTCGTTTATGCAGGCACCGGA
1201 ---------+---------+---------+---------+---------+---------+ 1260
     L  H  E  Q  F  Q  L  G  G  E  D  E  A  V  V  Y  A  G  T  G

CGCTAA
1261 ------ 1266
     R  *
```

FIG.3B

Nucleotide sequence of ATCC21529 asd (SEQ ID NO:3)

```
   1  ATGACCACCA TCGCAGTTGT TGGTGCAACC GGCCAGGTCG GCCAGGTTAT
  51  GCGCACCTTT TTGGAAGAGC GCAATTTCCC AGCTGACACT GTTCGTTTCT
 101  TTGCTTCCCC GCGTTCCGCA GGCCGTAAGA TTGAATTCCG TGGCACGGAA
 151  ATCGAGGTAG AAGACATTAC TCAGGCAACC GAGGAGTCCC TCAAGGGCAT
 201  CGACGTTGCG TTGTTCTCTG CTGGAGGCAC CGCTTCCAAG CAGTACGCTC
 251  CACTGTTTGC TGCTGCAGGC GCGACTGTTG TGGATAACTC TTCTGCTTGG
 301  CGCAAGGACG ACGAGGTTCC ACTAATCGTC TCTGAGGTGA ACCCTTCCGA
 351  CAAGGATTCC CTGGTCAAGG GCATTATTGC GAATCCTAAC TGCACCACCA
 401  TGGCTGCAAT GCCAGTGCTG AAGCCACTGC ACGATGCCGC TGGTCTTGTA
 451  AAGCTTCACG TTTCCTCTTA CCAGGCTGTT TCCGGTTCTG GTCTTGCAGG
 501  TGTGGAAACC TTGGCAAAGC AGGTTGCTGC AGTTGGCGAC CACAACGTTG
 551  AGTTCGTCCA TGATGGACAG GCTGCTGACG CAGGCGATGT CGGACCTTAC
 601  GTTTCCCCAA TCGCTTACAA CGTGCTGCCA TTCGCCGGAA ACCTCGTCGA
 651  TGACGGCACC TTCGAAACCG ACGAAGAGCA GAAGCTGCGC AACGAATCCC
 701  GCAAGATTCT CGGCCTCCCA GACCTCAAGG TCTCAGGCAC CTGCGTCCGC
 751  GTGCCGGTTT TCACCGGCCA CACGCTGACC ATTCACGCCG AATTCGACAA
 801  GGCAATCACC GTCGAGCAGG CGCAGGAGAT CTTGGGTGCC GCTTCAGGCG
 851  TCGAGCTTGT CGACGTCCCA ACCCACTTG CAGCTGCCGG CATTGACGAA
 901  TCCCTCGTTG GACGCATCCG TCAGGACTCC ACTGTCGACG ACAACCGCGG
 951  TCTGGTTCTC GTCGTATCTG GCGATAACCT TCGCAAGGGC GCAGCACTGA
1001  ACACCATTCA GATTGCTGAG CTGCTGGTTA AGTAA
```

FIG. 4

Amino acid sequence of ATCC21529 asd (SEQ ID NO:4)

```
    ATGACCACCATCGCAGTTGTTGGTGCAACCGGCCAGGTCGGCCAGGTTATGCGCACCTTT
1   ---------+---------+---------+---------+---------+---------+ 60
    M  T  T  I  A  V  V  G  A  T  G  Q  V  G  Q  V  M  R  T  F

TTGGAAGAGCGCAATTTCCCAGCTGACACTGTTCGTTTCTTTGCTTCCCCGCGTTCCGCA
61  ---------+---------+---------+---------+---------+---------+ 120
    L  E  E  R  N  F  P  A  D  T  V  R  F  F  A  S  P  R  S  A

GGCCGTAAGATTGAATTCCGTGGCACGGAAATCGAGGTAGAAGACATTACTCAGGCAACC
121 ---------+---------+---------+---------+---------+---------+ 180
    G  R  K  I  E  F  R  G  T  E  I  E  V  E  D  I  T  Q  A  T

GAGGAGTCCCTCAAGGGCATCGACGTTGCGTTGTTCTCTGCTGGAGGCACCGCTTCCAAG
181 ---------+---------+---------+---------+---------+---------+ 240
    E  E  S  L  K  G  I  D  V  A  L  F  S  A  G  G  T  A  S  K

CAGTACGCTCCACTGTTTGCTGCTGCAGGCGCGACTGTTGTGGATAACTCTTCTGCTTGG
241 ---------+---------+---------+---------+---------+---------+ 300
    Q  Y  A  P  L  F  A  A  A  G  A  T  V  V  D  N  S  S  A  W

CGCAAGGACGACGAGGTTCCACTAATCGTCTCTGAGGTGAACCCTTCCGACAAGGATTCC
301 ---------+---------+---------+---------+---------+---------+ 360
    R  K  D  D  E  V  P  L  I  V  S  E  V  N  P  S  D  K  D  S

CTGGTCAAGGGCATTATTGCGAATCCTAACTGCACCACCATGGCTGCAATGCCAGTGCTG
361 ---------+---------+---------+---------+---------+---------+ 420
    L  V  K  G  I  I  A  N  P  N  C  T  T  M  A  A  M  P  V  L

AAGCCACTGCACGATGCCGCTGGTCTTGTAAAGCTTCACGTTTCCTCTTACCAGGCTGTT
421 ---------+---------+---------+---------+---------+---------+ 480
    K  P  L  H  D  A  A  G  L  V  K  L  H  V  S  S  Y  Q  A  V

TCCGGTTCTGGTCTTGCAGGTGTGGAAACCTTGGCAAAGCAGGTTGCTGCAGTTGGCGAC
481 ---------+---------+---------+---------+---------+---------+ 540
    S  G  S  G  L  A  G  V  E  T  L  A  K  Q  V  A  A  V  G  D
```

FIG. 5A

```
     CACAACGTTGAGTTCGTCCATGATGGACAGGCTGCTGACGCAGGCGATGTCGGACCTTAC
541  ---------+---------+---------+---------+---------+---------+ 600
     H  N  V  E  F  V  H  D  G  Q  A  A  D  A  G  D  V  G  P  Y

GTTTCCCCAATCGCTTACAACGTGCTGCCATTCGCCGGAAACCTCGTCGATGACGGCACC
601  ---------+---------+---------+---------+---------+---------+ 660
     V  S  P  I  A  Y  N  V  L  P  F  A  G  N  L  V  D  D  G  T

TTCGAAACCGACGAAGAGCAGAAGCTGCGCAACGAATCCCGCAAGATTCTCGGCCTCCCA
661  ---------+---------+---------+---------+---------+---------+ 720
     F  E  T  D  E  E  Q  K  L  R  N  E  S  R  K  I  L  G  L  P

GACCTCAAGGTCTCAGGCACCTGCGTCCGCGTGCCGGTTTTCACCGGCCACACGCTGACC
721  ---------+---------+---------+---------+---------+---------+ 780
     D  L  K  V  S  G  T  C  V  R  V  P  V  F  T  G  H  T  L  T

ATTCACGCCGAATTCGACAAGGCAATCACCGTCGAGCAGGCGCAGGAGATCTTGGGTGCC
781  ---------+---------+---------+---------+---------+---------+ 840
     I  H  A  E  F  D  K  A  I  T  V  E  Q  A  Q  E  I  L  G  A

GCTTCAGGCGTCGAGCTTGTCGACGTCCCAACCCCACTTGCAGCTGCCGGCATTGACGAA
841  ---------+---------+---------+---------+---------+---------+ 900
     A  S  G  V  E  L  V  D  V  P  T  P  L  A  A  A  G  I  D  E

TCCCTCGTTGGACGCATCCGTCAGGACTCCACTGTCGACGACAACCGCGGTCTGGTTCTC
901  ---------+---------+---------+---------+---------+---------+ 960
     S  L  V  G  R  I  R  Q  D  S  T  V  D  D  N  R  G  L  V  L

GTCGTATCTGGCGATAACCTTCGCAAGGGCGCAGCACTGAACACCATTCAGATTGCTGAG
961  ---------+---------+---------+---------+---------+---------+ 1020
     V  V  S  G  D  N  L  R  K  G  A  A  L  N  T  I  Q  I  A  E

CTGCTGGTTAAGTAA
1021 ---------+----- 1035
     L  L  V  K  *
```

FIG.5B

Nucleotide sequence of dapA (SEQ ID NO:5)

```
  1 ATGAGCACAG GTTTAACAGC TAAGACCGGA GTAGAGCACT TCGGCACCGT
 51 TGGAGTAGCA ATGGTTACTC CATTCACGGA ATCCGGAGAC ATCGATATCG
101 CTGCTGGCCG CGAAGTCGCG GCTTATTTGG TTGATAAGGG CTTGGATTCT
151 TTGGTTCTCG CGGGCACCAC TGGTGAATCC CCAACGACAA CCGCCGCTGA
201 AAAACTAGAA CTGCTCAAGG CCGTTCGTGA GGAAGTTGGG GATCGGGCGA
251 AGCTCATCGC CGGTGTCGGA ACCAACAACA CGCGGACATC TGTGGAACTT
301 GCGGAAGCTG CTGCTTCTGC TGGCGCAGAC GGCCTTTTAG TTGTAACTCC
351 TTATTACTCC AAGCCGAGCC AAGAGGGATT GCTGGCGCAC TTCGGTGCAA
401 TTGCTGCAGC AACAGAGGTT CCAATTTGTC TCTATGACAT TCCTGGTCGG
451 TCAGGTATTC CAATTGAATC TGATACCATG AGACGCCTGA GTGAATTACC
501 TACGATTTTG GCGGTCAAGG ACGCCAAGGG TGACCTCGTT GCAGCCACGT
551 CATTGATCAA AGAAACGGGA CTTGCCTGGT ATTCAGGCGA TGACCCACTA
601 AACCTTGTTT GGCTTGCTTT GGGCGGATCA GGTTTCATTT CCGTAATTGG
651 ACATGCAGCC CCCACAGCAT TACGTGAGTT GTACACAAGC TTCGAGGAAG
701 GCGACCTCGT CCGTGCGCGG GAAATCAACG CCAAACTATC ACCGCTGGTA
751 GCTGCCCAAG GTCGCTTGGG TGGAGTCAGC TTGGCAAAAG CTGCTcTGCG
801 TCTGCAGGGC ATCAACGTAG GAGATCCTCG ACTTCCAATT ATGGCTCCAA
851 ATGAGCAGGA ACTTGAGGCT CTCCGAGAAG ACATGAAAAA AGCTGGAGTT
901 CTATAA
```

FIG. 6

Amino acid sequence of dapA (SEQ ID NO:6)

```
    ATGAGCACAGGTTTAACAGCTAAGACCGGAGTAGAGCACTTCGGCACCGTTGGAGTAGCA
  1 ---------+---------+---------+---------+---------+---------+ 60
     M  S  T  G  L  T  A  K  T  G  V  E  H  F  G  T  V  G  V  A

ATGGTTACTCCATTCACGGAATCCGGAGACATCGATATCGCTGCTGGCCGCGAAGTCGCG
 61 ---------+---------+---------+---------+---------+---------+ 120
     M  V  T  P  F  T  E  S  G  D  I  D  I  A  A  G  R  E  V  A

GCTTATTTGGTTGATAAGGGCTTGGATTCTTTGGTTCTCGCGGGCACCACTGGTGAATCC
121 ---------+---------+---------+---------+---------+---------+ 180
     A  Y  L  V  D  K  G  L  D  S  L  V  L  A  G  T  T  G  E  S

CCAACGACAACCGCCGCTGAAAAACTAGAACTGCTCAAGGCCGTTCGTGAGGAAGTTGGG
181 ---------+---------+---------+---------+---------+---------+ 240
     P  T  T  T  A  A  E  K  L  E  L  L  K  A  V  R  E  E  V  G

GATCGGGCGAAGCTCATCGCCGGTGTCGGAACCAACAACACGCGGACATCTGTGGAACTT
241 ---------+---------+---------+---------+---------+---------+ 300
     D  R  A  K  L  I  A  G  V  G  T  N  N  T  R  T  S  V  E  L

GCGGAAGCTGCTGCTTCTGCTGGCGCAGACGGCCTTTTAGTTGTAACTCCTTATTACTCC
301 ---------+---------+---------+---------+---------+---------+ 360
     A  E  A  A  A  S  A  G  A  D  G  L  L  V  V  T  P  Y  Y  S

AAGCCGAGCCAAGAGGGATTGCTGGCGCACTTCGGTGCAATTGCTGCAGCAACAGAGGTT
361 ---------+---------+---------+---------+---------+---------+ 420
     K  P  S  Q  E  G  L  L  A  H  F  G  A  I  A  A  A  T  E  V

CCAATTTGTCTCTATGACATTCCTGGTCGGTCAGGTATTCCAATTGAATCTGATACCATG
421 ---------+---------+---------+---------+---------+---------+ 480
     P  I  C  L  Y  D  I  P  G  R  S  G  I  P  I  E  S  D  T  M
```

FIG. 7A

```
         AGACGCCTGAGTGAATTACCTACGATTTTGGCGGTCAAGGACGCCAAGGGTGACCTCGTT
    481  ---------+---------+---------+---------+---------+---------+  540

R  R  L  S  E  L  P  T  I  L  A  V  K  D  A  K  G  D  L  V

GCAGCCACGTCATTGATCAAAGAAACGGGACTTGCCTGGTATTCAGGCGATGACCCACTA
    541  ---------+---------+---------+---------+---------+---------+  600

A  A  T  S  L  I  K  E  T  G  L  A  W  Y  S  G  D  D  P  L

AACCTTGTTTGGCTTGCTTTGGGCGGATCAGGTTTCATTTCCGTAATTGGACATGCAGCC
    601  ---------+---------+---------+---------+---------+---------+  660

N  L  V  W  L  A  L  G  G  S  G  F  I  S  V  I  G  H  A  A

CCCACAGCATTACGTGAGTTGTACACAAGCTTCGAGGAAGGCGACCTCGTCCGTGCGCGG
    661  ---------+---------+---------+---------+---------+---------+  720

P  T  A  L  R  E  L  Y  T  S  F  E  E  G  D  L  V  R  A  R

GAAATCAACGCCAAACTATCACCGCTGGTAGCTGCCCAAGGTCGCTTGGGTGGAGTCAGC
    721  ---------+---------+---------+---------+---------+---------+  780

E  I  N  A  K  L  S  P  L  V  A  A  Q  G  R  L  G  G  V  S

TTGGCAAAAGCTGCTctGCGTCTGCAGGGCATCAACGTAGGAGATCCTCGACTTCCAATT
    781  ---------+---------+---------+---------+---------+---------+  840

L  A  K  A  A  L  R  L  Q  G  I  N  V  G  D  P  R  L  P  I

ATGGCTCCAAATGAGCAGGAACTTGAGGCTCTCCGAGAAGACATGAAAAAAGCTGGAGTT
    841  ---------+---------+---------+---------+---------+---------+  900

M  A  P  N  E  Q  E  L  E  A  L  R  E  D  M  K  K  A  G  V

CTATAA
    901  ------  906

Nucleotide sequence of dapB (SEQ ID NO:7)

```
  1 ATGGGAATCA AGGTTGGCGT TCTCGGAGCC AAAGGCCGTG TTGGTCAAAC
 51 TATTGTGGCA GCAGTCAATG AGTCCGACGA TCTGGAGCTT GTTGCAGAGA
101 TCGGCGTCGA CGATGATTTG AGCCTTCTGG TAGACAACGG CGCTGAAGTT
151 GTCGTTGACT TCACCACTCC TAACGCTGTG ATGGGCAACC TGGAGTTCTG
201 CATCAACAAC GGCATTTCTG CGGTTGTTGG AACCACGGGC TTCGATaATG
251 CTCGTTTGGA GCAGGTTCGC GcCTGGCTTG AAGGAAAAGA CAATGTCGGT
301 GTTCTGATCG CACCTAACTT TGCTATCTCT GCGGTGTTGA CCATGGTCTT
351 TTCCAAGCAG GCTGCCCGCT TCTTCGAATC AGCTGAAGTT ATTGAGCTGC
401 ACCACCCCAA CAAGCTGGAT GCACCTTCAG GCACCGCGAT CCACACTGCT
451 CAGGGCATTG CTGCGGCACG CAAAGAAGCA GGCATGGACG CACAGCCAGA
501 TGCGACCGAG CAGGCACTTG AGGGTTCCCG TGGCGCAAGC GTAGATGGAA
551 TCCCaGTTCA cGCAGTCCGC ATGTCCGGCA TGGTTGCTCA CGAGCAAGTT
601 ATCTTTGGCA CCCAGGGTCA GACCTTGACC ATCAAGCAGG ACTCCTATGA
651 TCGCAACTCA TTTGCACCAG GTGTCTTGGT GGGTGTGCGC AACATTGCAC
701 AGCACCCAGG CCTAGTCGTA GGACTTGAGC ATTACCTAGG CCTGTAA
```

FIG. 8

Amino acid sequence of dapB (SEQ ID NO:8)

```
    ATGGGAATCAAGGTTGGCGTTCTCGGAGCCAAAGGCCGTGTTGGTCAAACTATTGTGGCA
  1 ..........+..........+..........+..........+..........+..........+ 60

M  G  I  K  V  G  V  L  G  A  K  G  R  V  G  Q  T  I  V  A

GCAGTCAATGAGTCCGACGATCTGGAGCTTGTTGCAGAGATCGGCGTCGACGATGATTTG
 61 ..........+..........+..........+..........+..........+..........+ 120

A  V  N  E  S  D  D  L  E  L  V  A  E  I  G  V  D  D  D  L

AGCCTTCTGGTAGACAACGGCGCTGAAGTTGTCGTTGACTTCACCACTCCTAACGCTGTG
121 ..........+..........+..........+..........+..........+..........+ 180

S  L  L  V  D  N  G  A  E  V  V  V  D  F  T  T  P  N  A  V

ATGGGCAACCTGGAGTTCTGCATCAACAACGGCATTTCTGCGGTTGTTGGAACCACGGGC
181 ..........+..........+..........+..........+..........+..........+ 240

M  G  N  L  E  F  C  I  N  N  G  I  S  A  V  V  G  T  T  G

TTCGATaATGCTCGTTTGGAGCAGGTTCGCGCcCTGGCTTGAAGGAAAAGACAATGTCGGT
241 ..........+..........+..........+..........+..........+..........+ 300

F  D  N  A  R  L  E  Q  V  R  A  W  L  E  G  K  D  N  V  G

GTTCTGATCGCACCTAACTTTGCTATCTCTGCGGTGTTGACCATGGTCTTTTTCCAAGCAG
301 ..........+..........+..........+..........+..........+..........+ 360

V  L  I  A  P  N  F  A  I  S  A  V  L  T  M  V  F  S  K  Q

GCTGCCCGCTTCTTCGAATCAGCTGAAGTTATTGAGCTGCACCACCCCAACAAGCTGGAT
361 ..........+..........+..........+..........+..........+..........+ 420

```
     GCACCTTCAGGCACCGCGATCCACACTGCTCAGGGCATTGCTGCGGCACGCAAAGAAGCA
421  ---------+---------+---------+---------+---------+---------+ 480

A  P  S  G  T  A  I  H  T  A  Q  G  I  A  A  A  R  K  E  A

GGCATGGACGCACAGCCAGATGCGACCGAGCAGGCACTTGAGGGTTCCCGTGGCGCAAGC
481  ---------+---------+---------+---------+---------+---------+ 540

G  M  D  A  Q  P  D  A  T  E  Q  A  L  E  G  S  R  G  A  S

GTAGATGGAATCCCaGTTCAcGCAGTCCGCATGTCCGGCATGGTTGCTCACGAGCAAGTT
541  ---------+---------+---------+---------+---------+---------+ 600

V  D  G  I  P  V  H  A  V  R  M  S  G  M  V  A  H  E  Q  V

ATCTTTGGCACCCAGGGTCAGACCTTGACCATCAAGCAGGACTCCTATGATCGCAACTCA
601  ---------+---------+---------+---------+---------+---------+ 660

I  F  G  T  Q  G  Q  T  L  T  I  K  Q  D  S  Y  D  R  N  S

TTTGCACCAGGTGTCTTGGTGGGTGTGCGCAACATTGCACAGCACCCAGGCCTAGTCGTA
661  ---------+---------+---------+---------+---------+---------+ 720

F  A  P  G  V  L  V  G  V  R  N  I  A  Q  H  P  G  L  V  V

GGACTTGAGCATTACCTAGGCCTGTAA
721  ---------+---------+------- 747

Nucleotide sequence of ddh (SEQ ID NO:9)

```
   1  ATGCATTTCG GTAAGCTCGA CCAGGACAGT GCCACCACAA TTTTGGAGGA
  51  TTACAAGAAC ATGACCAACA TCCGCGTAGC TATCGTaGGC TACGGAAACC
 101  TGGGACGCAG CGTCGAAAAG CTTATTGCCA AGCAGCCCGA CATGGACCTT
 151  GTAGGAATCT TCTCGCGCCG GGCCACCCTC GACACAAAGA CGCCAGTCTT
 201  TGATGTCGCC GACGTGGACA AGCACGCCGA CGACGTGGAC GTGCTGTTCC
 251  TGTGCATGGG CTCCGCCACC GACATCCCTG AGCAGGCACC AAAGTTCGCG
 301  CAGTTCGCCT GCACCGTAGA CACCTACGAC AACCACCGCG ACATCCCACG
 351  CCACCGCCAG GTCATGAACG AAGCCGCCAC CGCAGCCGGC AACGTTGCAC
 401  TGGTCTCTAC CGGCTGGGAT CCAGGAATGT TCTCCATCAA CCGCGTCTAC
 451  GCAGCGGCAG TCTTAGCCGA GCACCAGCAG CACACCTTCT GGGGCCCAGG
 501  TTTGTCACAG GGCCACTCCG ATGCTTTGCG ACGCATCCCT GGCGTTCAAA
 551  AGGCcGTCCA GTACACCCTC CCATCCGAAG AaGCCCTGGA AAAGGCCCGC
 601  CGTGGCGAAG CCGGCGACCT cACCGGAAAG CAAACCCACA AGCGCCAATG
 651  CTTCGTGGTT GCCGACGCGG CCGAcCACGA GCGCATCGAA AACGACATCC
 701  GCACCATGCC TGATTACTTC GTTGGCTACG AAGTCGAAGT CAACTTCATC
 751  GACGAAGCAA CCTTgGACgC CGAGCACACC GGCATGCCAC ACGGcGGaCA
 801  CGTGATcACC ACCGGCGACA CCGGTGGCTT CAACCACACC GTGGAATACA
 851  TCCTgAAGCT GGACCGAAAC CCAGATTTCA CCGCTTCttC ACAGATCGCT
 901  TTCGGcCGCG CAGCTCACCG CATGAAGCAG CAGGGCCAAA GCGGtGCTTT
 951  CACCGTCCTC GAAGTTGCTC CATACtTGCT CTCCCCgGAG AACTTGGAtG
1001  ATCTGATCGC ACGCGACGTC TAA
```

FIG. 10

Amino acid sequence of ddh (SEQ ID NO:10)

```
     ATGCATTTCGGTAAGCTCGACCAGGACAGTGCCACCACAATTTTGGAGGATTACAAGAAC
1    ---------+---------+---------+---------+---------+---------+ 60

M  H  F  G  K  L  D  Q  D  S  A  T  T  I  L  E  D  Y  K  N

ATGACCAACATCCGCGTAGCTATCGTaGGCTACGGAAACCTGGGACGCAGCGTCGAAAAG
61   ---------+---------+---------+---------+---------+---------+ 120

M  T  N  I  R  V  A  I  V  G  Y  G  N  L  G  R  S  V  E  K

CTTATTGCCAAGCAGCCCGACATGGACCTTGTAGGAATCTTCTCGCGCCGGGCCACCCTC
121  ---------+---------+---------+---------+---------+---------+ 180

L  I  A  K  Q  P  D  M  D  L  V  G  I  F  S  R  R  A  T  L

GACACAAAGACGCCAGTCTTTGATGTCGCCGACGTGGACAAGCACGCCGACGACGTGGAC
181  ---------+---------+---------+---------+---------+---------+ 240

D  T  K  T  P  V  F  D  V  A  D  V  D  K  H  A  D  D  V  D

GTGCTGTTCCTGTGCATGGGCTCCGCCACCGACATCCCTGAGCAGGCACCAAAGTTCGCG
241  ---------+---------+---------+---------+---------+---------+ 300

V  L  F  L  C  M  G  S  A  T  D  I  P  E  Q  A  P  K  F  A

CAGTTCGCCTGCACCGTAGACACCTACGACAACCACCGCGACATCCCACGCCACCGCCAG
301  ---------+---------+---------+---------+---------+---------+ 360

Q  F  A  C  T  V  D  T  Y  D  N  H  R  D  I  P  R  H  R  Q

GTCATGAACGAAGCCGCCACCGCAGCCGGCAACGTTGCACTGGTCTCTACCGGCTGGGAT
361  ---------+---------+---------+---------+---------+---------+ 420

V  M  N  E  A  A  T  A  A  G  N  V  A  L  V  S  T  G  W  D

CCAGGAATGTTCTCCATCAACCGCGTCTACGCAGCGGCAGTCTTAGCCGAGCACCAGCAG
421  ---------+---------+---------+---------+---------+---------+ 480

P  G  M  F  S  I  N  R  V  Y  A  A  A  V  L  A  E  H  Q  Q

CACACCTTCTGGGGCCCAGGTTTGTCACAGGGCCACTCCGATGCTTTGCGACGCATCCCT
481  ---------+---------+---------+---------+---------+---------+ 540

```
     GGCGTTCAAAAGGCcGTCCAGTACACCCTCCCATCCGAAGAaGCCCTGGAAAAGGCCCGC
541  ---------+---------+---------+---------+---------+---------+ 600
     G  V  Q  K  A  V  Q  Y  T  L  P  S  E  E  A  L  E  K  A  R

CGTGGCGAAGCCGGCGACCTcACCGGAAAAGCAAACCCACAAGCGCCAATGCTTCGTGGTT
601  ---------+---------+---------+---------+---------+---------+ 660
     R  G  E  A  G  D  L  T  G  K  Q  T  H  K  R  Q  C  F  V  V

GCCGACGCGGCCGAcCACGAGCGCATCGAAAACGACATCCGCACCATGCCTGATTACTTC
661  ---------+---------+---------+---------+---------+---------+ 720
     A  D  A  A  D  H  E  R  I  E  N  D  I  R  T  M  P  D  Y  F

GTTGGCTACGAAGTCGAAGTCAACTTCATCGACGAAGCAACCTTgGACgCCGAGCACACC
721  ---------+---------+---------+---------+---------+---------+ 780
     V  G  Y  E  V  E  V  N  F  I  D  E  A  T  L  D  A  E  H  T

GGCATGCCACACGGcGGaCACGTGATcACCACCGGCGACACCGGTGGCTTCAACCACACC
781  ---------+---------+---------+---------+---------+---------+ 840
     G  M  P  H  G  G  H  V  I  T  T  G  D  T  G  G  F  N  H  T

GTGGAATACATCCTgAAGCTGGACCGAAACCCAGATTTCACCGCTTCtTCACAGATCGCT
841  ---------+---------+---------+---------+---------+---------+ 900
     V  E  Y  I  L  K  L  D  R  N  P  D  F  T  A  S  S  Q  I  A

TTCGGcCGCGCAGCTCACCGCATGAAGCAGCAGGGCCAAAGCGGtGCTTTCACCGTCCTC
901  ---------+---------+---------+---------+---------+---------+ 960
     F  G  R  A  A  H  R  M  K  Q  Q  G  Q  S  G  A  F  T  V  L

GAAGTTGCTCCATACtTGCTCTCCCCgGAGAACTTGGAtGATCTGATCGCACGCGACGTC
961  ---------+---------+---------+---------+---------+---------+ 1020
     E  V  A  P  Y  L  L  S  P  E  N  L  D  D  L  I  A  R  D  V

TAA
1021 --- 1023
```

FIG.11B

Sequence of full length LysA from NRRL B-11474 (SEQ ID NO: 11):
Underlined region: the priming site for lysA primer ATGGCTACAGTTGAAAATTTCAATGAACTTCCCGCACACGTATGGCCACGCAATGCAGTG
CGCCAAGAAGACGGCGTTGTCACCGTCGCTGGTGTGCCTCTGCCTGACCTCGCTGAAGAA
TACGGAACCCCACTGTTCGTAGTCGACGAGGACGATTTCCGTTCCCGCTGTCGCGACATG
GCTACCGCATTCGGTGGACCAGGCAATGTGCACTACGCATCCAAAGCGTTCCTGACCAAG
ACCATTGCACGTTGGGTTGATGAAGAGGGGCTGGCACTGGACATTGCGTCCATCAATGAA
CTGGGCATTGCCCTGGCCGCTGGTTTCCCGGCCAGCCGTATCACCGCGCACGGCAACAAC
AAAGGCGTAGAGTTCCTGCGCGCGTTGGTTCAAAACGGTGTCGGGCATGTGGTGCTGGAC
TCCGCGCAGGAATTGGAACTGCTGGATTACGTTGCCGCTGGTGAAGGCAAGATCCAGGAC
GTGTTGATCCGCGTGAAGCCAGGTATCGAAGCCCACACCCACGAGTTCATCGCCACTAGC
CACGAAGACCAGAAGTTCGGATTCTCCCTGGCATCCGGTTCCGCATTCGAAGCAGCGAAA
GCAGCCAACAATGCAGAGAACTTGAACCTGGTTGGTCTGCACTGCCATGTTGGTTCCCAG
GTGTTCGACGCCGAAGGCTTCAAGCTGGCAGCAGAGCGCGTGTTGGGCCTGTACTCACAG
ATCCACAGCGAACTAGGTGTCGCCCTTCCTGAGCTGGACCTCGGTGGCGGATACGGCATC
GCCTACACTGCAGATGAGGAACCACTCAACGTCGCAGAAGTCGCCTCCGACCTACTCACC
GCAGTCGGAAAAATGGCAGCGGAACTAGGCATCGACGCACCAACCGTGCTTGTTGAGCCC
GGCCGCGCTATCGCAGGCCCCTCCACCGTGACCATCTACGAAGTCGGCACCACCAAAAAC
GTCCACGTAGACGACGACAAAACCCGCCGCTACGTAGCCGTCGACGGAGGCATGTCCGAC
AACATCCGCCCAGCACTCTACGGCTCCGAATACGACGCCCGCGTAGTATCCCGCTTCGCC
GAAGGAGACCCAGTAAGCACCCGCATCGTGGGCTCCCACTGCGAATCCGGCGATATCCTG
ATCAACGATGAAATCTACCCATCTGACATCACCAGCGGCGACTTCCTCGCACTCGCAGCC
ACCGGCGCATACTGCTACGCCATGAGCTCCCGCTACAACGCCTTCACACGGCCCGCCGTC
GTGTCCGTCCGCGCTGGCAGCTCCCGCCTCATGCTGCGCCGCGAAACCCTCGACGACATC
CTCTCACTAGAGGCATAA

FIG.12

Full length sequence of LysA (NRRL-B11474)
DIAMINOPIMELATE DECARBOXYLASE (Lys A) (SEQ ID NO:12)

MATVENFNELPAHVWPRNAVRQEDGVVTVAGVPLPDLAEEYGTPLFVVDEDDFRSRCRDM
ATAFGGPGNVHYASKAFLTKTIARWVDEEGLALDIASINELGIALAAGFPASRITAHGNN
KGVEFLRALVQNGVGHVVLDSAQELELLDYVAAGEGKIQDVLIRVKPGIEAHTHEFIATS
HEDQKFGFSLASGSAFEAAKAANNAENLNLVGLHCHVGSQVFDAEGFKLAAERVLGLYSQ
IHSELGVALPELDLGGGYGIAYTADEEPLNVAEVASDLLTAVGKMAAELGIDAPTVLVEP
GRAIAGPSTVTIYEVGTTKNVHVDDDKTRRYVAVDGGMSDNIRPALYGSEYDARVVSRFA
EGDPVSTRIVGSHCESGDILINDEIYPSDITSGDFLALAATGAYCYAMSSRYNAFTRPAV
VSVRAGSSRLMLRRETLDDILSLEA

FIG. 13

Nucleotide sequence of AS019 lysA (SEQ ID NO:13) (pRS6)

```
   1  ATGGCTACAG TTGAAAATTT CAATGAACTT CCCGCACACG TATGGCCACG
  51  CAATGCCGTG CGCCAAGAAG ACGGCGTTGT CACCGTCGCT GGTGTGCCTC
 101  TGCCTGACCT CGCTGAAGAA TACGGAACCC CACTGTTCGT AGTCGACGAG
 151  GACGATTTCC GTTCCCGCTG TCGCGACATG GCTACCGCAT TCGGTGGACC
 201  AGGCAATGTG CACTACGCAT CTAAAGCGTT CCTGACCAAG ACCATTGCAC
 251  GTTGGGTTGA TGAAGAGGGG CTGGCACTGG ACATTGCATC CATCAACGAA
 301  CTGGGCATTG CCCTGGCCGC TGGTTTCCCC GCCAGCCGTA TCACCGCGCA
 351  CGGCAACAAC AAAGGCGTAG AGTTCCTGCG CGCGTTGGTT CAAAACGGTG
 401  TGGGACACGT GGTGCTGGAC TCCGCACAGG AACTAGAACT GTTGGATTAC
 451  GTTGCCGCTG GTGAAGGCAA GATTCAGGAC GTGTTGATCC GCGTAAAGCC
 501  AGGCATCGAA GCACACACCC ACGAGTTCAT CGCCACTAGC CACGAAGACC
 551  AGAAGTTCGG ATTCTCCCTG CATCCGGTT CCGCATTCGA AGCAGCAAAA
 601  GCCGCCAACA ACGCAGAAAA CCTGAACCTG GTTGGCCTGC ACTGCCACGT
 651  TGGTTCCCAG TGTTCGACG CCGAAGGCTT CAAGCTGGCA GCAGAACGCG
 701  TGTTGGGCCT GTACTCACAG ATCCACAGCG AACTGGGCGT TGCCCTTCCT
 751  GAACTGGATC TCGGTGGCGG ATACGGCATT GCCTATACCG CAGCTGAAGA
 801  ACCACTCAAC GTCGCAGAAG TTGCCTCCGA CCTGCTCACC GCAGTCGGAA
 851  AAATGGCAGC GGAACTAGGC ATCGACGCAC CAACCGTGCT TGTTGAGCCC
 901  GGCCGCGCTA TCGCAGGCCC CTCCACCGTG ACCATCTACG AAGTCGGCAC
 951  CACCAAAGAC GTCCACGTAG ACGACGACAA AACCCGCCGT TACATCGCCG
1001  TGGACGGAGG CATGTCCGAC AACATCCGCC CAGCACTCTA CGGCTCCGAA
1051  TACGACGCCC GCGTAGTATC CCGCTTCGCC GAAGGAGACC CAGTAAGCAC
1101  CCGCATCGTG GGCTCCCACT GCGAATCCGG CGATATCCTG ATCAACGATG
1151  AAATCTACCC ATCTGACATC ACCAGCGGCG ACTTCCTTGC ACTCGCAGCC
1201  ACCGGCGCAT ACTGCTACGC CATGAGCTCC CGCTACAACG CCTTCACACG
1251  GCCCGCCGTC GTGTCCGTCC GCGCTGGCAG CTCCCGCCTC ATGCTGCGCC
1301  GCGAAACGCT CGACGACATC CTCTCACTAG AGGCATAA
```

FIG.14

Full length amino acid sequence of lysA (pRS6)(SEQ ID NO:14)

```
    ATGGCTACAGTTGAAAATTTCAATGAACTTCCCGCACACGTATGGCCACGCAATGCCGTG
  1 ---------+---------+---------+---------+---------+---------+ 60
    M  A  T  V  E  N  F  N  E  L  P  A  H  V  W  P  R  N  A  V

CGCCAAGAAGACGGCGTTGTCACCGTCGCTGGTGTGCCTCTGCCTGACCTCGCTGAAGAA
 61 ---------+---------+---------+---------+---------+---------+ 120
    R  Q  E  D  G  V  V  T  V  A  G  V  P  L  P  D  L  A  E  E

TACGGAACCCCACTGTTCGTAGTCGACGAGGACGATTTCCGTTCCCGCTGTCGCGACATG
121 ---------+---------+---------+---------+---------+---------+ 180
    Y  G  T  P  L  F  V  V  D  E  D  D  F  R  S  R  C  R  D  M

GCTACCGCATTCGGTGGACCAGGCAATGTGCACTACGCATCTAAAGCGTTCCTGACCAAG
181 ---------+---------+---------+---------+---------+---------+ 240
    A  T  A  F  G  G  P  G  N  V  H  Y  A  S  K  A  F  L  T  K

ACCATTGCACGTTGGGTTGATGAAGAGGGGCTGGCACTGGACATTGCATCCATCAACGAA
241 ---------+---------+---------+---------+---------+---------+ 300
    T  I  A  R  W  V  D  E  E  G  L  A  L  D  I  A  S  I  N  E

CTGGGCATTGCCCTGGCCGCTGGTTTCCCCGCCAGCCGTATCACCGCGCACGGCAACAAC
301 ---------+---------+---------+---------+---------+---------+ 360
    L  G  I  A  L  A  A  G  F  P  A  S  R  I  T  A  H  G  N  N

AAAGGCGTAGAGTTCCTGCGCGCGTTGGTTCAAAACGGTGTGGGACACGTGGTGCTGGAC
361 ---------+---------+---------+---------+---------+---------+ 420
    K  G  V  E  F  L  R  A  L  V  Q  N  G  V  G  H  V  V  L  D

TCCGCACAGGAACTAGAACTGTTGGATTACGTTGCCGCTGGTGAAGGCAAGATTCAGGAC
421 ---------+---------+---------+---------+---------+---------+ 480
    S  A  Q  E  L  E  L  L  D  Y  V  A  A  G  E  G  K  I  Q  D
```

FIG.15A

```
         GTGTTGATCCGCGTAAAGCCAGGCATCGAAGCACACACCCACGAGTTCATCGCCACTAGC
481      ---------+---------+---------+---------+---------+---------+ 540
          V  L  I  R  V  K  P  G  I  E  A  H  T  H  E  F  I  A  T  S

CACGAAGACCAGAAGTTCGGATTCTCCCTGGCATCCGGTTCCGCATTCGAAGCAGCAAAA
541      ---------+---------+---------+---------+---------+---------+ 600
          H  E  D  Q  K  F  G  F  S  L  A  S  G  S  A  F  E  A  A  K

GCCGCCAACAACGCAGAAAACCTGAACCTGGTTGGCCTGCACTGCCACGTTGGTTCCCAG
601      ---------+---------+---------+---------+---------+---------+ 660
          A  A  N  N  A  E  N  L  N  L  V  G  L  H  C  H  V  G  S  Q

GTGTTCGACGCCGAAGGCTTCAAGCTGGCAGCAGAACGCGTGTTGGGCCTGTACTCACAG
661      ---------+---------+---------+---------+---------+---------+ 720
          V  F  D  A  E  G  F  K  L  A  A  E  R  V  L  G  L  Y  S  Q

ATCCACAGCGAACTGGGCGTTGCCCTTCCTGAACTGGATCTCGGTGGCGGATACGGCATT
721      ---------+---------+---------+---------+---------+---------+ 780
          I  H  S  E  L  G  V  A  L  P  E  L  D  L  G  G  G  Y  G  I

GCCTATACCGCAGCTGAAGAACCACTCAACGTCGCAGAAGTTGCCTCCGACCTGCTCACC
781      ---------+---------+---------+---------+---------+---------+ 840
          A  Y  T  A  A  E  E  P  L  N  V  A  E  V  A  S  D  L  L  T

GCAGTCGGAAAAATGGCAGCGGAACTAGGCATCGACGCACCAACCGTGCTTGTTGAGCCC
841      ---------+---------+---------+---------+---------+---------+ 900
          A  V  G  K  M  A  A  E  L  G  I  D  A  P  T  V  L  V  E  P

GGCCGCGCTATCGCAGGCCCCTCCACCGTGACCATCTACGAAGTCGGCACCACCAAAGAC
901      ---------+---------+---------+---------+---------+---------+ 960
          G  R  A  I  A  G  P  S  T  V  T  I  Y  E  V  G  T  T  K  D
```

FIG. 15B

```
       GTCCACGTAGACGACGACAAAACCCGCCGTTACATCGCCGTGGACGGAGGCATGTCCGAC
  961  ----------+----------+----------+----------+----------+----------+  1020

V  H  V  D  D  K  T  R  R  Y  I  A  V  D  G  G  M  S  D

AACATCCGCCCAGCACTCTACGGCTCCGAATACGACGCCCGCGTAGTATCCCGCTTCGCC
 1021  ----------+----------+----------+----------+----------+----------+  1080

N  I  R  P  A  L  Y  G  S  E  Y  D  A  R  V  V  S  R  F  A

GAAGGAGACCCAGTAAGCACCCGCATCGTGGGCTCCCACTGCGAATCCGGCGATATCCTG
 1081  ----------+----------+----------+----------+----------+----------+  1140

E  G  D  P  V  S  T  R  I  V  G  S  H  C  E  S  G  D  I  L

ATCAACGATGAAATCTACCCATCTGACATCACCAGCGGCGACTTCCTTGCACTCGCAGCC
 1141  ----------+----------+----------+----------+----------+----------+  1200

I  N  D  E  I  Y  P  S  D  I  T  S  G  D  F  L  A  L  A  A

ACCGGCGCATACTGCTACGCCATGAGCTCCCGCTACAACGCCTTCACACGGCCCGCCGTC
 1201  ----------+----------+----------+----------+----------+----------+  1260

T  G  A  Y  C  Y  A  M  S  S  R  Y  N  A  F  T  R  P  A  V

GTGTCCGTCCGCGCTGGCAGCTCCCGCCTCATGCTGCGCCGCGAAACGCTCGACGACATC
 1261  ----------+----------+----------+----------+----------+----------+  1320

V  S  V  R  A  G  S  S  R  L  M  L  R  R  E  T  L  D  D  I

CTCTCACTAGAGGCATAA
 1321  ----------+--------  1338

Nucleotide sequence of orf2 in dapBA operon (SEQ ID NO:15)

```
  1 GTGGCCGAAC AAGTTAAATT GAGCGTGGAG TTGATAGCGT GCAGTTCTTT
 51 TACTCCACCC GCTGATGTTG AGTGGTCAAC TGATGTTGAG GGCGCGGAAG
101 CACTCGTCGA GTTTGCGGGT CGTGCCTGCT ACGAAACTTT TGATAAGCCG
151 AACCCTCGAA CTGCTTCCAA TGCTGCGTAT CTGCGCCACA TCATGGAAGT
201 GGGGCACACT GCTTTGCTTG AGCATGCCAA TGCCACGATG TATATCCGAG
251 GCATTTCTCG GTCCGCGACC CATGAATTGG TCCGACACCG CCATTTTTCC
301 TTCTCTCAAC TGTCTCAGCG TTTCGTGCAC AGCGGAGAAT CGGAAGTAGT
351 GGTGCCCACT CTCATCGATG AAGATCCGCA GTTGCGTGAA CTTTTCATGC
401 ACGCCATGGA TGAGTCTCGG TTCGCTTTCA ATGAGCTGCT TAATGCGCTG
451 GAAGAAAAAC TTGGCGATGA ACCGAATGCA CTTTTAAGGA AAAAGCAGGC
501 TCGTCAAGCA GCTCGCGCTG TGCTGCCCAA CGCTACAGAG TCCAGAATCG
551 TGGTGTCTGG AAACTTCCGC ACCTGGAGGC ATTTCATTGG CATGCGAGCC
601 AGTGAACATG CAGACGTCGA AATCCGCGAA GTAGCGGTAG GATGTTTAAG
651 AAAGCTGCAG GTAGCAGCGC CAACTGTTTT CGGTGATTTT GAGATTGAAA
701 CTTTGGCAGA CGGATCGCAA ATGGCAACAA GCCCGTATGT CATGGACTTT
751 TAA
```

FIG.16

ORF2 amino acid sequence (SEQ ID NO:16)

```
      GTGGCCGAACAAGTTAAATTGAGCGTGGAGTTGATAGCGTGCAGTTCTTTTACTCCACCC
  1   ------+---------+---------+---------+---------+---------+  60

M  A  E  Q  V  K  L  S  V  E  L  I  A  C  S  S  F  T  P  P

GCTGATGTTGAGTGGTCAACTGATGTTGAGGGCGCGGAAGCACTCGTCGAGTTTGCGGGT
 61   ------+---------+---------+---------+---------+---------+ 120

A  D  V  E  W  S  T  D  V  E  G  A  E  A  L  V  E  F  A  G

CGTGCCTGCTACGAAACTTTTGATAAGCCGAACCCTCGAACTGCTTCCAATGCTGCGTAT
121   ------+---------+---------+---------+---------+---------+ 180

R  A  C  Y  E  T  F  D  K  P  N  P  R  T  A  S  N  A  A  Y

CTGCGCCACATCATGGAAGTGGGGCACACTGCTTTGCTTGAGCATGCCAATGCCACGATG
181   ------+---------+---------+---------+---------+---------+ 240

L  R  H  I  M  E  V  G  H  T  A  L  L  E  H  A  N  A  T  M

TATATCCGAGGCATTTCTCGGTCCGCGACCCATGAATTGGTCCGACACCGCCATTTTTCC
241   ------+---------+---------+---------+---------+---------+ 300

Y  I  R  G  I  S  R  S  A  T  H  E  L  V  R  H  R  H  F  S

TTCTCTCAACTGTCTCAGCGTTTCGTGCACAGCGGAGAATCGGAAGTAGTGGTGCCCACT
301   ------+---------+---------+---------+---------+---------+ 360

F  S  Q  L  S  Q  R  F  V  H  S  G  E  S  E  V  V  V  P  T

CTCATCGATGAAGATCCGCAGTTGCGTGAACTTTTCATGCACGCCATGGATGAGTCTCGG
361   ------+---------+---------+---------+---------+---------+ 420

```
     TTCGCTTTCAATGAGCTGCTTAATGCGCTGGAAGAAAAACTTGGCGATGAACCGAATGCA
421  ---------+---------+---------+---------+---------+---------+ 480

F  A  F  N  E  L  L  N  A  L  E  E  K  L  G  D  E  P  N  A

CTTTTAAGGAAAAAGCAGGCTCGTCAAGCAGCTCGCGCTGTGCTGCCCAACGCTACAGAG
481  ---------+---------+---------+---------+---------+---------+ 540

L  L  R  K  K  Q  A  R  Q  A  A  R  A  V  L  P  N  A  T  E

TCCAGAATCGTGGTGTCTGGAAACTTCCGCACCTGGAGGCATTTCATTGGCATGCGAGCC
541  ---------+---------+---------+---------+---------+---------+ 600

S  R  I  V  V  S  G  N  F  R  T  W  R  H  F  I  G  M  R  A

AGTGAACATGCAGACGTCGAAATCCGCGAAGTAGCGGTAGGATGTTTAAGAAAGCTGCAG
601  ---------+---------+---------+---------+---------+---------+ 660

S  E  H  A  D  V  E  I  R  E  V  A  V  G  C  L  R  K  L  Q

GTAGCAGCGCCAACTGTTTTCGGTGATTTTGAGATTGAAACTTTGGCAGACGGATCGCAA
661  ---------+---------+---------+---------+---------+---------+ 720

V  A  A  P  T  V  F  G  D  F  E  I  E  T  L  A  D  G  S  Q

ATGGCAACAAGCCCGTATGTCATGGACTTTTAA
721  ---------+---------+---------+--- 753

```
              1                                                         50
ATCC 13032                                                     V
N13                                                            C
ATCC 21529                                                     C
    Consensus MALVVQKYGG SSLESAERIR NVAERIVATK KAGNDVVVVC SAMGDTTDEL 51                                                        100
ATCC 13032
N13
ATCC 21529
    Consensus LELAAAVNPV PPAREMDMLL TAGERISNAL VAMAIESLGA EAQSFTGSQA 101                                                       150
ATCC 13032
N13
ATCC 21529
    Consensus GVLTTERHGN ARIVDVTPGR VREALDEGKI CIVAGFQGVN KETRDVTTLG 151                                                       200
ATCC 13032
N13
ATCC 21529
    Consensus RGGSDTTAVA LAAALNADVC EIYSDVDGVY TADPRIVPNA QKLEKLSFEE 201                                                       250
ATCC 13032
N13
ATCC 21529
    Consensus MLELAAVGSK ILVLRSVEYA RAFNVPLRVR SSYSNDPGTL IAGSMEDIPV 251                                                       300
ATCC 13032
N13
ATCC 21529
    Consensus EEAVLTGVAT DKSEAKVTVL GISDKPGEAA KVFRALADAE INIDMVLQNV 301                S                         G
ATCC 13032                       A                         D
N13                              A                         G
ATCC 21529   SSVEDGTTDI TFTCPRADGR RAMEILKKLQ VQGNWTNVLY DDQVGKVSLV
    Consensus 351                              T                        400
ATCC 13032                                     T
N13                                            I
ATCC 21529
    Consensus GAGMKSHPGV TAEFMEALRD VNVNIELIST SEIRISVLIR EDDLDAAARA 401        421
ATCC 13032
N13
ATCC 21529
    Consensus LHEQFQLGGE DEAVVYAGTG R
```

FIG. 19

HpaI-PvuII fragment comprising the P1 promoter (SEQ ID NO:17)

```
AACCGGTGTGGAGCCGACCATTCCGCGAGGCTGCACTGCAACGAGGTCGTAGTTTTGGTACATGGCTTCTG
GCCAGTTCATGGATTGGCTGCCGAAGAAGCTATAGGCATCGCCACCAGGGCCACCGGAGTTACCGAAGATG
GTGCCGTGCTTTTCGCCTTGGGCAGGGACCTTGACAAAGCCCACGCTGATATCGCCAAGTGAGGGATCAGA
ATAGTGCATGGGCACGTCGATGCTGCCACATTGAGCGGAGGCAATATCTACCTGAGGTGGGCATTCTTCCC
AGCGGATGTTTTCTTGCGCTGCTGCAGTGGGCATTGATACCAAAAAGGGGCTAAGCGCAGTCGAGGCGGCA
AGAACTGCTACTACCTTTTTTATTGTCGAACGGGGCATTACGGCTCCAAGGACGTTTGTTTTCTGGGTCAG
TTACCCCAAAAAGCATATACAGAGACCAATGATTTTTCATTAAAAAGGCAGGGATTTGTTATAAGTATGGG
TCGTATTCTGTGCGACGGGTGTACCTCGGCTAGAATTTCTCCCCATGACACCAG
```

FIG. 20

Nucleotide sequence of truncated ORF2 (SEQ ID NO:18)

```
  1  GTGGCCGAAC AAGTTAAATT GAGCGTGGAG TTGATAGCGT GCAGTTCTTT
 51  TACTCCACCC GCTGATGTTG AGTGGTCAAC TGATGTTGAG GGCGCGGAAG
101  CACTCGTCGA GTTTGCGGGT CGTGCCTGCT ACGAAACTTT TGATAAGCCG
151  AACCCTCGAA CTGCTTCCAA TGCTGCGTAT CTGCGCCACA TCATGGAAGT
201  GGGGCACACT GCTTTGCTTG AGCATGCCAA TGCCACGATG TATATCCGAG
251  GCATTTCTCG GTCCGCGACC CATGAATTGG TCCGACACCG CCATTTTTCC
301  TTCTCTCAAC TGTCTCAGCG TTTCGTGCAC AGCGGAGAAT CGGAAGTAGT
351  GGTGCCCACT CTCAT
```

FIG. 23

Truncated ORF2 amino acid sequence (SEQ ID NO:19)

```
    GTGGCCGAACAAGTTAAATTGAGCGTGGAGTTGATAGCGTGCAGTTCTTTTACTCCACCC
1   ---------+---------+---------+---------+---------+---------+ 60

M  A  E  Q  V  K  L  S  V  E  L  I  A  C  S  S  F  T  P  P

GCTGATGTTGAGTGGTCAACTGATGTTGAGGGCGCGGAAGCACTCGTCGAGTTTGCGGGT
61  ---------+---------+---------+---------+---------+---------+ 120

A  D  V  E  W  S  T  D  V  E  G  A  E  A  L  V  E  F  A  G

CGTGCCTGCTACGAAACTTTTGATAAGCCGAACCCTCGAACTGCTTCCAATGCTGCGTAT
121 ---------+---------+---------+---------+---------+---------+ 180

R  A  C  Y  E  T  F  D  K  P  N  P  R  T  A  S  N  A  A  Y

CTGCGCCACATCATGGAAGTGGGGCACACTGCTTTGCTTGAGCATGCCAATGCCACGATG
181 ---------+---------+---------+---------+---------+---------+ 240

L  R  H  I  M  E  V  G  H  T  A  L  L  E  H  A  N  A  T  M

TATATCCGAGGCATTTCTCGGTCCGCGACCCATGAATTGGTCCGACACCGCCATTTTTCC
241 ---------+---------+---------+---------+---------+---------+ 300

Y  I  R  G  I  S  R  S  A  T  H  E  L  V  R  H  R  H  F  S

TTCTCTCAACTGTCTCAGCGTTTCGTGCACAGCGGAGAATCGGAAGTAGTGGTGCCCACT
301 ---------+---------+---------+---------+---------+---------+ 360

F  S  Q  L  S  Q  R  F  V  H  S  G  E  S  E  V  V  V  P  T

CTCAT ...
361 -----

Sequence of truncated LysA ('LysA) (NRRL-B11474) (SEQ ID NO:20)

```
ATGGCTACAGTTGAAAATTTCAATGAACTTCCCGCACACGTATGGCCACGCAATGCAGTG
CGCCAAGAAGACGGCGTTGTCACCGTCGCTGGTGTGCCTCTGCCTGACCTCGCTGAAGAA
TACGGAACCCCACTGTTCGTAGTCGACGAGGACGATTTCCGTTCCCGCTGTCGCGACATG
GCTACCGCATTCGGTGGACCAGGCAATGTGCACTACGCATCCAAAGCGTTCCTGACCAAG
ACCATTGCACGTTGGGTTGATGAAGAGGGGCTGGCACTGGACATTGCGTCCATCAATGAA
CTGGGCATTGCCCTGGCCGCTGGTTTCCCGGCCAGCCGTATCACCGCGCACGGCAACAAC
AAAGGCGTAGAGTTCCTGCGCGCGTTGGTTCAAAACGGTGTCGGGCATGTGGTGCTGGAC
TCCGCGCAGGAATTGGAACTGCTGGATTACGTTGCCGCTGGTGAAGGCAAGATCCAGGAC
GTGTTGATCCGCGTGAAGCCAGGTATCGAAGCCCACACCCACGAGTTCATCGCCACTAGC
CACGAAGACCAGAAGTTCGGATTCTCCCTGGCATCCGGTTCCGCATTCGAAGCAGCGAAA
GCAGCCAACAATGCAGAGAACTTGAACCTGGTTGGTCTGCACTGCCATGTTGGTTCCCAG
GTGTTCGACGCCGAAGGCTTCAAGCTGGCAGCAGAGCGCGTGTTGGGCCTGTACTCACAG
ATCCACAGCGAACTAGGTGTCGCCCTTCCTGAGCTGGACCTCGGTGGCGGATACGGCATC
GCCTACACTGCAGATGAGGAACCACTCAACGTCGCAGAAGTCGCCTCCGACCT
```

FIG. 25

Truncated sequence of LysA (NRRL-B11474)

DIAMINOPIMELATE DECARBOXYLASE (LysA) (SEQ ID NO:21)

MATVENFNELPAHVWPRNAVRQEDGVVTVAGVPLPDLAEEYGTPLFVVDEDDFRSRCRDM
ATAFGGPGNVHYASKAFLTKTIARWVDEEGLALDIASINELGIALAAGFPASRITAHGNN
KGVEFLRALVQNGVGHVVLDSAQELELLDYVAAGEGKIQDVLIRVKPGIEAHTHEFIATS
HEDQKFGFSLASGSAFEAAKAANNAENLNLVGLHCHVGSQVFDAEGFKLAAERVLGLYSQ
IHSELGVALPELDLGGGYGIAYTADEEPLNVAEVASDL

FIG. 26

INCREASED LYSINE PRODUCTION BY GENE AMPLIFICATION USING CORYNEFORM BACTERIA

CROSS-REFERENCE TO RELATED APPLICATIONS

The present application claims benefit to the filing dates of U.S. Provisional Application No. 60/184,130, filed Feb. 22, 2000; and U.S. Provisional Application No. 60/173,707, filed Dec. 30, 1999, each of which is herein incorporated by reference.

BACKGROUND OF THE INVENTION

1. Field of the Invention

The invention relates to the areas of microbial genetics and recombinant DNA technology. The invention provides gene sequences, vectors, microorganisms, promoters and regulatory proteins useful for the production of L-lysine. The invention further provides a method to increase the production of L-lysine.

2. Related Art

L-lysine is an important economic product obtained principally by industrial-scale fermentation utilizing the Gram positive *Corynebacterium glutamicum*, *Brevibacterium flavum* and *Brevibacterium lactofermentum* (Kleemann, A., et. al., Amino Acids, in ULLMANN's ENCYCLOPEDIA OF INDUSTRIAL CHEMISTRY, vol. A2, pp.57–97, Weinham: VCH-Verlagsgesellschaft (1985)).

The stereospecificity of the amino acids produced by fermentation makes the process advantageous compared with synthetic processes; generally L-form amino acids are produced by the microbial fermentation process. The production of L-lysine and other amino acids through fermentation, utilizing cheap carbon sources such as molasses, glucose, acetic acid and ethanol, is a relatively inexpensive means of production.

Microorganisms employed in microbial processes for amino acid production may be divided into 4 classes: wild-type strain, auxotrophic mutant, regulatory mutant and auxotrophic regulatory mutant (K. Nakayama et al., in NUTRITIONAL IMPROVEMENT OF FOOD AND FEED PROTEINS, M. Friedman, ed., (1978), pp. 649–661).

Several fermentation processes utilizing various strains isolated for auxotrophic or resistance properties are known in the art for the production of L-lysine: U.S. Pat. No. 2,979,439 discloses mutants requiring amino acid supplementation (homoserine, or L-methionine and L-threonine); U.S. Pat. No. 3,700,557 discloses mutants having a nutritional requirement for L-threonine, L-methionine, L-arginine, L-histidine, L-leucine, L-isoleucine, L-phenylalanine, L-cystine, or L-cysteine; U.S. Pat. No. 3,707,441 discloses a mutant having a resistance to an L-lysine analog; U.S. Pat. No. 3,687,810 discloses a mutant having both an ability to produce L-lysine and a resistance to bacitracin, penicillin G or polymyxin; U.S. Pat. No. 3,708,395 discloses mutants having a nutritional requirement for homoserine, L-threonine, L-threonine and L-methionine, L-leucine, L-isoleucine or mixtures thereof and a resistance to L-lysine, L-threonine, L-isoleucine or analogs thereof, U.S. Pat. No. 3,825,472 discloses a mutant having a resistance to an L-lysine analog; U.S. Pat. No. 4,169,763 discloses mutant strains of Corynebacterium that produce L-lysine and are resistant to at least one of aspartic analogs and sulfa drugs; U.S. Pat. No. 5,846,790 discloses a mutant strain able to produce L-glutamic acid and L-lysine in the absence of any biotin action-suppressing agent; and U.S. Pat. No. 5,650,304 discloses a strain belonging to the genus Corynebacterium or Brevibacterium for the production of L-lysine that is resistant to 4-N-(D-alanyl)-2,4-diamino-2,4-dideoxy-L-arabinose2,4-dideoxy-L-arabinose or a derivative thereof.

A considerable amount is known regarding the biochemical pathway for L-lysine synthesis in Corynebacterium species (recently reviewed by Sahm et al., *Ann. N. Y. Acad. Sci.* 782: 25–39 (1996)). Entry into the L-lysine pathway begins with L-aspartate (see FIG. 1), which itself is produced by transamination of oxaloacetate. A special feature of *C. glutamicum* is its ability to convert the L-lysine intermediate piperidine 2,6-dicarboxylate to diaminopimelate by two different routes, i.e. by reactions involving succinylated intermediates or by the single reaction of diaminopimelate dehydrogenase. Overall, carbon flux into the pathway is regulated at two points: first, through feedback inhibition of aspartate kinase by the levels of both L-threonine and L-lysine; and second through the control of the level of dihydrodipicolinate synthase. Therefore, increased production of L-lysine may be obtained in Corynebacterium species by deregulating and increasing the activity of these two enzymes.

More recent developments in the area of L-lysine fermentative production in Corynebacterium species involve the use of molecular biology techniques to augment L-lysine production. The following examples are provided as being exemplary of the art: U.S. Pat. Nos. 4,560,654 and 5,236,831 disclose an L-lysine producing mutant strain obtained by transforming a host Corynebacterium or Brevibacterium species microorganism which is sensitive to S-(2-aminoethyl)-cysteine with a recombinant DNA molecule wherein a DNA fragment conferring both resistance to S-(2-aminoethyl)-cysteine and L-lysine producing ability is inserted into a vector DNA; U.S. Pat. No. 5,766,925 discloses a mutant strain produced by integrating a gene coding for aspartokinase, originating from coryneform bacteria, with desensitized feedback inhibition by L-lysine and L-threonine, into chromosomal DNA of a Corynebacterium species bacterium harboring leaky type homoserine dehydrogenase or a Corynebacterium species deficient in homoserine dehydrogenase gene; increased L-lysine production is obtained by gene amplification by way of a plasmid vector or utilizing a gene replacement strategy. European Patent Applications EP 0 811 682 A2 and EP 0 854 189 A2 both provide for increased production of L-lysine in Corynebacterium species by way of gene amplification based on plasmid copy number.

SUMMARY OF THE INVENTION

It is an object of the invention to provide a method to increase the production of an amino acid in Corynebacterium species by amplifying, i.e., increasing, the number of a gene or genes of an amino acid biosynthetic pathway in a host cell. Particularly preferred Corynebacterium species include *Corynebacterium glutamicum*, *Brevibacterium flavum*, and *Brevibacterium lactofermentum*.

It is an object of the invention to provide an isolated feed back resistant aspartokinase enzyme wherein the naturally occurring threonine amino acid residue 380 in the feedback sensitive form is changed to isoleucine in the ask gene of ATCC 21529. It is an object of the invention to provide an isolated ask polypeptide comprising the amino acid sequence of SEQ ID NO:2. It is another object of the invention to provide an isolated polynucleotide molecule comprising a nucleotide sequence encoding the polypeptide sequence of SEQ ID NO:2. It is another object of the invention to provide an isolated polynucleotide molecule comprising a nucleic acid having the sequence of SEQ ID NO:1.

It is another object of the invention to provide a method comprising transforming a Corynebacterium species host cell with a polynucleotide molecule comprising a nucleotide sequence encoding a polypeptide comprising amino acid SEQ ID NO:2, wherein said isolated polynucleotide molecule is integrated into said host cell's chromosome thereby increasing the total number of said amino acid biosynthetic pathway genes in said host cell chromosome, and selecting a transformed host cell. It is a further object of the invention to provide a method comprising screening for increased amino acid production. The method may further comprise growing said transformed host cell in a medium and purifying an amino acid produced by said transformed host cell.

In another embodiment, a method to increase the production of an amino acid is a method comprising transforming a Corynebacterium species host cell with an isolated nucleic acid molecule encoding the amino acid sequence of SEQ ID NO:2, wherein said isolated nucleic acid molecule is integrated into said host cell's chromosome thereby increasing the total number of said amino acid biosynthetic pathway genes in said host cell chromosome, and wherein said isolated nucleic acid molecule further comprises at least one of the following: a polynucleotide encoding a Corynebacterium species lysine pathway asd amino acid sequence; a polynucleotide encoding a Corynebacterium species lysine pathway dapA amino acid sequence; a polynucleotide encoding a Corynebacterium species lysine pathway dapB amino acid sequence; a polynucleotide encoding a Corynebacterium species lysine pathway ddh amino acid sequence; a polynucleotide encoding a Corynebacterium species lysine pathway 'lysA amino acid sequence; a polynucleotide encoding a Corynebacterium species lysine pathway lysA amino acid sequence; a polynucleotide encoding a Corynebacterium species lysine pathway ORF2 amino acid sequence, and selecting a transformed host cell. The method may further comprise growing said transformed host cell in a medium and purifying an amino acid produced by said transformed host cell.

The term "'lysA" refers to a truncated lysA gene or amino acid sequence used by Applicants and described infra. The term "lysA" refers to the full length lysA gene or amino acid sequence used by Applicants and described infra.

It is another object of the invention to provide an isolated polynucleotide molecule comprising a nucleic acid molecule encoding the *Corynebacterium glutamicum* lysine pathway ask amino acid sequence of SEQ ID NO:2; and at least one additional Corynebacterium species lysine pathway gene selected from the group consisting of a nucleic acid molecule encoding the asd polypeptide, a nucleic acid molecule encoding the dapA polypeptide, a nucleic acid molecule encoding the dapB polypeptide, a nucleic acid molecule encoding the ddh polypeptide, a nucleic acid molecule encoding the 'lysA polypeptide, a nucleic acid molecule encoding the lysA polypeptide and a nucleic acid molecule encoding the ORF2 polypeptide. In a preferred embodiment of the invention, the isolated polynucleotide molecule comprises pK184-KDABH'L. In another preferred embodiment of the invention, the isolated nucleic acid molecule comprises pK184-KDAB. In another preferred embodiment of the invention, the isolated nucleic acid molecule comprises pD2-KDABHL. In another preferred embodiment of the invention, the isolated nucleic acid molecule comprises pD11-KDABH'L.

It is another object of the invention to provide a host cell transformed with an isolated polynucleotide molecule comprising a nucleotide sequence encoding an isolated polypeptide comprising the amino acid sequence of SEQ ID NO:2, wherein the isolated nucleic acid molecule is integrated into the host cell's chromosome thereby increasing the total number of amino acid biosynthetic pathway genes in the host cell chromosome. In one embodiment the polynucleotide further comprises at least one additional Corynebacterium species lysine pathway gene selected from the group consisting of: a nucleic acid molecule encoding an asd polypeptide; a nucleic acid molecule encoding a dapA polypeptide; a nucleic acid molecule encoding a dapB polypeptide; a nucleic acid molecule encoding a ddh polypeptide; a nucleic acid molecule encoding a 'lysA polypeptide; a nucleic acid molecule encoding a lysA polypeptide; and a nucleic acid molecule encoding an ORF2 polypeptide.

In another embodiment, the polynucleotide further comprises a nucleic acid molecule encoding a polypeptide wherein said asd polypeptide is SEQ ID NO:4; said dapA polypeptide is SEQ ID NO:6; said dapB polypeptide is SEQ ID NO:8; said ddh polypeptide is SEQ ID NO:10; said 'lysA polypeptide is SEQ ID NO:21, said lysA polypeptide is SEQ ID NO:14; and said ORF2 polypeptide is SEQ ID NO:16.

In another embodiment, the polynucleotide further comprises a nucleic acid molecule wherein said asd polypeptide is SEQ ID NO:4; said dapA polypeptide is SEQ ID NO:6; said dapB polypeptide is SEQ ID NO:8, said ddh polypeptide is SEQ ID NO:10; said 'lysA polypeptide is SEQ ID NO:21; said lysA polypeptide is SEQ ID NO:14; and said ORF2 polypeptide is SEQ ID NO:16.

In another embodiment, the polynucleotide further comprises a nucleic acid molecule encoding the asd amino acid sequence of SEQ ID NO:4; a nucleic acid molecule encoding the dapA amino acid sequence of SEQ ID NO:6; a nucleic acid molecule encoding the dapB amino acid sequence of SEQ ID NO:8; and a nucleic acid molecule encoding the ORF2 amino acid sequence of SEQ ID NO:16.

In another embodiment, the polynucleotide further comprises a nucleic acid molecule encoding the asd amino acid sequence of SEQ ID NO:4; a nucleic acid molecule encoding the dapA amino acid sequence of SEQ ID NO:6; a nucleic acid molecule encoding the dapB amino acid sequence of SEQ ID NO:8; a nucleic acid molecule encoding the ddh amino acid sequence of SEQ ID NO:10; and a nucleic acid molecule encoding the ORF2 amino acid sequence of SEQ ID NO:16.

In another embodiment, the polynucleotide further comprises a nucleic acid molecule encoding the asd amino acid sequence of SEQ ID NO:4; a nucleic acid molecule encoding the dapA amino acid sequence of SEQ ID NO:6; a nucleic acid molecule encoding the dapB amino acid sequence of SEQ ID NO:8; a nucleic acid molecule encoding the ddh amino acid sequence of SEQ ID NO:10; a nucleic acid molecule encoding the 'lysA amino acid sequence of SEQ ID NO:21; and a nucleic acid molecule encoding the ORF2 amino acid sequence of SEQ ID NO:16.

In another embodiment, the polynucleotide further comprises a nucleic acid molecule encoding the asd amino acid sequence of SEQ ID NO:4; a nucleic acid molecule encoding the dapA amino acid sequence of SEQ ID NO:6; a nucleic acid molecule encoding the dapB amino acid sequence of SEQ ID NO:8; a nucleic acid molecule encoding the ddh amino acid sequence of SEQ ID NO:10; a nucleic acid molecule encoding the lysA amino acid sequence of SEQ ID NO:14; and a nucleic acid molecule encoding the ORF2 amino acid sequence of SEQ ID NO:16.

In one embodiment, the transformed host cell is a Brevibacterium selected from the group consisting of *Brevibacterium flavum* NRRL-B30218, *Brevibacterium flavum* NRRL-B30219, *Brevibacterium lactofermentum* NRRL-B30220, *Brevibacterium lactofermentum* NRRL-B30221, *Brevibacterium lactofermentum* NRRL-B30222, *Brevibacterium flavum* NRRL-30234 and *Brevibacterium lactofermentum* NRRL-30235. In another embodiment, the host cell is *Escherichia coli* DH5 α MCR NRRL-B30228. In another embodiment, the host cell is a *C. glutamicum* selected from the group consisting of *C. glutamicum* NRRL-B30236 and *C. glutamicum* NRRL-B30237.

It is another object of the invention to provide a method of producing lysine comprising culturing the host cells comprising the amino acid sequence of SEQ ID NO:2 wherein said host cells comprise one or more of (a) increased enzyme activity of one or more lysine biosynthetic pathway enzymes compared to the genetically unaltered nonhuman host cell; (b) one or more copies of each gene encoding a lysine biosynthetic pathway enzyme; and, (c) alteration of one or more transcription factors regulating transcription of one or more genes encoding a lysine biosynthetic pathway enzyme, wherein said host cell produces lysine in said culture medium. In one embodiment of the invention, the increased enzyme activity comprises overexpressing one or more genes encoding one or more lysine biosynthetic pathway enzymes. In another embodiment of the invention the increased enzyme activity results from the activity of one or more modified lysine biosynthetic pathway enzymes wherein said enzyme modification results in a change in kinetic parameters, allosteric regulation, or both, compared to the enzyme lacking the modification. In another embodiment of the invention, alteration of one or more transcription factors comprises one or more mutations in transcription inhibitor proteins, one or more mutations in transcription activator proteins, or both, wherein said one or more mutations increases transcription of the target nucleotide sequence compared to the transcription by said one or more transcription factors lacking said alteration(s).

It is an object of the invention to provide an isolated polypeptide, wherein said polypeptide comprises an amino acid sequence having at least 95% sequence identity to the amino acid sequence of SEQ ID NO:19. It is a further object of the invention to provide an isolated polypeptide comprising the amino acid sequence of SEQ ID NO:19. It is a further object of the invention to provide an isolated polynucleotide comprising a nucleic acid having the sequence of SEQ ID NO:18. It is another object of the invention to provide host cell NRRL B30360.

It is an object of the invention to provide an isolated polypeptide wherein said polypeptide comprises a polypeptide having at least 95% sequence identity to the amino acid sequence of SEQ ID NO:21. It is a further object of the invention to provide an isolated polypeptide comprising the amino acid sequence of SEQ ID NO:21. It is a further object of the invention to provide a polynucleotide molecule comprising a nucleic acid having the sequence of SEQ ID NO:20.

It is an object of the invention to provide an isolated polynucleotide molecule comprising a nucleotide sequence encoding the polypeptide comprising the amino acid sequence of SEQ ID NO:2, further comprising a promoter sequence where said promoter sequence has at least 95% sequence identity to SEQ ID NO:17. It is a further object of the invention to provide an isolated polynucleotide molecule comprising a nucleotide sequence encoding the polypeptide comprising the amino acid sequence of SEQ ID NO:2, wherein the polynucleotide molecule further comprises the sequence of SEQ ID NO:17. It is a further object of the invention to provide a host cell NRRL B30359.

Further objects and advantages of the present invention will be clear from the description that follows.

BRIEF DESCRIPTION OF THE FIGURES

FIG. 2. The nucleotide sequence of ask (ATCC21529 sequence) (SEQ ID NO:1).

FIGS. 3A, B. The amino acid sequence of ask (ATCC 21529 sequence) (SEQ ID NOS:1–2).

FIG. 4. The nucleotide sequence of asd (ATCC 21529 sequence) (SEQ ID NO:3).

FIGS. 5A, B. The amino acid sequence of asd (ATCC 21529 sequence) (SEQ ID NOS:3–4).

FIG. 6. The nucleotide sequence of dapA (NRRL-B11474) (SEQ ID NO:5).

FIG. 7. The amino acid sequence of dapA (NRRL-B11474) (SEQ ID NOS:5–6).

FIG. 8. The nucleotide sequence of dapB (NRRL-B11474) (SEQ ID NO:7).

FIG. 9. The amino acid sequence of dapB (NRRL-B11474) (SEQ ID NOS:7–8).

FIG. 10. The nucleotide sequence of ddh (NRRL-B11474) (SEQ ID NO:9).

FIGS. 11A, B. The amino acid sequence of ddh (NRRL-B11474) (SEQ ID NOS:9–10).

FIG. 12. The nucleotide sequence of full length lysA (NRRL-B11474) (SEQ ID NO:11) used to obtain the truncated lysA ('lysA) nucleotide sequence. Underlined region annealed with lysA primer.

FIG. 13. The amino acid sequence of full length lysA (NRRL-B11474) (SEQ ID NO:12) comprising the truncated lysA ('lysA) amino acid sequence (SEQ ID NO:21). Underlined L: the last amino acid residue of lysA encoded in the truncated PCR product.

FIG. 14. The nucleotide sequence of full length lysA (pRS6) (SEQ ID NO:13).

FIGS. 15A, B, C. The amino acid sequence of full length lysA (pRS6) (SEQ ID NOS:13–14).

FIG. 16. The nucleotide sequence of ORF2 (NRRL-B11474) (SEQ ID NO:15).

FIG. 17. The amino acid sequence of ORF2 (NRRL-B11474) (SEQ ID NOS:15–16).

FIG. 19. Comparison of the aspartokinase (ask) amino acid sequence from ATCC13032, N13 and ATCC21529. A consensus sequence of the alignment is depicted and alterations in the coding sequences are shown.

FIG. 20. The nucleotide sequence of the HpaI-PvuII fragment from pRS6 (SEQ ID NO:17) comprising the P1 promoter.

FIG. 23. The nucleotide sequence of truncated ORF2 (SEQ ID NO:18).

FIG. 24. The amino acid sequence of truncated ORF2 (SEQ ID NOS:18–19).

FIG. 25. The nucleotide sequence of truncated LysA ('lysA)(NRRL-B11474) (SEQ ID NO:20).

FIG. 26. The amino acid sequence of truncated LysA ('LysA)(NRRL-B11474) (SEQ ID NO:21). Underlined L: the last amino acid residue of lysA encoded in the truncated product.

DETAILED DESCRIPTION OF THE PREFERRED EMBODIMENTS

A. Definitions

Figure 1:
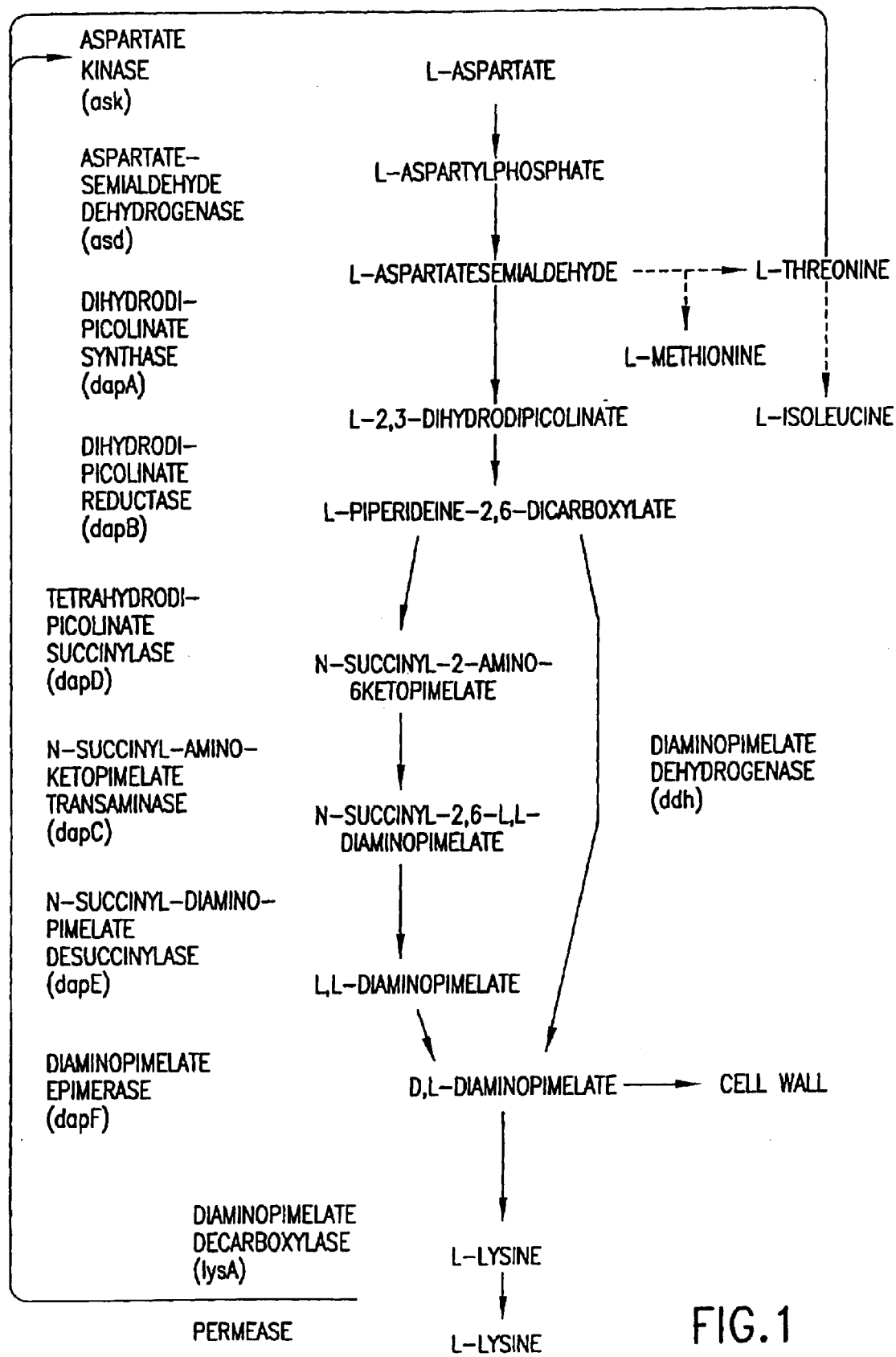
FIG. 1. A schematic of the L-lysine biosynthetic pathway in *Corynebacterium glutamicum* (Sahm et al., *Ann. N. Y. Acad. Sci.* 782: 25–39 (1996)).

In order to provide a clear and consistent understanding of the specification and claims, including the scope to be given such terms, the following definitions are provided. It is also to be noted that the term "a" or "an" entity, refers to one or more of that entity, for example, "a polynucleotide," is understood to represent one or more polynucleotides.

Allosteric Regulation. As used herein, the term refers to regulation of enzyme activity through the binding of one or more ligands (allosteric effectors) to one or more binding sites. The ligands may be the same molecule or different molecules. The molecules bind to sites on the enzyme other than the enzyme active site. As a result of the binding, a conformational change is induced in the enzyme which regulates affinity of the active site for its substrate or other ligands. Allosteric effectors may serve to enhance catalytic site substrate affinity (allosteric activators) or to reduce affinity (allosteric repressors). Allosteric effectors form the basis of metabolic control mechanisms such as feedback loops, for example (See, Copeland, Robert A., in *Enzymes. A Practical Introduction to Structure, Mechanism, and Data Analysis*, pages 279–296, Wiley-VCH, New York (1996)).

Amino Acid Biosynthetic Pathway Genes. As used herein, the term "amino acid biosynthetic pathway gene(s)" is meant to include those genes and genes fragments encoding peptides, polypeptides, proteins, and enzymes, which are directly involved in the synthesis of amino acids. These genes may be identical to those which naturally occur within a host cell and are involved in the synthesis of any amino acid, and particularly lysine, within that host cell. Alternatively, there may be modifications or mutations of such genes, for example, the genes may contain modifications or mutations which do not significantly affect the biological activity of the encoded protein. For example, the natural gene may be modified by mutagenesis or by introducing or substituting one or more nucleotides or by removing nonessential regions of the gene. Such modifications are readily performed by standard techniques.

Auxotroph. As used herein, the term refers to a strain of microorganism requiring for growth an external source of a specific metabolite that cannot be synthesized because of an acquired genetic defect.

Amino Acid Supplement. As used herein, the term refers to an amino acid required for growth and added to minimal media to support auxotroph growth.

Chromosomal Integration. As used herein, the term refers to the insertion of an exogenous DNA fragment into the chromosome of a host organism; more particularly, the term is used to refer to homologous recombination between an exogenous DNA fragment and the appropriate region of the host cell chromosome.

Enhancers. As used herein, the term refers to a DNA sequence which can stimulate promoter activity and may be an endogenous element or a heterologous element inserted to enhance the level, i.e., strength of a promoter.

High Yield Derivative. As used herein, the term refers to strain of microorganism that produces a higher yield from dextrose of a specific amino acid when compared with the parental strain from which it is derived.

Host Cell. As used herein, the term "host cell" is intended to be interchangeable with the term "microorganism." Where a difference is intended, the difference will be made clear.

Isolated Nucleic Acid Molecule. As used herein, the term is intended to mean a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Lysine Biosynthetic Pathway Protein. As used herein, the term "lysine biosynthetic pathway protein" is meant to include those peptides, polypeptides, proteins, and enzymes, which are directly involved in the synthesis of lysine from aspartate. Also included are amino acid sequences as encoded by open reading frames (ORF), where the ORF is associated with a lysine biosynthetic pathway operon. These proteins may be identical to those which naturally occur within a host cell and are involved in the synthesis of lysine within that host cell. Alternatively, there may be modifications or mutations of such proteins, for example, the proteins may contain modifications or mutations which do not significantly affect the biological activity of the protein. For example, the natural protein may be modified by mutagenesis or by introducing or substituting one or more amino acids, preferably by conservative amino acid substitution, or by removing nonessential regions of the protein. Such modifications are readily performed by standard techniques. Alternatively, lysine biosynthetic proteins may be heterologous to the particular host cell. Such proteins may be from any organism having genes encoding proteins having the same, or similar, biosynthetic roles.

Mutagenesis. As used herein, the term refers to a process whereby a mutation is generated in DNA. With "random" mutagenesis, the exact site of mutation is not predictable, occurring anywhere in the genome of the microorganism, and the mutation is brought about as a result of physical damage caused by agents such as radiation or chemical treatment. rDNA mutagenesis is directed to a cloned DNA of interest, and it may be random or site-directed.

Mutation. As used herein, the term refers to a one or more base pair change, insertion or deletion, or a combination thereof, in the nucleotide sequence of interest.

Operably Linked. As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary, join two protein coding regions, contiguous and in reading frame. However, since enhancers generally function when separated from the promoter by several kilobases and intronic sequences may be of variable lengths, some polynucleotide elements may be operably linked but not contiguous.

Operon. As used herein, the term refers to a contiguous portion of a transcriptional complex in which two or more open reading frames encoding polypeptides are transcribed as a multi-cistronic messenger RNA, controlled by a cis-acting promoter and other cis-acting sequences necessary for efficient transcription, as well as additional cis acting sequences important for efficient transcription and translation (e.g., mRNA stability controlling regions and transcription termination regions). The term generally also refers to a unit of gene expression and regulation, including the structural genes and regulatory elements in DNA.

Parental Strain. As used herein, the term refers to a strain of host cell subjected to some form of treatment to yield the host cell of the invention.

Percent Yield From Dextrose. As used herein, the term refers to the yield of amino acid from dextrose defined by the formula [(g amino acid produced/g dextrose consumed) *100]=% Yield.

Phenotype. As used herein, the term refers to observable physical characteristics dependent upon the genetic constitution of a host cell.

Promoter. As used herein, the term "promoter" has its art-recognized meaning, denoting a portion of a gene containing DNA sequences that provide for the binding of RNA polymerase and initiation of transcription and thus refers to a DNA sequence capable of controlling the expression of a coding sequence or functional RNA. Promoter sequences are commonly, but not always, found in the 5' non-coding regions of genes. In general, a coding sequence is located 3' to a promoter sequence. Sequence elements within promoters that function in the initiation of transcription are often characterized by consensus nucleotide sequences. The promoter sequence consists of proximal and more distal upstream elements (enhancers). As used herein, the term "endogenous promoter" refers to a promoter sequence which is a naturally occurring promoter sequence in that host microorganism. The term "heterologous promoter" refers to a promoter sequence which is a non-naturally occurring promoter sequence in that host microorganism. The heterologous occurring promoter sequence may be from any prokaryotic or eukaryotic organism. A synthetic promoter is a nucleotide sequence, having promoter activity, and not found naturally occurring in nature.

Promoters may be derived in their entirety from a native gene, or be hybrid promoters. Hybrid promoters are composed of different elements derived from different promoters found in nature, or even comprise synthetic DNA segments. Hybrid promoters may be constitutive, inducible or environmentally responsive.

Useful promoters include constitutive and inducible promoters. Many such promoter sequences are known in the art. See, for example, U.S. Pat. Nos. 4,980,285; 5,631,150; 5,707,928; 5,759,828; 5,888,783; 5,919,670, and, Sambrook, et al., *Molecular Cloning: A Laboratory Manual*, 2nd Ed., Cold Spring Harbor Press (1989). Other useful promoters include promoters which are neither constitutive nor responsive to a specific (or known) inducer molecule. Such promoters may include those that respond to developmental cues (such as growth phase of the culture), or environmental cues (such as pH, osmoticum, heat, or cell density, for example).

Examples of environmental conditions that may effect transcription by inducible promoters include anaerobic conditions, elevated temperature, or the presence of light. It is understood by those skilled in the art that different promoters may direct the expression of a gene in different cell types, or in response to different environmental conditions. Promoters which cause a gene to be expressed in most cell types at most times are commonly referred to as "constitutive promoters." It is further recognized that since in most cases the exact boundaries of regulatory sequences have not been completely defined, DNA fragments of different lengths may have identical or similar promoter activity.

Relative Growth. As used herein, the term refers to a measurement providing an assessment of growth by directly comparing growth of a parental strain with that of a progeny strain over a defined time period and with a defined medium.

Transcription factor. As used herein, the term "transcription factor" refers to RNA polymerases, and other proteins that interact with DNA in a sequence-specific manner and exert transcriptional regulatory effects. Transcriptional factors may be transcription inhibitory proteins or transcription activator proteins. In the context of the present invention, binding sites for transcription factors (or transcription complexes) are often included in the transcriptional regulatory element(s).

Transcription factor recognition site. As used herein, a "transcription factor recognition site" and a "transcription factor binding site" refer to a polynucleotide sequence(s) or sequence motif(s) which are identified as being sites for the sequence-specific interaction of one or more transcription factors, frequently taking the form of direct protein-DNA binding. Typically, transcription factor binding sites can be identified by DNA footprinting, gel mobility shift assays, and the like, and/or can be predicted on the basis of known consensus sequence motifs, or by other methods known to those of skill in the art.

Transcriptional Complex. As used herein, the term "transcriptional unit" or "transcriptional complex" refers to a polynucleotide sequence that comprises a structural gene (one or more exons), a cis-acting linked promoter and one or more other cis-acting sequences necessary for efficient transcription of the structural sequences, distal regulatory elements necessary for appropriate transcription of the structural sequences, and additional cis sequences important for efficient transcription and translation (e.g., polyadenylation site, mRNA stability controlling sequences). See, for example U.S. Pat. No. 6,057,299.

Transcriptional Regulatory Element. As used herein, the term "transcriptional regulatory element" refers to a DNA sequence which activates transcription alone or in combination with one or more other DNA sequences. A transcriptional regulatory element can, for example, comprise a promoter, response element, negative regulatory element, silencer element, gene suppressor, and/or enhancer. See, for example, U.S. Pat. No. 6,057,299.

B. Microbiological and Recombinant DNA Methodologies

The invention as provided herein utilizes some methods and techniques that are known to those skilled in the arts of microbiology and recombinant DNA technologies. Methods and techniques for the growth of bacterial cells, the introduction of isolated DNA molecules into host cells, and the isolation, cloning and sequencing of isolated nucleic acid molecules, etc., are a few examples of such methods and techniques. These methods and techniques are described in many standard laboratory manuals, such as Davis et al., *Basic Methods In Molecular Biology* (1986), J. H. Miller, *Experiments in Molecular Genetics*, Cold Spring Harbor Laboratory Press, Cold Spring Harbor, N.Y. (1972); J. H. Miller, *A Short Course in Bacterial Genetics*, Cold Spring Harbor Laboratory Press, Cold Spring Harbor, N.Y. (1992); M. Singer and P. Berg, *Genes & Genomes*, University Science Books, Mill Valley, Calif. (1991); J. Sambrook, E. F. Fritsch and T. Maniatis, *Molecular Cloning: A Laboratory Manual*, 2d ed., Cold Spring Harbor Laboratory Press, Cold Spring Harbor, N.Y. (1989); P. B. Kaufman et al., *Handbook of Molecular and Cellular Methods in Biology and Medicine*, CRC Press, Boca Raton, Fla. (1995); *Methods in Plant Molecular Biology and Biotechnology*, B. R. Glick and J. E. Thompson, eds., CRC Press, Boca Raton, Fla. (1993); and P. F. Smith-Keary, *Molecular Genetics of Escherichia coli*, The Guilford Press, New York, N.Y. (1989), all of which are incorporated herein by reference in their entireties.

Unless otherwise indicated, all nucleotide sequences newly described herein were determined using an automated DNA sequencer (such as the Model 373 from Applied Biosystems, Inc.). Therefore, as is known in the art, for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art.

In certain embodiments, polynucleotides of the invention comprise a nucleic acid, the sequence of which is at least 90%, 91%, 92%, 93%, 94%, 95%, 96%, 97%, 98% or 99% identical to a sequence selected from the group consisting of SEQ ID NO:17, SEQ ID NO:18, and SEQ ID NO:20, or a complementary sequence thereof.

By a polynucleotide comprising a nucleic acid, the sequence of which is at least, for example, 95% "identical" to a reference nucleotide sequence is intended that the nucleic acid sequence is identical to the reference sequence except that the nucleic acid sequence may include up to five mismatches per each 100 nucleotides of the reference nucleic acid sequence. In other words, to obtain a nucleic acid, the sequence of which is at least 95% identical to a reference nucleic acid sequence, up to 5% of the nucleotides in the reference sequence may be deleted or substituted with another nucleotide, or a number of nucleotides up to 5% of the total nucleotides in the reference sequence may be inserted into the reference sequence. The reference (query) sequence may be any one of the entire nucleotide sequences shown in SEQ ID NO:17, SEQ ID NO:18, or SEQ ID NO:20, or any fragment of any of these sequences, as described infra.

As a practical matter, whether any particular nucleic acid sequence is at least 90%, 91%, 92%, 93%, 94%, 95%, 96%, 97%, 98% or 99% identical to, for instance, a nucleotide sequence consisting of SEQ ID NO:17; SEQ ID NO.:18, or SEQ ID NO:20, or a complementary sequence thereof, can be determined conventionally using sequence analysis computer programs such as a OMIGA® Version 2.0 for Windows, available from Oxford Molecular, Ltd. (Oxford, U.K.). OMIGA uses the CLUSTAL W alignment algorithm using the slow fall dynamic programming alignment method with default parameters of an open gap penalty of 10 and an extend gap penalty of 5.0, to find the best alignment between two nucleotide sequences. When using CLUSTAL W or any other sequence alignment program to determine whether a particular sequence is, for instance, 95% identical to a reference sequence according to the present invention, the parameters are set, of course, such that the percentage of identity is calculated over the full length of the reference nucleotide sequence such that gaps, mismatches, or insertions of up to 5% of the total number of nucleotides in the reference sequence are allowed. Other sequence analysis programs, known in the art, can be used in the practice of the invention.

This embodiment of the present invention is directed to polynucleotides comprising a nucleic acid, the sequence of which is at least 90%, 91%, 92%, 93%, 94%, 95%, 96%, 97%, 98% or 99% identical to a nucleic acid sequence of SEQ ID NO:17, SEQ ID NO:18, and SEQ ID NO:20, or a complementary sequence thereof, irrespective of whether they have functional activity. This is because even where a particular polynucleotide does not have functional activity, one of skill in the art would still know how to use the nucleic acid molecule, for instance, as a hybridization probe, an S1 nuclease mapping probe, or a polymerase chain reaction (PCR) primer.

Preferred, however, are polynucleotides comprising a nucleic acid, the sequence of which is at least 90%, 91%, 92%, 93%, 94%, 95%, 96%, 97%, 98% or 99% identical to a nucleic acid sequence of SEQ ID NO:17, SEQ ID NO:18 or SEQ ID NO:20, or a complementary sequence thereof, which do, in fact, have functional activity in Corynebacterium species.

By a polypeptide having an amino acid sequence at least, for example, 95% "identical" to a reference amino acid sequence of a polypeptide is intended that the amino acid sequence of the claimed polypeptide is identical to the reference sequence except that the claimed polypeptide sequence may include up to five amino acid alterations per each 100 amino acids of the reference amino acid of the polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 92%, 95%, 96%, 97%, 98% or 99% identical to, for instance, the amino acid sequence shown in SEQ ID NO:2 or to the amino acid sequence encoded by a nucleic acid sequence can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference sequence (query sequence, a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

C. Methods and Processes of the Invention

Various embodiments of the invention provide methods to increase the production of an amino acid and processes for the production of an amino acid from a Corynebacterium species host cell. Particularly preferred Corynebacterium species of the methods and processes of the invention include: Corynebacterium glutamicum, Brevibacterium flavum, Brevibacterium lactofermentum and other Corynebacteria and Brevibacteria species known in the art.

As will be understood by those skilled in the art, the term "Corynebacterium species" includes those organisms previously identified in the literature as "Brevibacterium species," for example Brevibacterium flavum and Brevibacterium lactofermentum which have now been reclassified into the genus Corynebacterium (Int. J. Syst. Bacteriol. 41: 255 (1981)).

Amino acid biosynthetic pathway genes embodied by the methods and processes described herein include those for L-glycine, L-alanine, L-methionine, L-phenylalanine, L-tryptophan, L-proline, L-serine, L-threonine, L-cysteine, L-tyrosine, L-asparagine, L-glutamine, L-aspartic acid, L-glutamic acid, L-lysine, L-arginine, L-histidine, L-isoleucine, L-leucine, and L-valine biosynthesis. Particularly preferred embodiments are drawn to biosynthetic pathway genes for L-lysine (Sahm et al., Ann. N. Y. Acad. Sci. 782: 25–39 (1996)), L-threonine, L-isoleucine, L-tryptophan, and L-valine.

By way of example, the amino acid pathway for L-lysine biosynthesis is well known to skilled artisans of amino acid production in Corynebacterium species. Genes encoding the enzymes important for the conversion of L-aspartate to L-lysine include the ask, asd, dapA, dapB, ddh and lysA genes (FIG. 1). Thus, the invention provides herein for exemplary purposes only, specific embodiments utilizing L-lysine biosynthetic pathway genes. Other embodiments drawn to the use of biosynthetic pathway genes for the synthesis of other amino acids are also encompassed by the invention described herein.

The methods to increase the production of an amino acid and the processes for the production of an amino acid of the invention both utilize a step requiring the transformation of an isolated nucleic acid molecule into a Corynebacterium species host cell. As known to one skilled in the art, transformation of an isolated nucleic acid molecule into a host cell may be effected by electroporation, transduction or other methods. These methods are described in the many standard laboratory manuals referenced and incorporated herein.

The methods to increase the production of an amino acid and the processes for the production of an amino acid of the invention both utilize a step requiring amplification of at least one amino acid biosynthesis pathway gene. As known to one skilled in the art, the term amplification means increasing the number of a gene or genes of an amino acid biosynthetic pathway by any means known in the art. Particularly preferred means of amplification include: (1) the addition an isolated nucleic acid molecule comprising copies of a gene or genes of a biosynthetic pathway by insertion into the chromosome of a host cell, for example by homologous recombination, and (2) the addition an isolated nucleic acid molecule comprising copies of a gene or genes of a biosynthetic pathway into a host cell by way of a self-replicating, extra-chromosomal vector, for example, a plasmid.

Another method of the invention to increase the production of an amino acid comprises increasing the expression of at least one amino acid biosynthetic pathway gene. Preferred methods of increasing expression comprise using heterologous promoters, regulated promoters, unregulated promoters and combinations thereof.

Methods of inserting an isolated nucleic acid molecule into the chromosome of a host cell are known to those skilled in the art. For example, insertion of isolated nucleic acid molecules into the chromosome of Corynebacterium species may be done utilizing the pK184 plasmid described by Jobling, M. et al., *Nucleic Acids Research* 18(17): 5315–5316 (submitted 1990). Because these vectors lack a Corynebacterium species origin of replication and contain a selectable marker such as kanamycin (kan), cells will only be capable of growing under selection if the vector has been inserted into the host cell chromosome by homologous recombination.

In alternative embodiments, the invention also provides methods for increasing amino acid production and processes for the production of an amino acid wherein biosynthetic pathway gene amplification is accomplished through the introduction into a host cell of a self-replicating, extra-chromosomal vector, e.g., a plasmid, comprising an isolated nucleic acid molecule encoding an amino acid biosynthetic pathway gene or genes. Suitable plasmids for these embodiments include pSR1 and other derivatives of pSR1 (Archer, J. et al., *J. Gen. Microbiol.* 139: 1753–1759 (1993)).

For various embodiments of the invention drawn to a method to increase production of an amino acid, screening for increased production of an amino acid, for example L-lysine, may be determined by directly comparing the amount of L-lysine produced in culture by a Corynebacterium species host strain to that of a Corynebacterium species transformed host strain in which an amino acid biosynthesis gene or genes are amplified. The level of production of the amino acid of choice may conveniently be determined by the following formula to calculate the percent yield from dextrose: [(g amino acid/L/(g dextrose consumed/L)]*100.

In one embodiment, the invention provides a method to increase the production of an amino acid comprising: (a) transforming a Corynebacterium species host cell with an isolated polynucleotide molecule comprising a nucleotide sequence encoding a polypeptide comprising the amino acid sequence of SEQ ID NO:2; (b) amplifying the number of at least one of the biosynthetic pathway genes for said amino acid in the chromosome of said host cell; (c) selecting a transformed host cell; and (d) screening for increased production of said amino acid from said transformed host cell relative to said host cell.

In a particularly preferred embodiment, the invention provides a method to increase the production of an amino acid comprising transforming a Corynebacterium species host cell with an isolated polynucleotide molecule comprising a nucleotide sequence encoding a polypeptide comprising the amino acid sequence of SEQ ID NO:2; and further comprising at least one of the following: a nucleic acid molecule encoding a Corynebacterium species lysine pathway asd amino acid sequence; a nucleic acid molecule encoding a Corynebacterium species lysine pathway dapA amino acid sequence; a nucleic acid molecule encoding a Corynebacterium species lysine pathway dapB amino acid sequence; a nucleic acid molecule encoding a Corynebacterium species lysine pathway ddh amino acid sequence; a nucleic acid molecule encoding a Corynebacterium species lysine pathway 'lysA amino acid sequence; a nucleic acid molecule encoding a Corynebacterium species lysine pathway lysA amino acid sequence; and a nucleic acid molecule encoding a Corynebacterium species lysine pathway ORF2 amino acid sequence.

In another particular embodiment of the method, the isolated polynucleotide molecule further comprises at least one of the following: a nucleic acid molecule encoding the asd amino acid sequence of SEQ ID NO:4; a nucleic acid molecule encoding the dapA amino acid sequence of SEQ ID NO:6; a nucleic acid molecule encoding the dapB amino acid sequence of SEQ ID NO:8; a nucleic acid molecule encoding the ddh amino acid sequence of SEQ ID NO:10; a nucleic acid molecule encoding the 'lysA amino acid sequence of SEQ ID NO:21; a nucleic acid molecule encoding the lysA amino acid sequence of SEQ ID NO:14; and a nucleic acid molecule encoding the ORF2 amino acid sequence of SEQ ID NO:16.

In another particular embodiment of the method, the isolated polynucleotide molecule further comprises the following: a nucleic acid molecule encoding the asd amino acid sequence of SEQ ID NO:4; a nucleic acid molecule encoding the dapA amino acid sequence of SEQ ID NO:6; a nucleic acid molecule encoding the dapB amino acid sequence of SEQ ID NO:8; and a nucleic acid molecule encoding the ORF2 amino acid sequence of SEQ ID NO:16.

In another particular embodiment of the method, the isolated polynucleotide molecule further comprises the following: a nucleic acid molecule encoding the asd amino acid sequence of SEQ ID NO:4; a nucleic acid molecule encoding the dapA amino acid sequence of SEQ ID NO:6; a nucleic acid molecule encoding the dapB amino acid sequence of SEQ ID NO:8; a nucleic acid molecule encoding the ddh amino acid sequence of SEQ ID NO:10, and a nucleic acid molecule encoding the ORF2 amino acid sequence of SEQ ID NO:16.

In another particular embodiment of the method, the isolated polynucleotide molecule further comprises the following: a nucleic acid molecule encoding the asd amino acid sequence of SEQ ID NO:4; a nucleic acid molecule encoding the dapA amino acid sequence of SEQ ID NO:6; a nucleic acid molecule encoding the dapB amino acid sequence of SEQ ID NO:8; a nucleic acid molecule encoding the ddh amino acid sequence of SEQ ID NO:10; a nucleic acid molecule encoding the 'lysA amino acid sequence of SEQ ID NO:21; and a nucleic acid molecule encoding the ORF2 amino acid sequence of SEQ ID NO:16.

In another particular embodiment of the method, the polynucleotide molecule further comprises the following: a nucleic acid molecule encoding the asd amino acid sequence of SEQ ID NO:4; a nucleic acid molecule encoding the dapA amino acid sequence of SEQ ID NO:6; a nucleic acid molecule encoding the dapB amino acid sequence of SEQ ID NO:8; a nucleic acid molecule encoding the ddh amino acid sequence of SEQ ID NO:10; a nucleic acid molecule encoding the lysA amino acid sequence of SEQ ID NO:14; and a nucleic acid molecule encoding the ORF2 amino acid sequence of SEQ ID NO:16.

In another embodiment of the method, the method further comprises growing said transformed host cell in a medium; and purifying an amino acid produced by said transformed host cell.

It is another object of the invention to provide an isolated polynucleotide molecule comprising the polynucleotide molecule comprising a nucleotide sequence encoding the polypeptide comprising the amino acid sequence of SEQ ID NO:2; and at least one additional Corynebacterium species lysine pathway gene selected from the group consisting of a nucleic acid molecule encoding an asd polypeptide; a nucleic acid molecule encoding a dapA polypeptide; a nucleic acid molecule encoding a dapB polypeptide; a nucleic acid molecule encoding a ddh polypeptide; a nucleic acid molecule encoding a 'lysA polypeptide; a nucleic acid molecule encoding a lysA polypeptide; and a nucleic acid molecule encoding an ORF2 polypeptide. In a preferred embodiment, said asd polypeptide is SEQ ID NO:4; said dapA polypeptide is SEQ ID NO:6; said dapB polypeptide is SEQ ID NO:8; said ddh polypeptide is SEQ ID NO:10; said 'lysA polypeptide is SEQ ID NO:21; said lysA polypeptide is SEQ ID NO:14; and said ORF2 polypeptide is SEQ ID NO:16.

It is another object of the invention to provide an isolated polynucleotide molecule comprising the polynucleotide molecule comprising a nucleotide sequence encoding the polypeptide comprising the amino acid sequence of SEQ ID NO 2; a nucleic acid molecule encoding the asd amino acid sequence of SEQ ID NO:4; a nucleic acid molecule encoding the dapA amino acid sequence of SEQ ID NO:6; a nucleic acid molecule encoding the dapB amino acid sequence of SEQ ID NO:8; and a nucleic acid molecule encoding the ORF2 amino acid sequence of SEQ ID NO:16.

It is another object of the invention to provide an isolated polynucleotide molecule comprising the polynucleotide molecule comprising a nucleotide sequence encoding the polypeptide comprising the amino acid sequence of SEQ ID NO:2; a nucleic acid molecule encoding the asd amino acid sequence of SEQ ID NO:4; a nucleic acid molecule encoding the dapA amino acid sequence of SEQ ID NO:6; a nucleic acid molecule encoding the dapB amino acid sequence of SEQ ID NO:8; a nucleic acid molecule encoding the ddh amino acid sequence of SEQ ID NO:10; and a nucleic acid molecule encoding the ORF2 amino acid sequence of SEQ ID NO:16.

It is another object of the invention to provide an isolated polynucleotide molecule comprising the polynucleotide molecule comprising a nucleotide sequence encoding the polypeptide comprising the amino acid sequence of SEQ ID NO:2; a nucleic acid molecule encoding the asd amino acid sequence of SEQ ID NO:4; a nucleic acid molecule encoding the dapA amino acid sequence of SEQ ID NO:6; a nucleic acid molecule encoding the dapB amino acid sequence of SEQ ID NO:8, a nucleic acid molecule encoding the ddh amino acid sequence of SEQ ID NO:10; a nucleic acid molecule encoding the 'lysA amino acid sequence of SEQ ID NO:21; and a nucleic acid molecule encoding the ORF2 amino acid sequence of SEQ ID NO:16.

It is another object of the invention to provide an isolated polynucleotide molecule comprising the polynucleotide molecule comprising a nucleotide sequence encoding the polypeptide comprising the amino acid sequence of SEQ ID NO:2; a nucleic acid molecule encoding the asd amino acid sequence of SEQ ID NO:4; a nucleic acid molecule encoding the dapA amino acid sequence of SEQ ID NO:6; a nucleic acid molecule encoding the dapB amino acid sequence of SEQ ID NO:8; a nucleic acid molecule encoding the ddh amino acid sequence of SEQ ID NO:10; a nucleic acid molecule encoding the lysA amino acid sequence of SEQ ID NO:14; and a nucleic acid molecule encoding the ORF2 amino acid sequence of SEQ ID NO:16.

It is a further object of the invention to provide an isolated polynucleotide molecule comprising pK184-KDAB. It is a further object of the invention to provide an isolated polynucleotide molecule comprising pK184-KDABH'L. It is a further object of the invention to provide an isolated polynucleotide molecule comprising pD11-KDABH'L. It is a further object of the invention to provide an isolated polynucleotide molecule comprising pD2-KDABHL.

It is a further object of the invention to provide a vector comprising the isolated polynucleotide molecule comprising a nucleotide sequence encoding a polypeptide comprising the amino acid sequence of SEQ ID NO 2; and further comprising at least one additional Corynebacterium species lysine pathway gene selected from the group consisting of a nucleic acid molecule encoding an asd polypeptide; a nucleic acid molecule encoding a dapA polypeptide; a nucleic acid molecule encoding a dapB polypeptide; a nucleic acid molecule encoding a ddh polypeptide; a nucleic acid molecule encoding a 'lysA polypeptide; a nucleic acid molecule encoding a lysA polypeptide; and a nucleic acid molecule encoding an ORF2 polypeptide.

It is a further object to provide a host cell comprising a vector comprising the isolated polynucleotide molecule comprising a nucleotide sequence encoding a polypeptide comprising the amino acid sequence of SEQ ID NO 2; and further comprising at least one additional Corynebacterium species lysine pathway gene selected from the group consisting of a nucleic acid molecule encoding an asd polypeptide; a nucleic acid molecule encoding a dapA polypeptide; a nucleic acid molecule encoding a dapB polypeptide; a nucleic acid molecule encoding a ddh polypeptide; a nucleic acid molecule encoding a 'lysA polypeptide; a nucleic acid molecule encoding a lysA polypeptide; and a nucleic acid molecule encoding an ORF2 polypeptide.

It is a further object to provide a host cell wherein said host cell is a Brevibacterium selected from the group consisting of *Brevibacterium flavum* NRRL-B30218, *Brevibacterium flavum* NRRL-B30219, *Brevibacterium lactofermentum* NRRL-B30220, *Brevibacterium lactofermentum* NRRL-B30221, *Brevibacterium lactofermentum* NRRL-B30222, *Brevibacterium flavum* NRRL-30234 and *Brevibacterium lactofermentum* NRRL-30235. In another embodiment, the host cell is *Escherichia coli* DH5 α MCR NRRL-B30228. In another embodiment, the host cell is a *C. glutamicum* selected from the group consisting of *C. glutamicum* NRRL-B30236 and *C. glutamicum* NRRL-B30237.

The invention provides processes for the production of an amino acid. In one embodiment, the invention provides a process for producing an amino acid comprising: (a) transforming a Corynebacterium species host cell with an isolated nucleic acid molecule; (b) amplifying the number of chromosomal copies of at least one of the biosynthetic pathway genes for said amino acid; (c) selecting a transformed host cell; (d) growing said transformed cell in a medium; and (e) purifying said amino acid.

The invention is also directed to an isolated polypeptide comprising the amino acid sequence of SEQ ID NO:19. In one embodiment of the invention, the polypeptide has at least 95% sequence identity to the amino acid sequence of SEQ ID NO:19. The invention is also directed to an isolated polynucleotide molecule comprising a nucleotide sequence encoding the polypeptide of SEQ ID NO:19. In one embodiment, the isolated polynucleotide comprises a nucleic acid having the sequence of SEQ ID NO:18.

The invention is also directed to a vector comprising the polynucleotide molecule comprising a nucleotide sequence encoding the polypeptide comprising the amino acid sequence of SEQ ID NO:19. In one embodiment, the invention is directed to a host cell comprising a vector encoding a polypeptide comprising the amino acid sequence of SEQ ID NO:19. In one embodiment, the host cell is NRRL B30360.

The invention is also directed to a method comprising transforming a Corynebacterium species host cell with the polynucleotide molecule comprising a nucleotide sequence encoding a polypeptide comprising the amino acid sequence of SEQ ID NO:19, and selecting a transformed host cell. In one embodiment, the method further comprises screening for increased amino acid production. In a preferred embodiment, the amino acid screened for is lysine. In one embodiment, the polynucleotide molecule is integrated into said host cell's chromosome, thereby increasing the total number of said amino acid biosynthetic pathway genes in said host cell chromosome.

In another embodiment, the polynucleotide molecule further comprises at least one of the following: (a) a nucleic acid molecule encoding a Corynebacterium species lysine pathway ask amino acid sequence, (b) a nucleic acid molecule encoding a Corynebacterium species lysine pathway asd amino acid sequence; (c) a nucleic acid molecule encoding a Corynebacterium species lysine pathway dapA amino acid sequence; (d) a nucleic acid molecule encoding a Corynebacterium species lysine pathway dapB amino acid sequence; (e) a nucleic acid molecule encoding a Corynebacterium species lysine pathway ddh amino acid sequence; (f) a nucleic acid molecule encoding a Corynebacterium species lysine pathway 'lysA amino acid sequence; (g) a nucleic acid molecule encoding a Corynebacterium species lysine pathway lysA amino acid sequence; and, (h) a nucleic acid molecule encoding an ORF2 polypeptide having SEQ ID NO:16. In this embodiment, the method further comprises screening for increased amino acid production. In another embodiment, the amino acid screened for is lysine.

In another embodiment of the method, the polynucleotide molecule further comprises: (a) a nucleic acid molecule encoding the ask amino acid sequence having SEQ ID NO:2; (b) a nucleic acid molecule encoding a Corynebacterium species lysine pathway asd amino acid sequence; (c) a nucleic acid molecule encoding a Corynebacterium species lysine pathway dapB amino acid sequence; (d) a nucleic acid molecule encoding a Corynebacterium species lysine pathway ddh amino acid sequence; and, (e) a nucleic acid molecule encoding a Corynebacterium species lysine pathway lysA amino acid sequence. In one embodiment of this method, the method further comprises screening for increased amino acid production.

The invention is also directed to an isolated polypeptide comprising the amino acid sequence of SEQ ID NO:21. In one embodiment, the polypeptide has at least 95% sequence identity to the amino acid sequence of SEQ ID NO:21. The invention also comprises an isolated polynucleotide molecule comprising a nucleotide sequence encoding the polypeptide comprising the amino acid sequence having at least 95% sequence identity to the amino acid sequence of SEQ ID NO:21. The invention is further comprises a polynucleotide molecule comprising a nucleic acid having the sequence of SEQ ID NO:20. In one embodiment the invention comprises a vector comprising the polynucleotide molecule comprising a nucleotide sequence encoding the polypeptide comprising the amino acid sequence having at least 95% sequence identity to the amino acid sequence of SEQ ID NO:21. The invention further comprises a host cell comprising the vector comprising the polynucleotide molecule comprising a nucleotide sequence encoding the polypeptide comprising the amino acid sequence having at least 95% sequence identity to the amino acid sequence of SEQ ID NO:21.

In one embodiment, the invention comprises a host cell selected from the group consisting of NRRL B30218, NRRL B30220 and NRRL B30222.

The invention is further directed to a method comprising transforming a Corynebacterium species host cell with a polynucleotide molecule comprising a nucleotide sequence encoding the polypeptide comprising the amino acid sequence having at least 95% sequence identity to the amino acid sequence of SEQ ID NO:21, and selecting a transformed host cell. The method further comprises screening for increased amino acid production; in particular, for lysine production. In one embodiment, the polynucleotide molecule is integrated into said host cell's chromosome, thereby increasing the total number of said amino acid biosynthetic pathway genes in said host cell chromosome. In one embodiment the method further comprises a polynucleotide molecule further comprising at least one of the following: (a) a nucleic acid molecule encoding a Corynebacterium species lysine pathway ask amino acid sequence; (b) a nucleic acid molecule encoding a Corynebacterium species lysine pathway ask amino acid sequence having SEQ ID NO. 2; (c) a nucleic acid molecule encoding a Corynebacterium species lysine pathway asd amino acid sequence; (d) a nucleic acid molecule encoding a Corynebacterium species lysine pathway dapA amino acid sequence; (e) a nucleic acid molecule encoding a Corynebacterium species lysine pathway dapB amino acid sequence; (f) a nucleic acid molecule encoding a Corynebacterium species lysine pathway ddh amino acid sequence; (g) a nucleic acid molecule encoding a Corynebacterium species lysine pathway ORF2 amino acid sequence; and, (h) a nucleic acid molecule encoding a truncated Corynebacterium species lysine pathway ORF2 amino acid sequence. In one embodiment, the method further comprises screening for increased amino acid production. In another embodiment, the amino acid screened for is lysine.

Another embodiment of the invention is also directed to an isolated polynucleotide molecule comprising a nucleotide sequence encoding the polypeptide comprising the amino acid sequence of SEQ ID NO:2, wherein the polynucleotide molecule further comprises a promoter sequence having SEQ ID NO:17. In one embodiment, the promoter sequence has at least 95% sequence identity to SEQ ID NO:17. In one embodiment, the promoter sequence having at least 95% sequence identity to SEQ ID NO:17 is operably directly linked to the LysA gene. In another embodiment of the invention, there is a vector comprising the isolated polynucleotide molecule comprising a nucleotide sequence encoding the polypeptide comprising the amino acid sequence of SEQ ID NO:2, wherein the polynucleotide molecule further comprises a promoter sequence wherein said promoter sequence has at least 95% sequence identity to SEQ ID NO:17. In another aspect of the invention, there is a host cell comprising the vector comprising the isolated polynucleotide molecule comprising a nucleotide sequence encoding the polypeptide comprising the amino acid sequence of SEQ ID NO:2, wherein the polynucleotide molecule further comprises a promoter sequence having at least 95% sequence identity to SEQ ID NO:17. In one embodiment, the host cell is NRRL B30359.

The invention is also directed to a method comprising transforming a Corynebacterium species host cell with the polynucleotide molecule comprising a nucleotide sequence encoding the polypeptide comprising the amino acid sequence of SEQ ID NO:2, wherein the polynucleotide molecule further comprises a promoter sequence having at least 95% sequence identity to SEQ ID NO:17, and selecting a transformed host cell. In one embodiment, the method further comprises screening for increased amino acid production. In another embodiment, the amino acid screened for is lysine. In another embodiment of the method, the polynucleotide molecule is integrated into said host cell's chromosome, thereby increasing the total number of amino acid biosynthetic pathway genes in said host cell chromosome. In another embodiment of the method, the polynucleotide molecule further comprises at least one of the following: (a) a nucleic acid molecule encoding a Corynebacterium species lysine pathway asd amino acid sequence; (b) a nucleic acid molecule encoding a Corynebacterium species lysine pathway dapA amino acid sequence; (c) a nucleic acid molecule encoding a Corynebacterium species lysine pathway dapB amino acid sequence; (d) a nucleic acid molecule encoding a Corynebacterium species lysine pathway ddh amino acid sequence; (e) a nucleic acid molecule encoding a Corynebacterium species lysine pathway ORF2 amino acid sequence; (f) a nucleic acid molecule encoding a truncated Corynebacterium species lysine pathway ORF2 amino acid sequence; (g) a nucleic acid molecule encoding a Corynebacterium species lysine pathway lysA amino acid sequence; and, (h) a nucleic acid molecule encoding a truncated Corynebacterium species lysine pathway lysA amino acid sequence. In this embodiment, the method further comprises screening for increased amino acid production; in particular, for lysine production.

In a different embodiment of the method, the polynucleotide molecule comprises: (a) a nucleic acid molecule encoding a Corynebacterium species lysine pathway asd amino acid sequence; (b) a nucleic acid molecule encoding a Corynebacterium species lysine pathway dapA amino acid sequence; (c) a nucleic acid molecule encoding a Corynebacterium species lysine pathway dapB amino acid sequence; (d) a nucleic acid molecule encoding a Corynebacterium species lysine pathway ddh amino acid sequence; (e) a nucleic acid molecule encoding a Corynebacterium species lysine pathway ORF2 amino acid sequence; and, (f a nucleic acid molecule encoding a Corynebacterium species lysine pathway lysA amino acid sequence. In this embodiment, the method further comprises screening for increased amino acid production. In a preferred embodiment, the amino acid is lysine.

A variety of media known to those skilled in the art may be used to support cell growth for the production of an amino acid. Illustrative examples of suitable carbon sources include, but are not limited to: carbohydrates, such as glucose, fructose, sucrose, starch hydrolysate, cellulose hydrolysate and molasses; organic acids, such as acetic acid, propionic acid, formic acid, malic acid, citric acid, and fumaric acid; and alcohols, such as glycerol. Illustrative examples of suitable nitrogen sources include, but are not limited to: ammonia, including ammonia gas and aqueous ammonia; ammonium salts of inorganic or organic acids, such as ammonium chloride, ammonium phosphate, ammonium sulfate and ammonium acetate; and other nitrogen-containing sources, including meat extract, peptone, corn steep liquor, casein hydrolysate, soybean cake hydrolysate, urea and yeast extract.

A variety of fermentation techniques are known in the art which may be employed in processes of the invention drawn to the production of amino acids. Generally, amino acids may be commercially produced from the invention in fermentation processes such as the batch type or of the fed-batch type. In batch type fermentations, all nutrients are added at the beginning of the fermentation. In fed-batch or extended fed-batch type fermentations one or a number of nutrients are continuously supplied to the culture, right from the beginning of the fermentation or after the culture has reached a certain age, or when the nutrient(s) which are fed were exhausted from the culture fluid. A variant of the extended batch of fed-batch type fermentation is the repeated fed-batch or fill-and-draw fermentation, where part of the contents of the fermenter is removed at some time, for instance when the fermenter is full, while feeding of a nutrient is continued. In this way a fermentation can be extended for a longer time.

Another type of fermentation, the continuous fermentation or chemostat culture, uses continuous feeding of a complete medium, while culture fluid is continuously or semi-continuously withdrawn in such a way that the volume of the broth in the fermenter remains approximately constant. A continuous fermentation can in principle be maintained for an infinite time.

In a batch fermentation an organism grows until one of the essential nutrients in the medium becomes exhausted, or until fermentation conditions become unfavorable (e.g., the pH decreases to a value inhibitory for microbial growth). In fed-batch fermentations measures are normally taken to maintain favorable growth conditions, e.g., by using pH control, and exhaustion of one or more essential nutrients is prevented by feeding these nutrient(s) to the culture. The microorganism will continue to grow, at a growth rate dictated by the rate of nutrient feed. Generally a single nutrient, very often the carbon source, will become limiting for growth. The same principle applies for a continuous fermentation, usually one nutrient in the medium feed is limiting, all other nutrients are in excess. The limiting nutrient will be present in the culture fluid at a very low concentration, often unmeasurably low. Different types of nutrient limitation can be employed. Carbon source limitation is most often used. Other examples are limitation by the nitrogen source, limitation by oxygen, limitation by a specific nutrient such as a vitamin or an amino acid (in case the microorganism is auxotrophic for such a compound), limitation by sulphur and limitation by phosphorous.

The amino acid may be recovered by any method known in the art. Exemplary procedures are provided in the following: Van Walsem, H. J. & Thompson, M. C., *J. Biotechnol.* 59:127–132 (1997), and U.S. Pat. No. 3,565,951, both of which are incorporated herein by reference.

The invention described herein provides isolated nucleic acid molecules comprising at least one L-lysine amino acid biosynthesis gene. Unless otherwise indicated, all nucleotide sequences described herein were determined using an automated DNA sequencer (such as the Model 373 from Applied Biosystems, Inc.), and all amino acid, sequences of polypeptides encoded by DNA molecules described herein were predicted by translation of the relative DNA sequence. Therefore, as is known in the art, for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art.

As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The invention provides several isolated nucleic acid molecules encoding comprising at least one L-lysine amino acid biosynthesis pathway gene of *Corynebacterium*

*glutamicum*. More specifically, the invention provides the following isolated nucleic acid molecules: the nucleotide sequence of the ask gene from the strain ATCC 21529 (SEQ ID NO:1); the nucleotide sequence of the asd gene from the strain ATCC 21529 (SEQ ID NO:3); the nucleotide sequence of the dapA gene from the strain NRRL-B11474 (SEQ ID NO:5); the nucleotide sequence of the dapB gene from the strain NRRL-B11474 (SEQ ID NO:7); the nucleotide sequence of the ddh gene from the strain NRRL-B11474 (SEQ ID NO:9) and the nucleotide sequence of the ORF2 gene from the strain NRRL-B11474 (SEQ ID NO:15). In addition, also provided herein is the nucleotide sequence of lysA (SEQ ID NO:13) gene from plasmid pRS6 (Marcel, T., et al., *Molecular Microbiology* 4: 1819–1830 (1990)).

It is known in the art that amino acids are encoded at the nucleic acid level by one or more codons (code degeneracy). It is also known in the art that choice of codons may influence expression of a particular amino acid sequence (protein, polypeptide, etc.). Thus, the invention is further directed to nucleic acid molecules encoding the ask amino acid sequence of SEQ ID NO:2 wherein the nucleic acid molecule comprises any codon known to encode a particular amino acid. The invention is also further directed to nucleic acid sequences (SEQ ID NOs: 1, 3, 5, 7, 9, 11, 13, 15, 18 and 20) which comprise alternative codons in order to optimize expression of the protein or polypeptide.

In addition to the above described isolated nucleic acid molecules, the invention also provides isolated nucleic acid molecules comprising more than one L-lysine *Corynebacterium glutamicum* biosynthesis gene. Such isolated nucleic acid molecules are referred to as "cassette" constructs. These cassette constructs simplify for the practitioner the number of recombinant DNA manipulations required to achieve gene amplification of L-lysine biosynthesis genes.

In one embodiment drawn to a cassette construct, the invention provides an isolated nucleic acid molecule comprising: (a) a polynucleotide encoding the *Corynebacterium glutamicum* L-lysine pathway ask amino acid sequence of SEQ ID NO:2; and (b) at least one additional Corynebacterium species L-lysine pathway gene selected from the group consisting of: (1) a polynucleotide encoding the asd polypeptide; (2) a polynucleotide encoding the dapA polypeptide; (3) a polynucleotide encoding the dapB polypeptide; (4) a polynucleotide encoding the ddh polypeptide; (5) a polynucleotide encoding the 'lysA polypeptide, and (6) a polynucleotide encoding the ORF2 polypeptide.

The isolated nucleic acid molecules of the invention are preferably propagated and maintained in an appropriate nucleic acid vector. Methods for the isolation and cloning of the isolated nucleic acid molecules of the invention are well known to those skilled in the art of recombinant DNA technology. Appropriate vectors and methods for use with prokaryotic and eukaryotic hosts are described by Sambrook et al., *Molecular Cloning: A Laboratory Manual*, Second Edition, Cold Spring Harbor, N.Y., 1989, the disclosure of which is hereby incorporated by reference.

A great variety of vectors can be used in the invention. Such vectors include chromosomal, episomal and virus-derived vectors, e.g., vectors derived from bacterial plasmids and from bacteriophage, as well as vectors derived from combinations thereof, such as those derived from plasmid and bacteriophage genetic elements, such as cosmids and phagemids, all may be used in accordance with this aspect of the present invention. Generally, any vector suitable to maintain and propagate a polynucleotide in a bacterial host may be used in this regard.

A large numbers of suitable vectors and promoters for use in bacteria are known, many of which are commercially available. Preferred prokaryotic vectors include plasmids such as those capable of replication in *E. coli* (such as, for example, pBR322, ColEl, pSC101, pACYC 184, πVX). Such plasmids are, for example, disclosed by Maniatis, T., et al., *In: Molecular Cloning*, A Laboratory Manual, Cold Spring Harbor Press, Cold Spring Harbor, N.Y. (1982)). The following vectors are provided by way of example: pET (Novagen), pQE70, pQE60, pQE-9 (Qiagen), pBs, phagescript, psiX174, pBlueScript SK, pBsKS, pNH8a, pNH16a, pNH18a, pNH46a (Stratagene), pTrc99A, pKK223-3, pKK233-3, pDR540, pRIT5 (Pharmacia).

Preferred vectors for the isolated nucleic acid molecules of the invention include the pFC1 to pFC7 novel family of combinatorial cloning vectors (Lonsdale, D. M., et al., *Plant Molecular Biology Reporter* 13: 343–345(1995)), the pK184 vector (Jobling, M. G. and Homes, R. K., *Nucleic Acid Research* 18: 5315–5316 (1990)).

Another group of preferred vectors are those that are capable of autonomous replication in Corynebacterium species. Such vectors are well known to those skilled in the art of amino acid production by way of microbial fermentation, examples of which include pSR1, pMF1014α and vectors derived therefrom.

The invention provides an isolated amino acid sequence of the ask polypeptide of the strain ATCC 21529 (SEQ ID NO:2). The isolated ask amino sequence disclosed herein possesses unique properties with respect to feedback resistance of ask enzyme activity to accumulated levels of L-lysine and L-threonine in the culture medium. When compared to the DNA sequences of other *Corynebacterium glutamicum* ask-asd gene sequences, the invention discloses a threonine to isoleucine change at amino acid residue 380 which results in resistance to feedback inhibition. The invention also includes other amino acid changes at residue 380 which result in decreased ask enzyme sensitivity to L-threonine and/or L-lysine.

In addition, and as described in more detail herein, the vector may contain control regions that regulate as well as engender expression. Generally, such regions will operate by controlling transcription, such as inducer or repressor binding sites and enhancers, among others.

Vectors of the present invention generally will include a selectable marker. Such markers also may be suitable for amplification or the vectors may contain additional markers for this purpose. In this regard, vectors preferably contain one or more selectable marker genes to provide a phenotypic trait for selection of transformed host cells. Such markers include, but are not limited to, an antibiotic resistance gene such as a chloramphenicol, ampicillin, or kanamycin resistance gene, or an autotrophic gene which allows the host cell to grow in the absence of a nutrient for which the host cell strain is normally auxotrophic.

If the vector is intended to be maintained in the host cell extrachromosomally, it will contain, in addition and origin of replication which will allow it to replicate in the Corynebacterium species host cell. Alternatively, if it is desired that the vector integrate into the Corynebacterium species chromosome, the vector is constructed such that it cannot replicate in Corynebacterium. For example, such a vector might be capable of propagation in another organism, for example, *E. coli*, but lack the proper origin of replication to be propagated in Corynebacterium. In another aspect of this embodiment, the vector is a shuttle vector which can replicate and be maintained in more than one host cell species, for example, such a shuttle vector might be capable of replication in a Corynebacterium host cell such as a *C. glutamicum* host cell, and also in an *E. coli* host cell.

The invention further provides the following isolated the amino acid sequences: the amino acid sequence of the asd polypeptide of the strain ATCC 21529 (SEQ ID NO:4); the amino acid sequence of the dapA polypeptide of the strain NRRL-B11474 (SEQ ID NO:6); the amino acid sequence of the dapB polypeptide of the strain NRRL-B11474 (SEQ ID NO:8); the amino acid sequence of the ddh polypeptide of the strain NRRL-B11474 (SEQ ID NO:10) and the amino acid sequence of the ORF2 polypeptide of the strain NRRL-B11474 (SEQ ID NO:16). In addition, also provided herein is the amino acid sequence of lysA (pRS6) (Marcel, T., et al., *Mol. Microbiol.* 4: 819–830 (1990)) (SEQ ID NO:14).

In addition to the isolated polypeptide sequences defined by the specific sequence disclosures disclosed above, the invention also provides the amino acid sequences encoded by the deposited clones.

It will be recognized in the art that some amino acid sequences of the invention can be varied without significant effect of the structure or function of the proteins disclosed herein. Variants included may constitute deletions, insertions, inversions, repeats, and type substitutions so long as enzyme activity is not significantly affected. Guidance concerning which amino acid changes are likely to be phenotypically silent can be found in Bowie, J. U., et al., "Deciphering the Message in Protein Sequences: Tolerance to Amino Acid Substitutions," *Science* 247:1306–1310 (1990).

The strains of the invention may be prepared by any of the methods and techniques known and available to those skilled in the art. Introduction of gene constructs of the invention into the host cell can be effected by electroporation, transduction or other methods. These methods are described in the many standard laboratory manuals referenced and incorporated herein.

Various embodiments of the invention provide strains with increased L-lysine production as a result of gene amplification. By gene amplification is meant increasing the number of copies above the normal single copy number of an L-lysine biosynthesis pathway gene by a factor of 2, 3, 4, 5, 10, or more copies.

In one embodiment of the invention, the additional copies of the L-lysine biosynthesis pathway gene(s) may be integrated into the chromosome. Another embodiment of the invention provides that the additional copies of the L-lysine biosynthesis pathway gene(s) are carried extra-chromosomally. Amplifications by a factor of 5 or less may be obtained by introducing the additional gene copies into the chromosome of the host strain by way of single event homologous recombination. In a most preferred embodiment, the recombination event results in the introduction of one additional copy of the copy of the gene or genes of interest. If more than 5 copies of the genes are desired, then the invention also provides for the use of multicopy plasmids carrying the recombinant DNA construct of the invention.

Representative examples of appropriate hosts for isolated nucleic acid molecules of the invention include, but are not limited to, bacterial cells, such as *C. glutamicum, Escherichia coli*, Streptomyces and *Salmonella typhimurium* cells; and fungal cells, such as yeast cells. Appropriate culture media and conditions for the above-described host cells are known in the art.

Particularly preferred host cells of the invention include: *Corynebacterium glutamicum, Brevibacterium flavum* and *Brevibacterium lactofermentum*.

Applicants have deposited clones carrying the pK184-KDABH'L multi-gene constructs at an acceptable International Depository Authority in accordance with the Budapest Treaty on the International Recognition of the Deposit of Microorganisms for the Purposes of Patent Procedure. The deposits have been made with the Agricultural Research Service, Culture Collection (NRRL), 1815 North University Street, Peoria, Ill. 61604. Deposits made in which the pK184-KDAB or pK184-KDABH'L multi-gene constructs have been integrated into the chromosome of a host cell include the following: (1) the pK184-KDAB plasmid, integrated into the chromosome, deposited as NRRL-B30219 and NRRL-B30221 on Sep. 16, 1999 and (2) the pK184-KDABH'L plasmid, integrated into the chromosome, deposited as NRRL-B30218, NRRL-B30220, and NRRL-B30222 on Sep. 16, 1999. In addition, the pK184-KDABH'L multitigene construct in a plasmid configuration, carried in *E. coli* DH5α MCR, was deposited as NRRL-B30228 on Sep. 29, 1999, and the pK184-KDAB isolated plasmid in *E. coli* was deposited as NRRL-B30628 on Sep. 17, 2002. *E. coli* comprising pD11-KDABH'L was deposited as NRRL-B30629 on Sep. 17, 2002. The six gene construct (pDElia2-KDABHL) was deposited in *E. coli* (NRRL-B30233) on Dec. 16, 1999. *C. glutamicum* comprising pK184-KDABH'L was deposited as NRRL-B30236 on Dec. 16, 1999. *C. glutamicum* comprising pK184-KDABHL was deposited as NRRL-B30237 on Dec. 16, 1999. *C. glutamicum* comprising pDElia2-KDABHP1L was deposited as NRRL-B30359 on Oct. 31, 2000. *Brevibacterium flavum* comprising pDElia2-KDABHL was deposited as NRRL-B30234 on Dec. 16, 1999. *Brevibacterium lactofermentum* comprising pDElia2-KDABHL was deposited as NRRL-B30235 on Dec. 16, 1999.

It is an object of the invention to provide a method of producing lysine comprising culturing the host cells comprising the amino acid sequence of SEQ ID NO:2 wherein said host cells comprise one or more of: (a) increased enzyme activity of one or more lysine biosynthetic pathway enzymes compared to the genetically unaltered host cell; (b) one or more copies of each gene encoding a lysine biosynthetic pathway enzyme; and, (c) alteration of one or more transcription factors regulating transcription of one or more genes encoding a lysine biosynthetic pathway enzyme, wherein said host cell produces lysine in said culture medium. In one embodiment of the method, said increased enzyme activity comprises overexpressing one or more genes encoding one or more lysine biosynthetic pathway enzymes. In one embodiment of the method, said one or more genes are operably linked directly or indirectly to one or more promoter sequences. In another embodiment of the method, said operably linked promoter sequences are heterologous, endogenous, or hybrid. In a preferred embodiment of the method, said promoter sequences are one or more of: a promoter sequence from the 5' end of genes endogenous to *C. glutamicum*, a promoter sequence from plasmids that replicate in *C. glutamicum*, and, a promoter sequence from the genome of phage which infect *C. glutamicum*. In a preferred embodiment of the method, one or more of said promoter sequences are modified. In another preferred embodiment, said modification comprises truncation at the 5' end, truncation at the 3' end, non-terminal insertion of one or more nucleotides, non-terminal deletion of one or more nucleotides, addition of one or more nucleotides at the 5' end, addition of one or more nucleotides at the 3' end, and, combinations thereof.

In another embodiment of the method, said increased enzyme activity results from the activity of one or more modified lysine biosynthetic pathway enzymes wherein said enzyme modification results in a change in kinetic parameters, allosteric regulation, or both, compared to the enzyme lacking the modification. In one embodiment of the method, said change in kinetic parameters is a change in $K_m$, $V_{max}$ or both. In another embodiment of the method, said change in allosteric regulation is a change in one or more enzyme allosteric regulatory sites. In one embodiment, said change in allosteric regulation is a change in the affinity of one or more enzyme allosteric regulatory sites for the ligand or ligands. The ligands may be the same or different. In one embodiment, said enzyme modification is a result of a change in the nucleotide sequence encoding said enzyme. In one embodiment, said change in said nucleotide sequence is an addition, insertion, deletion, substitution, or a combination thereof, of one or more nucleotides.

In another embodiment of the method, said alteration of one or more transcription factors comprises one or more mutations in transcription inhibitor proteins, one or more mutations in transcription activator proteins, or both, wherein said one or more mutations increases transcription of the target nucleotide sequence compared to the transcription by said one or more transcription factors lacking said alteration. In one embodiment, said one or more mutations is a change in said nucleotide sequence encoding said transcription factor. In another embodiment, said change in said nucleotide sequence is an addition, insertion, deletion, substitution, or a combination thereof, of one or more nucleotides.

All patents and publications referred to herein are expressly incorporated by reference in their entirety.

EXAMPLES

Example 1

Preparation of L-Lysine Pathway Multi-gene Constructs pK184-KDAB and pK184-KDABH'L Applicants have created L-lysine amino acid biosynthetic pathway multi-gene constructs for the purpose of amplifying the number of one or more of the genes of this pathway in the chromosome of Corynebacterium species. Also, through careful study of the L-lysine biosynthesis genes of strain ATCC 21529, Applicants have identified an amino acid change of threonine to isoleucine at amino acid residue 380 of the ask gene of ATCC 21529. Compared to the DNA sequences of other Corynebacterium glutamicum ask genes, a threonine to isoleucine change at amino acid residue 380 was observed (FIG. 19), which is responsible for the unusual feedback resistant properties with respect to aspartate kinase enzyme regulation.

The isolated nucleic acid molecules encoding L-lysine, amino acid biosynthesis pathway genes utilized in the present invention are from the following sources:

| Gene(s) | Source |
|---------|--------|
| ask-asd | Strain ATCC 21529; |
| dapA | Strain NRRL B11474; |
| dapB | Strain NRRL B11474; |
| ddh | Strain NRRL B11474; |
| lysA | Plasmid pRS6 (Marcel, T., et al., Mol. Microbiol. 4: 819–830 (1990)) carrying the lysA gene isolated from strain AS019, which was derived from ATCC 13059; |
| lysA | NRRL B11474; |
| lysA | NRRL B11474 (full length); and, |
| ORF2 | Strain NRRL B11474. |

As one skilled in the art would know, the invention is not limited to the specific strain origins that Applicants present for the isolated nucleic acid molecules of the invention. Any strain of Corynebacterium species, particularly that of Corynebacterium glutamicum, may be utilized for the isolation of nucleic acid molecules that will be used to amplify the number of chromosomally located amino acid biosynthetic pathway genes. Particularly preferred strains include: NRRL-B11474, ATCC 21799, ATCC 21529, ATCC 21543, and E12.

Methods and techniques common to the art of recombinant DNA technology were used in making the multi-gene constructs of the invention, as may be found in the many laboratory manuals cited and incorporated herein, for example as found in J. Sambrook, E. F. Fritsch and T. Maniatis, *Molecular Cloning: A Laboratory Manual*, 2d ed., Cold Spring Harbor Laboratory Press, Cold Spring Harbor, N.Y. (1989).

The polymerase chain reaction (PCR) technique is used extensively in the making of the multi-gene constructs of the invention. In a typical reaction, the standard 10× stock solution (100 mM Tris-HCL, pH 8.3, 500 mM KCL, 1.5 mM $MgCl_2$) is diluted to 1× for use. Typical reaction conditions were used for PCR amplication: 10 mM Tris, pH 8.3, 50 mM KCl, 1.5 mM $MgCl_2$, 0.01% gelatin, 200 μM deoxynucleotides, 0.2–1.0 μM primers and 2.5 U/100 μl pfu polymerase. Standard cycling parameters were also employed in PCR reactions: For 30 cycles, template denaturation was performed at 94° C. for 1 min; 55° C. annealing temperature was performed for 1 min (or annealing temperature appropriate for particular primer pair); product extension was performed at 72° C. for 1 min (if product is <500 bp), 3 min (if product is >500 bp); and at the end of cycling, a final extension at 72° C. for 7 min was performed.

The primers utilized for cloning experiments included:

ask: 5'-GGGTACCTCGCGAAGTAGCACCTGTCAC-3' (SEQ ID NO:22);

asd: 5'-GCGGATCCCCCATCGCCCCTCAAAGA-3' (SEQ ID NO:23);

dapB: 5'-AACGGGCGGTGAAGGGCAACT-3' (SEQ ID NO:24);

dapA: 5'-TGAAAGACAGGGGTATCCAGA-3' (SEQ ID NO:25);

ddh: 5'-CCATGGTACCAAGTGCGTGGCGAG-3' (SEQ ID NO:26);
5'-CCATGGTACCACACTGTTTCCTTGC-3' (SEQ ID NO:27);

argS: 5'-CTGGTTCCGGCGAGTGGAGCCGACCATT-CCGCGAGG-3' (SEQ ID NO:28); and lysA: 5'-CTCGCTCCGGCGAGGTCGGAGGCAAC-TTCTGCGACG-3' (SEQ ID NO:29), a primer that anneals internally to lysA (about 500 bp upstream to the end of lysA). 'LysA is a truncated form obtained from lysA.

Figure 18A:
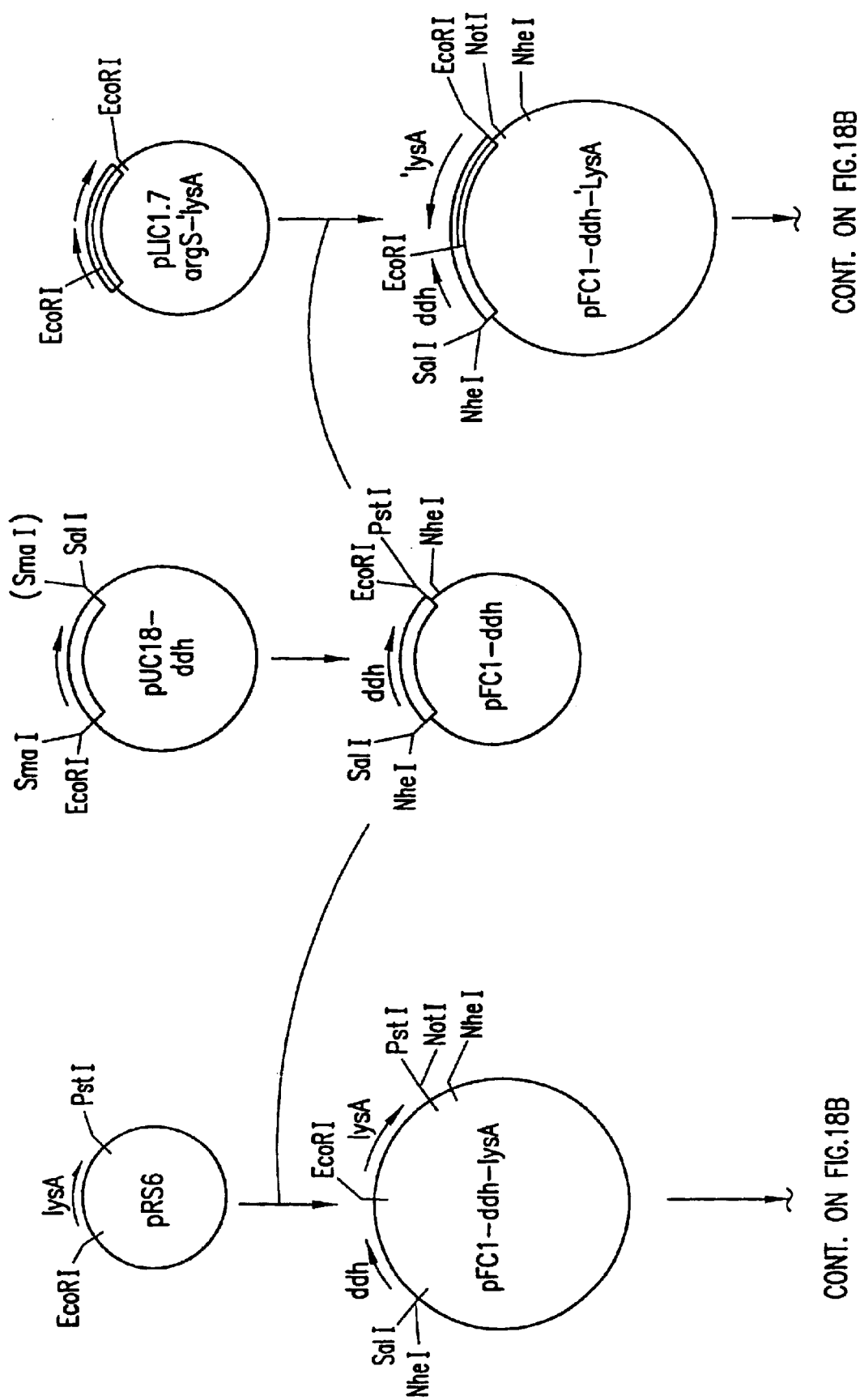
FIG. 18. A schematic depiction of the construction of the pFC3-KDABHL and pFC3-KDABH'L lysine pathway gene constructs of the invention.
Figure 18B:
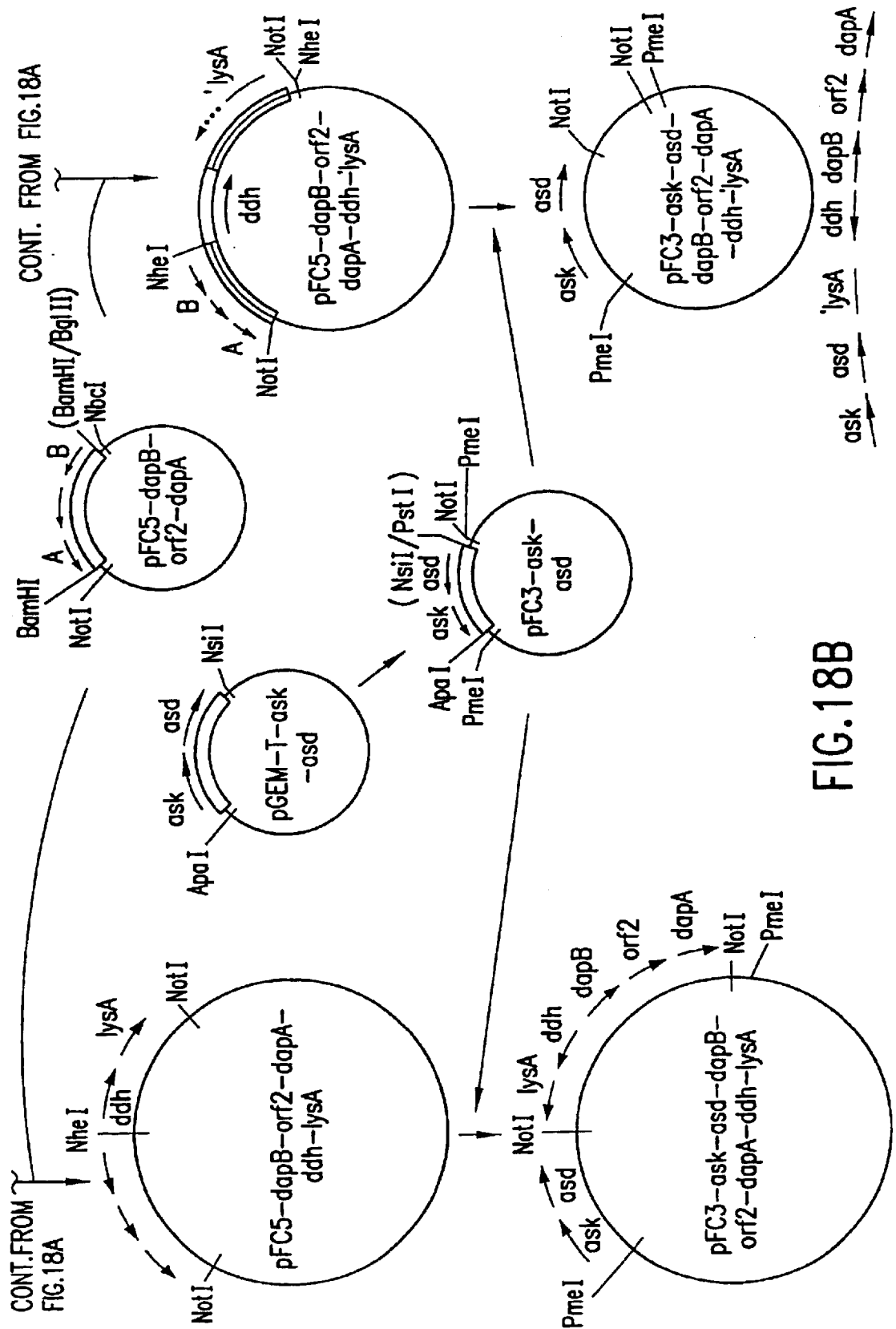
Figure 21A:
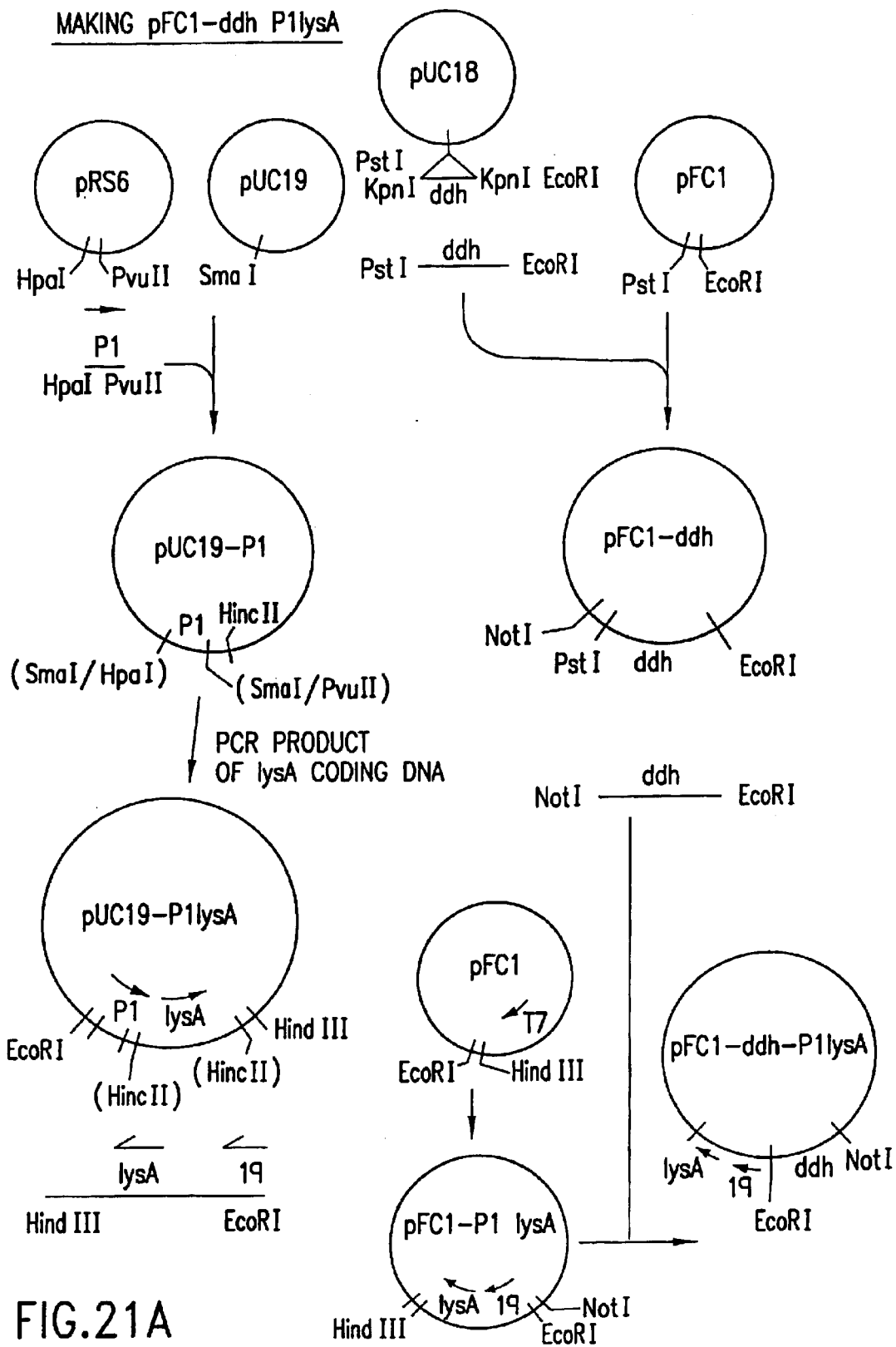
FIGS. 21A, B. A schematic depiction of the construction of the pDElia2-KDABHP1L construct.
Figure 21B:
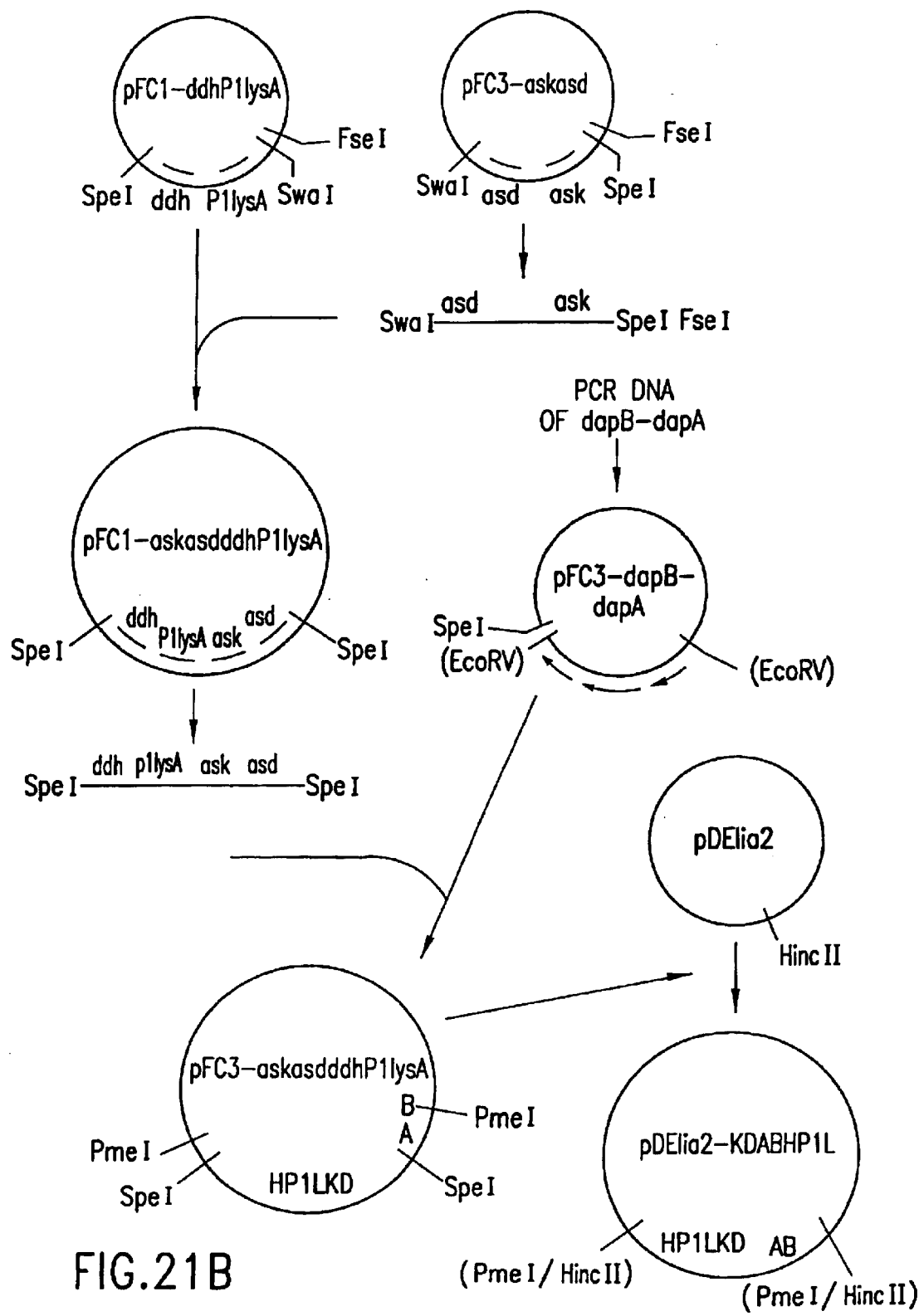
Figure 22:
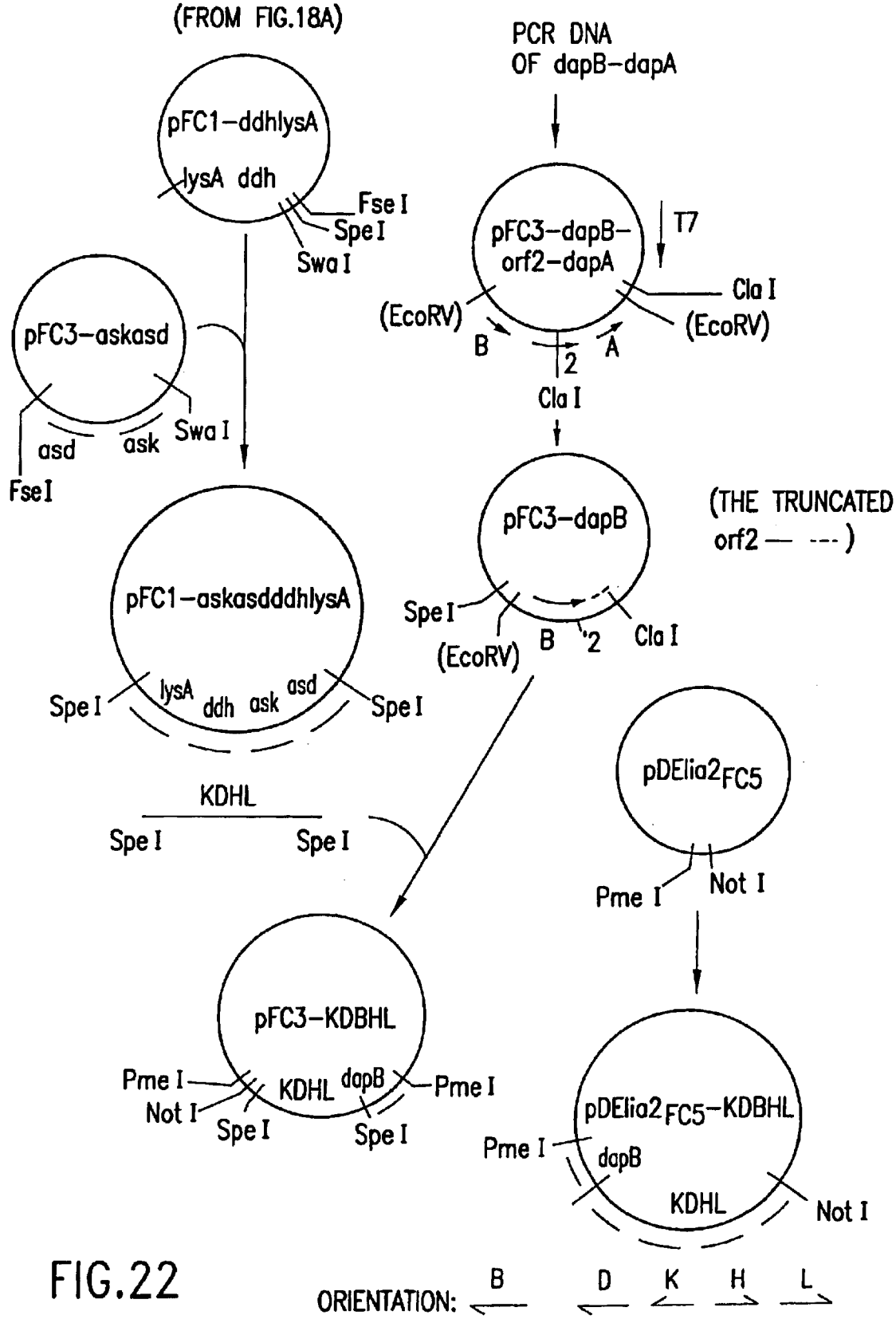
FIG. 22. A schematic depiction of the construction of the pDElia2$_{FCS}$-KDBHL construct.

Applicants utilized standard PCR and subcloning procedures in cloning the coding regions of ask-asd, dapB-ORF2-dapA, ddh, 'lysA, and lysA. Construction procedures and intermediate plasmids are described in FIG. 18. Applicants performed the following steps (FIG. 18) in constructing the following vectors used in the L-lysine biosynthetic pathway:

1. pGEMT-ask-asd: an approximately 2.6 Kb PCR product containing the ask-asd operon of ATCC21529 using primers ask and asd was cloned into pGEM-T (Promega pGEM-T vector systems);

2. pADM21: an approximately 1.3 Kb PCR product (with an engineered KpnI site on both primers) of NRRL-B11474 ddh coding region was cloned into pADM20;

3. pUC 18-ddh: an approximately 1.3 Kb KpnI fragment of pADM21 containing ddh (NRRL-B11474) was subcloned into pUC 18 at the KpnI site;

4. pLIC 1.7-argS-'lysA: PCR product using template NRRL-B11474 genomic DNA and primers argS and lysA was cloned into pPMG-LIC cloning vector (PharMingen);
5. pM4-dapB-ORF2-dapA.: an approximately 3 Kb PCR product using primers dapB and dapA was cloned into pM4 at the XbaI site;
6. pFC3-ask-asd: an approximately 2.6 Kb NsiI-ApaI fragment of pGEMT-ask-asd was cloned into pFC3 cut with PstI and ApaI;
7. pFC1-ddh: ~1.3 Kb SalI-EcoRI fragment of pUC18-ddh was cloned into pPC1 cut with SalI and EcoRI;
8. pFC1-ddh-'lysA: an approximately 1.5 Kb EcoRI fragment (containing the truncated lysA DNA) of pLIC1.7-argS-'lysA was cloned into pFC1-ddh at the EcoRI site;
9. pFC5-dapB-ORF2-dapA: an approximately 3.4 Kb BamHI-BglII fragment of pM4-dapB-ORF2-dapA was cloned into pFC5 at the BamHI site;
10. pFC5-dapB-ORF2-dapA-ddh-'lysA: ~2.8 Kb NheI fragment of pFC1-ddh-'lysA was cloned into pFC5-dapB-ORF2-dapA at the NheI site;
11. pFC-3-ask-asd-dapB-ORF2-dapA-ddh-'lysA: ~6.2 Kb NotI fragment of pFC5-dapB-ORF2-dapA-ddh-'lysA was cloned into pFC3-ask-asd at the NotI site;
12. pDElia9-ask-asd-dapB-ORF2-dapA-ddh-'lysA (pDElia9-KDABH'L): ~8.8 Kb PmeI fragment of pFC3-ask-asd-dapB-ORF2-dapA-ddh-'lysA was cloned into pDElia9 at the EcoRV site; and
13. pK184-ask-asd-dapB-ORF2-dapA-ddh-'lysA (pK184-KDABH'L): an approximately 8.8 Kb PmeI fragment of pFC3-ask-asd-dapB-ORF2-dapA-ddh-'lysA was cloned into pK184 at the HincII or SmaI site.
14. pFC5-ask-asd-dapB-ORF2-dapA (pFC5-KDAB): ~2.6 Kb KpnI-SmaI fragment of pFC3-ask-asd was cloned into pFC5-dapB-ORF2-dapA cut with KpnI and SmaI.
15. pK184-ask-asd-dapB-ORF2-dapA (pK184-KDAB): ~7 Kb KpnI-PmeI fragment of pFC5-ask-asd-dapB-ORF2-dapA was cloned into pK184 cut with KpnI and HincII.

Thus, Applicants have made the following L-lysine multi-gene constructs:

1. pK184-KDABH'L, wherein "K" represents a nucleotide sequence encoding the ask polypeptide; "D" represents a nucleotide sequence encoding the asd polypeptide; "A" represents a nucleotide sequence encoding the dapA polypeptide; "B" represents a nucleotide sequence encoding the dapB polypeptide; "H'" represents a nucleotide sequence encoding the ddh polypeptide; and "'L" represents a nucleotide sequence encoding part of the 'lysA polypeptide. This construct is referred to as a truncated 6 gene construct. The pK184-KDABHL construct, constructed infra, is referred to as a full length 6 gene construct.
2. pK184-KDAB, wherein "K" represents a nucleotide sequence encoding the ask polypeptide; "D" represents a nucleotide sequence encoding the asd polypeptide; "A" represents a nucleotide sequence encoding the dapA polypeptide; and "B" represents a nucleotide sequence encoding the dapB polypeptide. This construct is referred to as a 4 gene construct.

Both pK184-KDABH'L and pK184-KDAB, as do the other constructs discussed herein, comprise the nucleotide sequence encoding the ORF2 polypeptide.

It should be noted that in addition to the indicated polypeptide sequences encoded by the isolated nucleic acid sequences represented by "K", "D", "A", "B," "H," "L" and "'L", these isolated nucleic acid sequences also include native promoter elements for the operons represented therein. Thus, the ask-asd sequences have been cloned in a fashion that includes the respective native promoter elements, the dapA and dapB sequences, representing the operon dapB-ORF2-dapA, have been cloned in a fashion that includes the respective promoter elements; the ddh sequence has been cloned in a fashion that includes the respective native promoter elements, and the lysA and 'lysA sequences have been cloned in a fashion that includes a native promoter element.

Alternative gene promoter elements may be utilized in the constructs of the invention. For example, known bacterial promoters suitable for this use in the present invention include the E. coli lacI and lacZ promoters, the T3 and T7 promoters, the gpt promoter, the lambda PR and PL promoters, the trp promoter, or promoters endogenous to the bacterial cells of the present invention. Other promoters useful in the invention include regulated promoters, unregulated promoters and heterologous promoters. Many such promoters are known to one of skill in the art. See Sambrook, E. F. et al., *Molecular Cloning: A Laboratory Manual*, 2d ed., Cold Spring Harbor Laboratory Press, Cold Spring Harbor, N.Y. (1989).

Example 2

Two-Fold Amplification of L-lysine Amino Acid Biosynthesis Pathway Genes

For exemplary purposes only, Applicants provide herein an example wherein at least one L-lysine amino acid biosynthesis pathway gene is amplified by a factor of 2 by way of (a) the introduction of an isolated nucleic acid molecule into a *Corynebacterium glutamicum* host cell, and (b) the subsequent single crossover homologous recombination event introducing said isolated nucleic acid molecule into said *Corynebacterium glutamicum* host cell chromosome.

As will be understood by those in the art, at least one or two or three or four or five or six or seven or eight or nine or ten or more amino acid biosynthesis pathway genes may be amplified, i.e., increased in number, by a factor of at least one or two or three or four or five or six or seven or eight or nine or ten fold with minor variations of the example presented herein.

pK184-KDAB, pK184-KDABH'L and pD2-KDABHL (a full length 6 gene construct constructed in Example 4) plasmids were used in the construction of high yield derivative cell lines of the invention. This was accomplished by way of introducing plasmid pK184-KDAB, pK184-KDABH'L and pD2-KDABHL DNAs into a Corynebacterium species resulting in incorporation of pK184-KDAB, pK184-KDABH'L or pD2-KDABHL into the host cell chromosome via a single crossover homologous recombination event. Amplification of the amino acid biosynthetic pathway genes by way of chromosomal integration of the plasmid constructs of the invention provided increased L-lysine production in several Corynebacterium species strains.

For cell transformation experiments with the isolated nucleic acid molecules of the invention, the growth and preparation of competent cells may be done according to the following procedure: (1) picking a fresh, single colony of *Corynebacterium glutamicum* and growing a culture overnight in 10 mL CM (SM1) in a 250 mL shake flask at 30 degrees Celsius with agitation; (2) inoculating 200 mL of "Growth Media" with the overnight culture to an optical density (O.D.) of 660 nm of 0.1 in a 500 mL shake flask; (3) growing the culture at 30 degrees Celsius with agitation for 5–6 hours; (4) pouring the culture into a chilled, sealed, sterile 250 mL centrifuge bottle; Spin at 8–10K for ten minutes in Refrigerated Sorvall at 4 degrees Celsius; (5) pouring off the supernatant thoroughly and resuspending the cell pellet in an equal volume of ice-cold, sterile, deionized water; (6) centrifuging the sample again under the same conditions; (7) repeating the water wash remembering to keep everything ice-cold; (8) pouring off the supernatant thoroughly and resuspending the cell pellet in 1 mL of ice-cold, sterile 10% glycerol and transferring the cells to a chilled, sterile, 1.5 mL microcentrifuge tube; (9) spin the sample for 10 minutes in a refrigerated centrifuge; (10) pipetting off and discarding the supernatant, and resuspending the pellet in two to three times the pellet volume (200–400 µL) of 10% glycerol; and (11) alliquoting, if necessary, the cells into chilled tubes and freezing at −70 Celsius.

pK184-KDAB, pK184-KDABH'L and pD2-KDABHL plasmid DNAs were introduced into *Corynebacterium glutamicum* host cells by the following electroporation procedure: (1) pipetting 35 µL cell/glycerol solution onto the side wall of a chilled 0.1 cm electrocuvette; (2) pipetting about 2–4 µL of plasmid into the solution and mixing the sample by gentle pipetting up and down; (3) bringing the entire solution to the bottom of the electrocuvette by gentle tapping, avoiding the creation of bubbles; (4) keeping the sample on ice until ready for the electroshock step, wiping off any moisture on the outside of the electrocuvette prior to the electroshock administration, and shocking the cells one time at 1.5 kV, 200Ω, 25 µF.

Cells are allowed to recover from electroporation by: (1) immediately pipetting 1 mL of warm "Recovery Media" into the electrocuvette and thoroughly mixing the solution by pipetting; (2) incubating the solution (in the electrocuvette) at 30 degrees Celsius for at least three hours for antibiotic resistance expression and cell recovery and (3) plating on selection media and incubating at 30 degrees Celsius for 3 days.

Example 3

Screening and Selection of Strains with Improved L-Lysine Production

After 3 days of growth, single colonies of antibiotic resistant cells are individually selected to determine if there is increased L-lysine production over that which is produced by the parental host cell strain.

Recipes for all media used in these experiments are found in Tables 1 and 2. L-lysine production is determined on cultures of transformed, antibiotic resistant cells grown in shaker flasks. Briefly, seed media (Table 1), was dispensed in 20 ml aliquots into deep baffled 250 ml Bellco shake flasks and autoclaved for 20 minutes. After cooling to room temperature, these seed flasks were then inoculated with the strain to be tested and placed on a rotary shaker. They were incubated at 30 degrees Celsius, shaking, overnight. The following morning, the optical density (wavelength=660 nm) of each seed was recorded, and 2 ml of the culture from each seed flask was transferred to a 21 ml aliquot of FM3 media, also in a deep baffled shake flask. These "main" flasks were then returned to the shaker and incubated at 30 degrees Celsius.

After 48 hours of incubation, 1 ml of main culture was removed from each flask, and the flasks were promptly returned to the shaker. From the 1 ml sample, optical density was determined by diluting 1:50 in 0.1N HCl to dissolve the calcium carbonate present in the media. The remainder of each sample was then centrifuged to pellet cells and calcium carbonate. A 1:50 dilution of the supernatant was made in water and from this dilution the dextrose concentration was determined. Extracellular L-lysine concentrations were also determined at this time by HPLC.

High yield derivative cells may be conveniently identified by determining the percent yield from dextrose, i.e., the yield of amino acid from dextrose defined by the formula [(g amino acid produced/g dextrose consumed)*100]=% yield. Results are presented below in which the parental strains E12, NRRL-B11474 and ATCC 21799 are transformed with the L-lysine multi-gene isolated nucleic acid molecules of the invention identified as pK184-KDA, pK184-KDABH'L and pD(Elia)2-KDABHL. The pD2-KDABHL construct was made as in Example 4.

| Strain Tested | lysine titer (g/L) | L-lysine yield (%) | Cell Deposit |
|---|---|---|---|
| NRRL-B11474 | 31 | 44 | |
| NRRL-B11474::pK184-KDAB | 32 | 45.7 | NRRL-B-30219 |
| NRRL-B11474::pK184-KDABH'L | 36 | 51.8 | NRRL-B-30218 |
| NRRL-B11474::pDElia2-KDABHL | 38 | 54.6 | NRRL-B-30234 |
| E12 | 1.4 | 0.9 | |
| E12::pK184-KDABH'L | 26.8 | 38 | NRRL-B-30236 |
| E12::pDElia2-KDABHL | 29.8 | 42.5 | NRRL-B-30237 |
| ATC21799 | 26.8 | 36.9 | |
| ATC21799::pK184-KDAB | 28.5 | 39 | NRRL-B-30221 |
| ATC21799::pK184-KDABH'L | 31 | 43 | NRRL-B-30220 |
| ATC21799::pDElia2-KDABHL | 36 | 50 | NRRL-B-30235 |

Once high yield derivative cell lines are identified, the cell lines are further screened to determine that amplification of the amino acid biosynthetic pathway genes has occurred. Amplification screening may be conveniently accomplished either by (1) standard southern blot methodology to determine gene copy number or (2) by a determination of the total enzyme activity for enzymes encoded by the respective biosynthetic pathway genes of the isolated nucleic acid molecule introduced into the host cell.

A determination of gene copy number by Southern blot methodology may be done utilizing standard procedures known in the art of recombinant DNA technology, as described in the laboratory manuals referenced and incorporated herein, for example as found in J. Sambrook, E. F. Fritsch and T. Maniatis, *Molecular Cloning: A Laboratory Manual*, 2d ed., Cold Spring Harbor Laboratory Press, Cold Spring Harbor, N.Y. (1989).

TABLE 1

| Seed Media, SM1 | |
|---|---|
| Ingredient | Concentration (g/L) |
| Sucrose | 50 |
| Potassium Phosphate, Monobasic | 0.5 |
| Potassium Phosphate, Dibasic | 1.5 |
| Urea | 3.0 |
| Magnesium Sulfate | $5.0 \times 10^{-1}$ |
| Polypeptone | 20 |
| Beef Extract | 5.0 |
| Biotin | $7.56 \times 10^{-4}$ |
| Thiamine | $3.0 \times 10^{-3}$ |
| Niacinamide | $1.25 \times 10^{-1}$ |

TABLE 1-continued

Seed Media, SM1

| Ingredient | Concentration (g/L) |
| --- | --- |
| L-Methionine | $5.0 \times 10^{-1}$ |
| L-Threonine | $2.5 \times 10^{-1}$ |
| L-Alanine | $5.0 \times 10^{-1}$ |
| pH | 7.3 |

TABLE 2

Main Media, FM3

| Ingredient | Concentration (g/L) |
| --- | --- |
| Dextrose* | 60 |
| Ammonium Sulfate | 50 |
| Potassium Phosphate, Monobasic | 1.0 |
| Magnesium Sulfate | $4.0 \times 10^{-1}$ |
| Manganese Sulfate | $1.0 \times 10^{-2}$ |
| Ferrous Sulfate | $1.0 \times 10^{-2}$ |
| Biotin | $3.0 \times 10^{-4}$ |
| Calcium Carbonate | 50 |
| Corn Steep Liquor (dissolved solids) | 20 |
| pH (adjusted with KOH) | 7.4 |

*Dextrose was added after autoclaving

Example 4

Preparation of L-Lysine Pathway Multi-Gene Constructs

The invention further comprises additional L-lysine multi-gene constructs constructed using the PCR technique. Standard PCR and subcloning procedures were utilized, as described above, to generate 5-gene constructs similar to those in Example 1. The constructs of this example comprise the antibiotic resistance gene, chloramphenicol acyl transferase (CAT). The CAT gene was operably linked to a Corynebacteria phosphofructokinase promoter for expression in Corynebacteria.

The following steps were performed in constructing the following constructs containing the CAT gene:

1. pGEMT-ask-asd: ~2.6 Kb PCR product containing the ask-asd operon of ATCC21529 using primers ask and asd was cloned into pGEM-T (Promega pGEM-T vector systems);
2. pUC18-ddh: ~1.3 Kb KpnI fragment of pADM21 containing ddh (NRRL B11474) was subcloned into pUC18 at the KpnI site;
3. pLIC1.7-argS-'lysA: ~3 Kb PCR product using template BF100 genomic DNA and primers argS and lysA was cloned into pPMG-LIC cloning vector (PharMingen);
4. pM4-dapB-ORF2-dapA: ~3 Kb PCR product using primers dapB and dapA was cloned into pM4 at the blunted XbaI site;
5. pFC3-ask-asd: ~2.6 Kb NsiI-ApaI fragment of pGEMT-ask-asd was cloned into pFC3 cut with PstI and ApaI;
6. pFC1-ddh: ~1.3 Kb SalI-EcoRI fragment of pUC18-ddh was cloned into pFC1 cut with SalI and EcoRI;
7. pFC1-ddh-'lysA: ~1.5 Kb EcoRI fragment (containing the truncated lysA DNA) of pLIC1.7-argS-'lysA was cloned into pFC1-ddh at the EcoRI site;
8. pFC1-ddh-lysA: ~2.1 Kb EcoRI-PstI fragment (containing the intact lysA DNA) of pRS6 was cloned into pFC1-ddh cut with EcoRI and PstI;
9. pFC5-dapB-ORF2-dapA: ~3.4 Kb BamHI-BglII fragment of pM4-dapB-ORF2-dapA was cloned into pFC5 at the BamHI site;
10. pFC5-dapB-ORF2-dapA-ddh-'lysA: ~2.8 Kb NheI fragment of pFC1-ddh-'lysA was cloned into pFC5-dapB-ORF2-dapA at the NheI site;
11. pFC5-dapB-ORF2-dapA-ddh-lysA: ~3.4 Kb NheI fragment of pFC1-ddh-lysA was cloned into pFC5-dapB-ORF2-dapA at the NheI site;
12. pFC3-ask-asd-dapB-ORF2-dapA-ddh-'lysA (pFC3-KDABH'L): ~6.2 Kb NotI fragment of pFC5-dapB-ORF2-dapA-ddh-'lysA was cloned into pFC3-ask-asd at the NotI site;
13. pFC3-ask-asd-dapB-ORF2-dapA-ddh-lysA (pFC3-KDABHL): ~6.8 Kb NotI fragment of pFC5-dapB-ORF2-dapA-ddh-lysA was cloned into pFC3-ask-asd at the NotI site;
14. pK184-ask-asd-dapB-OPF2-dapA-ddh-'lysA (pk184-KDABH'L): ~8.8 Kb PmeI fragment of pFC3-ask-asd-dapB-ORF2-dapA-ddh-'lysA was cloned into pK184 at the HincII or SmaI site;
15. pDElia2-ask-asd-dapB-ORF2-dapA-ddh-lysA (pD2-KDABHL): ~9.4 Kb PmeI fragment of pFC3-ask-asd-dapB-ORF2-dapA-ddh-lysA was cloned into pDElia2 at the HincII site (contains the kan gene; is a full length 6 gene construct);
16. pDElia11-ask-asd-dapB-ORF2-dapA-ddh-'lysA (pD11-KDABH'L): ~8.8 Kb PmeI fragment of pFC3-ask-asd-dapB-ORF2-dapA-ddh-'lysA was cloned into pDElia11 at the HincII or SmaI site (contains the CAT gene; is a truncated 6 gene construct);
17. pDElia11-ask-asd-dapB-ORF2-dapA-ddh-lysA (pD11-KDABHL): ~9.4 Kb PmeI fragment of pFC3-ask-asd-dapB-ORF2-dapA-ddh-lysA was cloned into pDElia11 at the HincII site (contains the CAT gene; is a full length 6 gene construct);
18. pDElia2: ~1.24 Kb blunted PstI fragment of pUC4K ligated with the ~1.75 Kb DraI-SspI fragment of pUC 19;
19. pDElia11: ~1 Kb PCR product containing the chloramphenicol acyl-transferase gene expressed by the C. glutamicum fda promoter was obtained using primers UCdraI and UCsspI and pM4 as template and was ligated with the ~1.75 Kb DraI-SspI fragment of pUC19;

The primers utilized for the cloning procedures included:

ask: 5'-GGGTACCTCGCGAAGTAGCACCTGTCAC-3' (SEQ ID NO:22)
asd: 5'-GCGGATCCCCCATCGCCCCTCAAAGA-3' (SEQ ID NO:23)
dapB: 5'-AACGGGCGGTGAAGGGCAACT-3' (SEQ ID NO:24)
dapA: 5'-TGAAAGACAGGGGTATCCAGA-3' (SEQ ID NO:25)
ddh1: 5'-CCAT<u>GGTACC</u>AAGTGCGTGGCGAG-3' (SEQ ID NO:26)
ddh2: 5'-CCAT<u>GGTACC</u>ACACTGTTTCCTTGC-3' (SEQ ID NO:27) KpnI sites:GGTACC (SEQ ID NO:30)

argS: 5'-CTGGTTCCGGCGAGTGGAGCCGACCA-TTCCGCGAGG-3' (SEQ ID NO:28)

lysA: 5'-CTCGCTCCGGCGAGGTCGGAGGCAAC-TTCTGCGACG-3' (SEQ ID NO:29)

a primer that anneals internally to lysA (about 500 bp upstream to the end of lysA).

UCdraI: 5'-GGATCTTCACCTAGATCC-3' (SEQ ID NO:31)

UcsspI: 5'-CCCTGATAAATGCTTC-3' (SEQ ID NO:32) "K", "D", "A", "B," "H," "L" and "'L" have the same designations as set forth above.

Example 5

Three-Fold Amplification of L-lysine Amino Acid Biosynthesis Pathway Genes

For exemplary purposes only, Applicants provide herein an example wherein at least one L-lysine amino acid biosynthesis pathway gene is amplified by a factor of 3.

Plasmid pD11-KDABH'L (constructed in Example 4) was used in the construction of high yield derivative cell lines of the invention. For cell transformation experiments with the isolated nucleic acid molecules of the invention, the growth preparation of competent cells, and determining of relative growth may be done according to the procedure set forth above.

Plasmid pD11-KDABH'L DNA was introduced into NRRL-B30220 (comprising pK184-KDABH'L), using the electroporation method above. Introduction of the pD11-KDABH'L plasmid DNA into NRRL-B30220 resulted in incorporation of one copy of pD11-KDABH'L into the host cell chromosome via a single crossover homologous recombination event. The host cell comprising two copies of five genes (pD11-KDABH'L and pK184-KDABH'L) has been deposited as NRRL-B30222.

The amount of lysine produced by C. glutamicum ATCC 21799 host cells having 3 copies of 5 genes (one endogenous copy and one copy of each of pD11-KDABH'L and pK184-KDABH'L) is shown below.

| | L-lysine Production | |
|---|---|---|
| Strains | L-lysine titer (g/L) | L-lysine yield (%) |
| ATCC 21799 | 26.6 | 45.0 |
| NRRL-B30222 | 32.0 | 56.0 |

Example 6

This example describes changing the promoter to increase the level of expression of each of these 6 genes described above. Six genes encoding six different enyzmes of the biosynthetic pathway from L-aspartate to L-lysine have been inserted onto the chromosome of Corynebacterium glutamicum. The additional copy of each gene is from a C. glutamicum strain. The nucleotide sequences that regulate the level of expression (promoter) for each gene were the same as found on the C. glutamicum chromosome at the native loci.

Increased expression can result in increased specific activities of the enzymes and improved flux of carbon from aspartate to lysine. The yield of lysine from glucose can be improved by this technique.

The level of expression from a promoter sequence is referred to as strength. A strong promoter gives higher expression than a weak one. The mechanisms that determine the strength of a promoter have been described (Record, M. T., et al., "*Escherichia coli* RNA Polymerase, Promoters, and the Kinetics of the Steps of Transcription Initiation," in *Escherichia coli and Salmonella: Cellular and Molecular Biology*, ASM Press (1996), pp. 792–881). Sources of promoters include nucleotide sequences from the 5' end of genes native to the *C. glutamicum* chromosome, from sequences on plasmids that replicate in *C. glutamicum*, from sequences in the genome of phage that infect *C. glutamicum*, or from sequences assembled by humans (tac, trc) and are not found in nature. Genes of ribosomal proteins, ribosomal RNAs and elongation factors show high levels of expression. The promoters of these genes are candidates for increasing expression of amino acid biosynthetic pathway genes.

Another reason for changing promoters of genes in biosynthetic pathways is to make the pathway independent of factors that control the pathway in the wild type organism. For example the native promoter of the operon that contains diaminopimelate decarboxylase of the lysine biosynthetic pathway of *C. glutamicum* can respond to arginine or lysine in the growth medium. Arginine increased transcription three-fold and lysine decreased transcription by one third (Oguiza, et al., *J Bact.* 175:7356–7362(1993)). Diaminopimelate decarboxylase activity decreased 60% in cells grown in minimal medium supplemented with 10 mmM lysine (Cremer et al., *J Gen Microbiol*. 134:3221–3229 (1988)). Replacing the promoter of lysA which encodes the diaminopimelate decarboxylase is one way to make lysine biosynthesis independent of arginine and lysine levels in media.

Example 6A

Shown below are examples of promoters that are stronger than the askP1 promoter which regulates the gene for aspartate kinase, the first enzyme in the pathway from aspartate to lysine.

Beta-Galactosidase Assay of Candidate Promoters

| Candidate | Specific Activity micromol/min/mg | Origin |
|---|---|---|
| E12 | 0.20 | no promoter |
| E12/pTAC | 49.80 | pKK223-3 |
| BF100 | 0.08 | no promoter |
| BF100/pAD151.1 | 2.22 | aspartokinase P1 |
| E12 | 0.11 | no promoter |
| E12/pAD151.1 | 1.96 | aspartokinase P1 |
| E12/5 | 3.46 | BF100 genome |
| E12/7 | 8.60 | BF100 genome |
| E12/10 | 6.56 | BF100 genome |
| E12/32 | 3.11 | BF100 genome |
| E12/3 | 22.00 | corynephage |
| E12/39 | 11.57 | corynephage |
| E12/42 | 10.90 | corynephage |

E12 is a *C. glutamicum* strain that does not produce lysine. E12 is a laboratory strain derived from ATCC 13059. BF100 is a high level lysine producer (NRRL-B11474). TAC is commercially available promoter that has been used as an example of a strong promoter. Four promoters from the *C. glutamicum* chromosome and three from a phage have been identified that are stronger than the native aspartokinase promoter.

Example 6B

Examples of strong promoters increasing specific enzyme activity of aspartokinase when expressed in *C. glutamicum* are shown below.

Influence of IPTG on Aspartokinase Activity

| Strain | Regulator/<br>promoter-gene | Inducer | nmol/min/mg |
|---|---|---|---|
| BF100 | none | none | 110 |
| PD9trc-ask | lacI/trc-ask | none | 103 |
| PD9trc-ask | lacI/trc-ask | +IPTG (30 mg/L) | 269 |
| 131-2 | lacI/trc-ask | none | 59 |
| 131-2 | lacI/trc-ask | +IPTG (30 mg/L) | 117 |
| 131-5 | lacI/trc-ask | none | 59 |
| 131-5 | lacI/trc-ask | +IPTG (30 mg/L) | 123 | pD9 is a plasmid that replicates in *C. glutamicum*.
131 strains have the trc-ask construct integrated into the genome.
IPTG induces genes controlled by the TRC promoter.

Example 6C

Examples of the influence of lacI/trc-ask on lysine production in shake flasks are shown below.

| Strain | Induction | O.D. | Titre | Yield | S.P. |
|---|---|---|---|---|---|
| BF100 | none | 46 | 26 | 43 | 58 |
| PD9trc-ask | none | 49 | 30 | 49 | 61 |
| PD9trc-ask | +IPTG | 45 | 30 | 50 | 68 |
| BF100 | none | 43 | 23 | 39 | 53 |
| 131-2 | none | 34 | 27 | 46 | 82 |
| 131-5 | none | 35 | 28 | 47 | 82 |

O.D. = optical density at 660 nm
Titre = grams Lysine/liter
Yield = grams lysine made/grams dextrose consumed
S.P. = grams lysine/O.D.

The production of lysine by BF100 was improved by increasing the strength of the aspartokinase promoter.

Example 7

This example demonstrates the use of vector pDElia2-ask-asd-dapA-ORF2-dapB-ddh-P1lysA (pDElia2KDABHP1L) in the construction of the high yield cell lines of the invention. The HpaI-PvaII fragment containing the P1 promoter was prepared as described in Marcel T., et al., *Molecular Microbiology* 4:1819–1830 (1990). Applicants utilized standard PCR and subcloning procedures as set forth above. For cell transformation experiments with the isolated nucleic acid molecules of the invention, the growth preparation of competent cells, and determining or relative growth may be done according to the procedure set forth above.

Applicants performed the following steps in constructing the following vectors used in the L-lysine biosynthetic pathway.

1. pGEMT-ask-asd: ~2.6 Kb PCR product containing the ask-asd operon of ATCC21529 using primers ask and asd was cloned into pGEM-T (Promega pGEM-T vector systems).
2. pUC18-ddh: ~1.3 KpnI fragment of pADM21 containing ddh (BF100 locus) was subcloned into pUC18 at the KpnI site.
3. pFC3-ask-asd: ~2.6 Kb NsiI-ApaI fragment of pGEMT-ask-asd was cloned into pFC3 cut with PstI and ApaI.
4. pFC3-dapB-ORF2-dapA: ~2.9 Kb PCR product of NRRL-B11474 dapB-ORF2-dapA coding region was cloned into pFC3 at the EcoRV site.
5. pFC1-ddh: ~1.3 Kb PstI-EcoRI fragment of pUC18-ddh was cloned into pFC1 cut with PstI and EcoRI.
6. pUC19-P1: ~550 bp HpaI-PvuII fragment (containing the first promoter, P1, of the argS-lysA operon) of pRS6 was cloned into pUC19 at the SmaI site.
7. pUC19-P1lysA: ~1.45 Kb promoterless PCR product, using primer LysA(ATG) and LysA3B, of NRRL-B11474 lysA coding region is cloned into pUC19-P1 at the HincII site.
8. pFC1-P1lysA: ~2 Kb EcoRI-HindIII fragment of pUC19-P1lysA was cloned into pFC1 cut with EcoRI and HindIII.
9. pFC1-P1lysA-ddh: ~1.3 Kb EcoRI-NotI fragment of pFC1-ddh was cloned into pFC1-P1lysA cut with EcoRI and NotI.
10. pFC1-ask-asd-ddh-P1lysA: ~2.6 Kb SwaI-FseI fragment of pFC3-ask-asd was cloned into pFC1-ddh-P1lysA cut with SwaI and FseI.
11. pFC3-ask-asd-dapB-ORF2-dapA-ddh-P1lysA (pFC3-KDABHP1L): ~5.9 Kb SpeI fragment of pFC1-ask-asd-ddh-P1lysA was cloned into pFC3-dapB-ORF2-dapA at the SpeI site.
12. pDElia2-ask-asd-dapB-ORF2-dapA-ddh-P1lysA (pDElia2-KDABHP1L): ~8.8 Kb PmeI fragment of pFC3-ask-asd-dapB-ORF2-dapA-ddh-P1lysA was cloned into pDElia2 at the HincII site.

Primers Used in PCR:

lysA (ATG): CCGGAGAAGATGTAACAATGGCTAC (SEQ ID NO:33)

LysA3B: CCTCGACTGCAGACCCCTAGACACC (SEQ ID NO:34)

The nucleotide sequence (SEQ ID NO:17) of the HpaI-PvuII fragment containing the promoter P1 is shown in FIG. 20. Results of lysine production in NRRL-B11474 comprising the pDElia2-ask-asd-dapA-ORF2-dapB-ddh-P1lysA (pDElia2 KDABHP1L) construct are shown below.

| Strain tested | lysine titer | lysine yield (%) | cell deposit |
|---|---|---|---|
| NRRL-B11474 | 30 | 35 | |
| NRRL-B11474::pDElia2-KDABHP1L | 37 | 42.5 | NRRL B30359 |

Example 8

This example demonstrates the use of vector pDElia2$_{FC5}$-ask-asd-dapB-ddh-lysA (pDElia2$_{FC5}$KDBHL) in the construction of the high yield cell lines of the invention. The pDElia2$_{FC5}$KDBHL vector comprises a truncated ORF2 gene and lacks a dapA gene. The ORF2 gene was cleaved at an internal ClaI site, removing the 3' region and the dapA gene. A promoterless lysA gene was obtained from NRRL-B11474. For cell transformation experiments with the isolated nucleic acid molecules of the invention, the growth preparation of competent cells, and determining of relative growth may be done according to the procedure set forth above. Applicants performed the following steps in constructing the following vectors used in the L-lysine biosynthetic pathway.

1. pGEMT-ask-asd: ~2.6 Kb PCR product containing the ask-asd operon of ATCC21529 using primers ask and asd was cloned into pGEM-T (Promega pGEM-T vector systems).

2. pFC3-ask-asd: ~2.6 Kb NsiI-ApaI fragment of pGEMT-ask-asd was cloned into pFC3 cut with PstI and ApaI.
3. pFC3-dapB-ORF2-dapA: ~2.9 Kb PCR product of NRRL-B11474 dapB-ORF2-dapA coding region was cloned into pFC3 at the EcoRV site.
4. pFC3-dapB: the large ClaI fragment of pFC3-dapB-ORF2-dapA was religated.
5. pUC18-ddh: ~1.3 Kb KpnI fragment of pADM21 containing ddh (NRRL-B11474 locus) was subcloned into pUC18 at the KpnI site.
6. pFC1-ddh: ~1.3 Kb SalI-EcoRI fragment of pUC18-ddh was cloned into pFC1 cut with SalI and EcoRI.
7. pFC1-ddh-lysA: ~2.1 Kb EcoRI-PstI fragment (containing the intact lysA DNA) of pRS6 was clone into pFC1-ddh cut with EcoRI and PstI.
8. pFC1-ask-asd-ddh-lysA: ~2.6 Kb SwaI-FseI fragment of pFC3-ask-asd was cloned into pFC1-ddh-lysA cut with SwaI and FseI.
9. pFC3-ask-asd-dapB-ddh-lysA: ~6 Kb SpeI fragment of pFC1-ask-asd-ddh-lysA was cloned into pFC3-dapB at the SpeI site.
10. pDElia2$_{FC5}$-ask-asd-dapB-ddh-lysA (pDElia2$_{FC5}$-KDBHL): ~7.3 Kb NotI-PmeI fragment of pFC3-ask-asd-dapB-ddh-lysA was cloned into pDElia2$_{FC5}$ cut with NotI and PmeI.
11. pDElia2$_{FC5}$: the small PvuII fragment of pFC5 was ligated with the large PvuII fragment of pDElia2.

Results of lysine production in NRRL-B11474 comprising the pDElia2$_{FC5}$-ask-asd-dapB-ddh-lysA (pDElia2$_{FC5}$KDBHL) are shown below.

| Strain tested | lysine titer | lysine yield (%) | cell deposit |
|---|---|---|---|
| NRRL-B11474 | 31 | 49 | |
| NRRL-B11474::pDElia2$_{FC5}$-KDBHL | 37.8 | 58 | NRRL B30360 |

Having now fully described the present invention in some detail by way of illustration and example for purposes of clarity of understanding, it will be obvious to one of ordinary skill in the art that same can be performed by modifying or changing the invention with a wide and equivalent range of conditions, formulations and other parameters thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. An isolated polynucleotide molecule comprising a nucleotide sequence encoding the polypeptide sequence of SEQ ID NO:2.

2. The isolated polynucleotide molecule of claim 1 comprising a nucleic acid having the sequence of SEQ ID NO:1.

3. A vector comprising the isolated polynucleotide molecule of claim 1.

4. A host cell comprising the vector of claim 3.

5. The isolated polynucleotide molecule of claim 1 further comprising a promoter sequence where said promoter sequence has at least 95% sequence identity to SEQ ID NO: 17, wherein said promoter sequence controls expression of said polynucleotide.

6. The polynucleotide of claim 5 where said promoter sequence has the nucleotide sequence of SEQ ID NO: 17.

7. A vector comprising the isolated polynucleotide of claim 5.

8. A host cell comprising the vector of claim 7.

9. The host cell of claim 8 wherein said host cell is NRRL B 30359.

10. A method for transforming a *Corynebacterium* species host cell comprising:
   (a) transforming a *Corynebacterium* species host cell with the polynucleotide molecule of claim 5, and
   (b) selecting a transformed host cell.

11. An isolated polynucleotide molecule comprising:
   (a) the polynucleotide molecule of claim 1; and
   (b) at least one additional *Corynebacterium* species lysine pathway gene selected from the group consisting of:
      (i) a nucleic acid molecule encoding the asd polypeptide of SEQ ID NO:4;
      (ii) a nucleic acid molecule encoding the dapA polypeptide of SEQ ID NO:6;
      (iii) a nucleic acid molecule encoding the dapB polypeptide of SEQ ID NO:8;

(iv) a nucleic acid molecule encoding the ddh polypeptide of SEQ ID NO:10;
(v) a nucleic acid molecule encoding the 'lysA polypeptide of SEQ ID NO:21;
(vi) a nucleic acid molecule encoding the lysA polypeptide of SEQ ID NO:14; and
(vii) a nucleic acid molecule encoding the ORF2 polypeptide of SEQ ID NO:16.

12. A vector comprising the polynucleotide molecule of claim 11.

13. A host cell comprising the vector of claim 12.

14. The host cell of claim 13 wherein said host cell is a *Brevibacterium flavum* selected from the group consisting of *Brevibacterium flavum* NRRL-B30218, *Brevibacterium flavum* NRRL-B30219, *Brevibacterium lactofermentum* NRRL-B30220, *Brevibacterium lactofermentum* NRRL-B30221, *Brevibacterium lactofermentum* NRRL-B30222, *Brevibacterium flavum* NRRL-B30234 and *Brevibacterium lactofermentum* NRRL-B30235.

15. The host cell of claim 13 wherein said host cell is *Escherichia coli* DH5 α MCR NRRL-B30228.

16. The host cell of claim 13 wherein said host cell is a C.glutamicum selected from the group consisting of C.glutamicum NRRL-B30236 and C.glutamicum NRRL-B30237.

17. The isolated polynucleotide of claim 11, wherein said additional *Corynebacterium* species lysine pathway gene encodes the asd polypeptide of SEQ ID NO:4.

18. The isolated polynucleotide of claim 11, wherein said additional *Corynebacterium* species lysine pathway gene encodes the dapA polypeptide of SEQ ID NO:6.

19. The isolated polynucleotide of claim 11, wherein said additional *Corynebacterium* species lysine pathway gene encodes the dapB polypeptide of SEQ ID NO:8.

20. The isolated polynucleotide of claim 11, wherein said additional *Corynebacterium* species lysine pathway gene encodes the ddh polypeptide of SEQ ID NO:10.

21. The isolated polynucleotide of claim 11, wherein said additional *Corynebacterium* species lysine pathway gene encodes the 'lysA polypeptide of SEQ ID NO:21.

22. The isolated polynucleotide of claim 11, wherein said additional *Corynebacterium* species lysine pathway gene encodes the lysA polypeptide of SEQ ID NO:14.

23. The isolated polynucleotide of claim 11, wherein said additional *Corynebacterium* species lysine pathway gene encodes the ORF2 polypeptide of SEQ ID NO:16.

24. An isolated polynucleotide molecule comprising:
(a) the polynucleotide molecule of claim 1;
(b) a nucleic acid molecule encoding the asd amino acid sequence of SEQ ID NO:4;
(c) a nucleic acid molecule encoding the dapA amino acid sequence of SEQ ID NO:6;
(d) a nucleic acid molecule encoding the dapB amino acid sequence of SEQ ID NO:8; and
(e) a nucleic acid molecule encoding the ORF2 amino acid sequence of SEQ ID NO:16.

25. The isolated polynucleotide molecule of claim 24 comprising pK 184-KDAB.

26. An isolated polynucleotide molecule comprising:
(a) the polynucleotide molecule of claim 1;
(b) a nucleic acid molecule encoding the asd amino acid sequence of SEQ ID NO:4;
(c) a nucleic acid molecule encoding the dapA amino acid sequence of SEQ ID NO:6;
(d) a nucleic acid molecule encoding the dapB amino acid sequence of SEQ ID NO:8;
(e) a nucleic acid molecule encoding the ddh amino acid sequence of SEQ ID NO:10; and
(f) a nucleic acid molecule encoding the ORF2 amino acid sequence of SEQ ID NO:16.

27. An isolated polynucleotide molecule comprising:
(a) the polynucleotide molecule of claim 1;
(b) a nucleic acid molecule encoding the asd amino acid sequence of SEQ ID NO:4;
(c) a nucleic acid molecule encoding the dapA amino acid sequence of SEQ ID NO:6;
(d) a nucleic acid molecule encoding the dapB amino acid sequence of SEQ ID NO:8;
(e) a nucleic acid molecule encoding the ddh amino acid sequence of SEQ ID NO:10;
(f) a nucleic acid molecule encoding the 'lysA amino acid sequence of SEQ ID NO:21; and
(g) a nucleic acid molecule encoding the ORF2 amino acid sequence of SEQ ID NO:16.

28. The isolated polynucleotide molecule of claim 27 comprising pD11-KDABH'L.

29. An isolated polynucleotide molecule comprising:
(a) the polynucleotide molecule of claim 2;
(b) a nucleic acid molecule encoding the asd amino acid sequence of SEQ ID NO:4;
(c) a nucleic acid molecule encoding the dapA amino acid sequence of SEQ ID NO:6;
(d) a nucleic acid molecule encoding the dapB amino acid sequence of SEQ ID NO:8;
(e) a nucleic acid molecule encoding the ddh amino acid sequence of SEQ ID NO:10;
(f) a nucleic acid molecule encoding the lysA amino acid sequence of SEQ ID NO:14; and
(g) a nucleic acid molecule encoding the ORF2 amino acid sequence of SEQ ID NO:16.

30. The isolated polynucleotide molecule of claim 29 comprising pD2-KDABHL.

31. A method for transforming a Corynebacterium species host cell comprising:
(a) transforming a Corynebacterium species host cell with an isolated polynucleotide molecule comprising a nucleotide sequence encoding the polypeptide of SEQ ID NO:2 and
(b) selecting a transformed host cell.

32. The method of claim 31 further comprising screening for said transformed polynucleotide molecule.

33. The method of claim 31 further comprising:
(a) growing said transformed host cell in a medium; and
(b) purifying an amino acid produced by said transformed host cell.

34. The method of claim 31 wherein the nucleotide sequence is integrated into said host cell's chromosome.

35. The method of claim 31 wherein said host cell possesses at least one of the following activities:
(a) aspartate-semialdehyde dehydrogenase activity;
(b) dihydrodipicolinate synthase activity;
(c) dihydrodipicolinate reductase activity;
(d) diaminopimelate dehydrogenase activity; and
(e) diaminopimelate decarboxylase activity.

36. The method of claim 35 further comprising screening for said activity.

37. The method of claim 35 wherein said activity is aspartate-semialdehyde dehydrogenase activity.

38. The method of claim 37, wherein said aspartate-semialdehyde dehydrogenase activity is produced by the asd polypeptide encoded by the polynucleotide of SEQ ID NO:3.

39. The method of claim 35 wherein said activity is dihydrodipicolinate synthase activity.

40. The method of claim 39, wherein said dihydrodipicolinate synthase activity is produced by the dapA polypeptide encoded by the polynucleotide of SEQ ID NO:5.

41. The method of claim 35 wherein said activity is dihydrodipicolinate reductase activity.

42. The method of claim 41, wherein said dihydrodipicolinate reductase activity is produced by the dapB polypeptide encoded by the polynucleotide of SEQ ID NO:7.

43. The method of claim 35 wherein said activity is diaminopimelate dehydrogenase activity.

44. The method of claim 43, wherein said diaminopimelate dehydrogenase activity is produced by the ddh polypeptide encoded by the polynucleotide of SEQ ID NO:9.

45. The method of claim 35 wherein said activity is diaminopimelate decarboxylase activity.

46. The method of claim 45, wherein said diaminopimelate decarboxylase activity is produced by the 'lysA polypeptide encoded by the polynucleotide of SEQ ID NO:20.

47. The method of claim 45, wherein said diaminopimelate decarboxylase activity is produced by the lysA polypeptide encoded by the polynucleotide of SEQ ID NO:13.

48. The method of claim 31, wherein said isolated polynucleotide molecules further comprises at least one nucleic acid molecule selected from the group consisting of:
   a) a nucleic acid molecule encoding the asd amino acid sequence of SEQ ID NO:4;
   b) a nucleic acid molecule encoding the dapA amino acid sequence of SEQ ID NO:6;
   c) a nucleic acid molecule encoding the dapB amino acid sequence of SEQ ID NO:8;
   d) a nucleic acid molecule encoding the ddh amino acid sequence of SEQ ID NO:10;
   e) a nucleic acid molecule encoding the 'lysA amino acid sequence of SEQ ID NO:21;
   f) a nucleic acid molecule encoding the lysA amino acid sequence of SEQ ID NO:14; and
   (g) a nucleic acid molecule encoding the ORF2 amino acid sequence of SEQ ID NO:16.

49. The method of claim 31, wherein said isolated polynucleotide molecule further comprises the following:
   (a) a nucleic acid molecule encoding the asd amino acid sequence of SEQ ID NO:4;
   (b) a nucleic acid molecule encoding the dapA amino acid sequence of SEQ ID NO:6;
   (c) a nucleic acid molecule encoding the dapB amino acid sequence of SEQ ID NO:8; and
   (d) a nucleic acid molecule encoding the ORF2 amino acid sequence of SEQ ID NO:16.

50. The method of claim 31, wherein said isolated polynucleotide molecule further comprises the following:
   (a) a nucleic acid molecule encoding the asd amino acid sequence of SEQ ID NO:4;
   (b) a nucleic acid molecule encoding the dapA amino acid sequence of SEQ ID NO:6;
   (c) a nucleic acid molecule encoding the dapB amino acid sequence of SEQ ID NO:8;
   (d) a nucleic acid molecule encoding the ddh amino acid sequence of SEQ ID NO: 10; and
   (e) a nucleic acid molecule encoding the ORF2 amino acid sequence of SEQ ID NO:16.

51. The method of claim 31, wherein said isolated polynucleotide molecule further comprises the following:
   (a) a nucleic acid molecule encoding the asd amino acid sequence of SEQ ID NO:4;
   (b) a nucleic acid molecule encoding the dapA amino acid sequence of SEQ ID NO:6;
   (c) a nucleic acid molecule encoding the dapB amino acid sequence of SEQ ID NO:8;
   (d) a nucleic acid molecule encoding the ddh amino acid sequence of SEQ ID NO:10;
   (e) a nucleic acid molecule encoding the 'lysA amino acid sequence of SEQ ID NO:21; and
   (f) a nucleic acid molecule encoding the ORF2 amino acid sequence of SEQ ID NO:16.

52. The method of claim 31, wherein said isolated polynucleotide molecule further comprises the following:
   (a) a nucleic acid molecule encoding the asd amino acid sequence of SEQ ID NO:4;
   (b) a nucleic acid molecule encoding the dapA amino acid sequence of SEQ ID NO:6;
   (c) a nucleic acid molecule encoding the dapB amino acid sequence of SEQ ID NO:8;
   (d) a nucleic acid molecule encoding the ddh amino acid sequence of SEQ ID NO:10;
   (e) a nucleic acid molecule encoding the lysA amino acid sequence of SEQ ID NO:14; and
   (f) a nucleic acid molecule encoding the ORF2 amino acid sequence of SEQ ID NO:16.

* * * * *

SEQUENCE LISTING

<160> NUMBER OF SEQ ID NOS: 37

<210> SEQ ID NO 1
<211> LENGTH: 1266
<212> TYPE: DNA
<213> ORGANISM: Corynebacterium glutamicum
<220> FEATURE:
<221> NAME/KEY: CDS
<222> LOCATION: (1)..(1266)

<400> SEQUENCE: 1

```
gtg gcc ctg gtc gta cag aaa tat ggc ggt tcc tcg ctt gag agt gcg      48
Met Ala Leu Val Val Gln Lys Tyr Gly Gly Ser Ser Leu Glu Ser Ala
1               5                   10                  15 gaa cgc att aga aac gtc gct gaa cgg atc gtt gcc acc aag aag gct      96
Glu Arg Ile Arg Asn Val Ala Glu Arg Ile Val Ala Thr Lys Lys Ala
                20                  25                  30 gga aat gat gtc gtg gtt gtc tgc tcc gca atg gga gac acc acg gat     144
Gly Asn Asp Val Val Val Val Cys Ser Ala Met Gly Asp Thr Thr Asp
            35                  40                  45 gaa ctt cta gaa ctt gca gcg gca gtg aat ccc gtt ccg cca gct cgt     192
Glu Leu Leu Glu Leu Ala Ala Ala Val Asn Pro Val Pro Pro Ala Arg
        50                  55                  60 gaa atg gat atg ctc ctg act gct ggt gag cgt att tct aac gct ctc     240
Glu Met Asp Met Leu Leu Thr Ala Gly Glu Arg Ile Ser Asn Ala Leu
65                  70                  75                  80 gtc gcc atg gct att gag tcc ctt ggc gca gaa gct caa tct ttc act     288
Val Ala Met Ala Ile Glu Ser Leu Gly Ala Glu Ala Gln Ser Phe Thr
                85                  90                  95 ggc tct cag gct ggt gtg ctc acc acc gag cgc cac gga aac gca cgc     336
Gly Ser Gln Ala Gly Val Leu Thr Thr Glu Arg His Gly Asn Ala Arg
```

-continued

```
               100                      105                      110
att gtt gac gtc aca ccg ggt cgt gtg cgt gaa gca ctc gat gag ggc      384
Ile Val Asp Val Thr Pro Gly Arg Val Arg Glu Ala Leu Asp Glu Gly
            115                      120                      125 aag atc tgc att gtt gct ggt ttt cag ggt gtt aat aaa gaa acc cgc      432
Lys Ile Cys Ile Val Ala Gly Phe Gln Gly Val Asn Lys Glu Thr Arg
        130                      135                      140 gat gtc acc acg ttg ggt cgt ggt ggt tct gac acc act gca gtt gcg      480
Asp Val Thr Thr Leu Gly Arg Gly Gly Ser Asp Thr Thr Ala Val Ala
145                      150                      155                      160 ttg gca gct gct ttg aac gct gat gtg tgt gag att tac tcg gac gtt      528
Leu Ala Ala Ala Leu Asn Ala Asp Val Cys Glu Ile Tyr Ser Asp Val
                    165                      170                      175 gac ggt gtg tat acc gct gac ccg cgc atc gtt cct aat gca cag aag      576
Asp Gly Val Tyr Thr Ala Asp Pro Arg Ile Val Pro Asn Ala Gln Lys
                180                      185                      190 ctg gaa aag ctc agc ttc gaa gaa atg ctg gaa ctt gct gct gtt ggc      624
Leu Glu Lys Leu Ser Phe Glu Glu Met Leu Glu Leu Ala Ala Val Gly
            195                      200                      205 tcc aag att ttg gtg ctg cgc agt gtt gaa tac gct cgt gca ttc aat      672
Ser Lys Ile Leu Val Leu Arg Ser Val Glu Tyr Ala Arg Ala Phe Asn
        210                      215                      220 gtg cca ctt cgc gta cgc tcg tct tat agt aat gat ccc ggc act ttg      720
Val Pro Leu Arg Val Arg Ser Ser Tyr Ser Asn Asp Pro Gly Thr Leu
225                      230                      235                      240 att gcc ggc tct atg gag gat att cct gtg gaa gaa gca gtc ctt acc      768
Ile Ala Gly Ser Met Glu Asp Ile Pro Val Glu Glu Ala Val Leu Thr
                    245                      250                      255 ggt gtc gca acc gac aag tcc gaa gcc aaa gta acc gtt ctg ggt att      816
Gly Val Ala Thr Asp Lys Ser Glu Ala Lys Val Thr Val Leu Gly Ile
                260                      265                      270 tcc gat aag cca ggc gag gct gcc aag gtt ttc cgt gcg ttg gct gat      864
Ser Asp Lys Pro Gly Glu Ala Ala Lys Val Phe Arg Ala Leu Ala Asp
            275                      280                      285 gca gaa atc aac att gac atg gtt ctg cag aac gtc tcc tct gtg gaa      912
Ala Glu Ile Asn Ile Asp Met Val Leu Gln Asn Val Ser Ser Val Glu
        290                      295                      300 gac ggc acc acc gac atc acg ttc acc tgc cct cgc gct gac gga cgc      960
Asp Gly Thr Thr Asp Ile Thr Phe Thr Cys Pro Arg Ala Asp Gly Arg
305                      310                      315                      320 cgt gcg atg gag atc ttg aag aag ctt cag gtt cag ggc aac tgg acc     1008
Arg Ala Met Glu Ile Leu Lys Lys Leu Gln Val Gln Gly Asn Trp Thr
                    325                      330                      335 aat gtg ctt tac gac gac cag gtc ggc aaa gtc tcc ctc gtg ggt gct     1056
Asn Val Leu Tyr Asp Asp Gln Val Gly Lys Val Ser Leu Val Gly Ala
                340                      345                      350 ggc atg aag tct cac cca ggt gtt acc gca gag ttc atg gaa gct ctg     1104
Gly Met Lys Ser His Pro Gly Val Thr Ala Glu Phe Met Glu Ala Leu
            355                      360                      365 cgc gat gtc aac gtg aac atc gaa ttg att tcc atc tct gag atc cgc     1152
Arg Asp Val Asn Val Asn Ile Glu Leu Ile Ser Ile Ser Glu Ile Arg
        370                      375                      380 att tcc gtg ctg atc cgt gaa gat gat ctg gat gct gct gca cgt gca     1200
Ile Ser Val Leu Ile Arg Glu Asp Asp Leu Asp Ala Ala Ala Arg Ala
385                      390                      395                      400 ttg cat gag cag ttc cag ctg ggc ggc gaa gac gaa gcc gtc gtt tat     1248
Leu His Glu Gln Phe Gln Leu Gly Gly Glu Asp Glu Ala Val Val Tyr
                    405                      410                      415 gca ggc acc gga cgc taa                                              1266
```

Ala Gly Thr Gly Arg
             420

<210> SEQ ID NO 2
<211> LENGTH: 421
<212> TYPE: PRT
<213> ORGANISM: Corynebacterium glutamicum

<400> SEQUENCE: 2

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ala Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

```
Arg Asp Val Asn Val Asn Ile Glu Leu Ile Ser Ile Ser Glu Ile Arg
    370                 375                 380

Ile Ser Val Leu Ile Arg Glu Asp Asp Leu Asp Ala Ala Arg Ala
385                 390                 395                 400

Leu His Glu Gln Phe Gln Leu Gly Gly Glu Asp Glu Ala Val Val Tyr
                    405                 410                 415

Ala Gly Thr Gly Arg
            420

<210> SEQ ID NO 3
<211> LENGTH: 1035
<212> TYPE: DNA
<213> ORGANISM: Corynebacterium glutamicum
<220> FEATURE:
<221> NAME/KEY: CDS
<222> LOCATION: (1)..(1035)

<400> SEQUENCE: 3 atg acc acc atc gca gtt gtt ggt gca acc ggc cag gtc ggc cag gtt      48
Met Thr Thr Ile Ala Val Val Gly Ala Thr Gly Gln Val Gly Gln Val
1               5                   10                  15 atg cgc acc ttt ttg gaa gag cgc aat ttc cca gct gac act gtt cgt      96
Met Arg Thr Phe Leu Glu Glu Arg Asn Phe Pro Ala Asp Thr Val Arg
                20                  25                  30 ttc ttt gct tcc ccg cgt tcc gca ggc cgt aag att gaa ttc cgt ggc     144
Phe Phe Ala Ser Pro Arg Ser Ala Gly Arg Lys Ile Glu Phe Arg Gly
            35                  40                  45 acg gaa atc gag gta gaa gac att act cag gca acc gag gag tcc ctc     192
Thr Glu Ile Glu Val Glu Asp Ile Thr Gln Ala Thr Glu Glu Ser Leu
        50                  55                  60 aag ggc atc gac gtt gcg ttg ttc tct gct gga ggc acc gct tcc aag     240
Lys Gly Ile Asp Val Ala Leu Phe Ser Ala Gly Gly Thr Ala Ser Lys
65                  70                  75                  80 cag tac gct cca ctg ttt gct gct gca ggc gcg act gtt gtg gat aac     288
Gln Tyr Ala Pro Leu Phe Ala Ala Ala Gly Ala Thr Val Val Asp Asn
                85                  90                  95 tct tct gct tgg cgc aag gac gac gag gtt cca cta atc gtc tct gag     336
Ser Ser Ala Trp Arg Lys Asp Asp Glu Val Pro Leu Ile Val Ser Glu
            100                 105                 110 gtg aac cct tcc gac aag gat tcc ctg gtc aag ggc att att gcg aat     384
Val Asn Pro Ser Asp Lys Asp Ser Leu Val Lys Gly Ile Ile Ala Asn
        115                 120                 125 cct aac tgc acc acc atg gct gca atg cca gtg ctg aag cca ctg cac     432
Pro Asn Cys Thr Thr Met Ala Ala Met Pro Val Leu Lys Pro Leu His
130                 135                 140 gat gcc gct ggt ctt gta aag ctt cac gtt tcc tct tac cag gct gtt     480
Asp Ala Ala Gly Leu Val Lys Leu His Val Ser Ser Tyr Gln Ala Val
145                 150                 155                 160 tcc ggt tct ggt ctt gca ggt gtg gaa acc ttg gca aag cag gtt gct     528
Ser Gly Ser Gly Leu Ala Gly Val Glu Thr Leu Ala Lys Gln Val Ala
                165                 170                 175 gca gtt ggc gac cac aac gtt gag ttc gtc cat gat gga cag gct gct     576
Ala Val Gly Asp His Asn Val Glu Phe Val His Asp Gly Gln Ala Ala
            180                 185                 190 gac gca ggc gat gtc gga cct tac gtt tcc cca atc gct tac aac gtg     624
Asp Ala Gly Asp Val Gly Pro Tyr Val Ser Pro Ile Ala Tyr Asn Val
        195                 200                 205 ctg cca ttc gcc gga aac ctc gtc gat gac ggc acc ttc gaa acc gac     672
Leu Pro Phe Ala Gly Asn Leu Val Asp Asp Gly Thr Phe Glu Thr Asp
210                 215                 220
```

```
gaa gag cag aag ctg cgc aac gaa tcc cgc aag att ctc ggc ctc cca      720
Glu Glu Gln Lys Leu Arg Asn Glu Ser Arg Lys Ile Leu Gly Leu Pro
225                 230                 235                 240 gac ctc aag gtc tca ggc acc tgc gtc cgc gtg ccg gtt ttc acc ggc      768
Asp Leu Lys Val Ser Gly Thr Cys Val Arg Val Pro Val Phe Thr Gly
                245                 250                 255 cac acg ctg acc att cac gcc gaa ttc gac aag gca atc acc gtc gag      816
His Thr Leu Thr Ile His Ala Glu Phe Asp Lys Ala Ile Thr Val Glu
            260                 265                 270 cag gcg cag gag atc ttg ggt gcc gct tca ggc gtc gag ctt gtc gac      864
Gln Ala Gln Glu Ile Leu Gly Ala Ala Ser Gly Val Glu Leu Val Asp
        275                 280                 285 gtc cca acc cca ctt gca gct gcc ggc att gac gaa tcc ctc gtt gga      912
Val Pro Thr Pro Leu Ala Ala Ala Gly Ile Asp Glu Ser Leu Val Gly
    290                 295                 300 cgc atc cgt cag gac tcc act gtc gac gac aac cgc ggt ctg gtt ctc      960
Arg Ile Arg Gln Asp Ser Thr Val Asp Asp Asn Arg Gly Leu Val Leu
305                 310                 315                 320 gtc gta tct ggc gat aac ctt cgc aag ggc gca gca ctg aac acc att     1008
Val Val Ser Gly Asp Asn Leu Arg Lys Gly Ala Ala Leu Asn Thr Ile
                325                 330                 335 cag att gct gag ctg ctg gtt aag taa                                  1035
Gln Ile Ala Glu Leu Leu Val Lys
            340
```

<210> SEQ ID NO 4
<211> LENGTH: 344
<212> TYPE: PRT
<213> ORGANISM: Corynebacterium glutamicum

<400> SEQUENCE: 4

```
Met Thr Thr Ile Ala Val Val Gly Ala Thr Gly Gln Val Gly Gln Val
1               5                   10                  15

Met Arg Thr Phe Leu Glu Glu Arg Asn Phe Pro Ala Asp Thr Val Arg
            20                  25                  30

Phe Phe Ala Ser Pro Arg Ser Ala Gly Arg Lys Ile Glu Phe Arg Gly
        35                  40                  45

Thr Glu Ile Glu Val Glu Asp Ile Thr Gln Ala Thr Glu Glu Ser Leu
    50                  55                  60

Lys Gly Ile Asp Val Ala Leu Phe Ser Ala Gly Gly Thr Ala Ser Lys
65                  70                  75                  80

Gln Tyr Ala Pro Leu Phe Ala Ala Gly Ala Thr Val Val Asp Asn
            85                  90                  95

Ser Ser Ala Trp Arg Lys Asp Asp Glu Val Pro Leu Ile Val Ser Glu
            100                 105                 110

Val Asn Pro Ser Asp Lys Asp Ser Leu Val Lys Gly Ile Ile Ala Asn
        115                 120                 125

Pro Asn Cys Thr Thr Met Ala Ala Met Pro Val Leu Lys Pro Leu His
    130                 135                 140

Asp Ala Ala Gly Leu Val Lys Leu His Val Ser Ser Tyr Gln Ala Val
145                 150                 155                 160

Ser Gly Ser Gly Leu Ala Gly Val Glu Thr Leu Ala Lys Gln Val Ala
                165                 170                 175

Ala Val Gly Asp His Asn Val Glu Phe Val His Asp Gly Gln Ala Ala
            180                 185                 190

Asp Ala Gly Asp Val Gly Pro Tyr Val Ser Pro Ile Ala Tyr Asn Val
        195                 200                 205
```

```
Leu Pro Phe Ala Gly Asn Leu Val Asp Asp Gly Thr Phe Glu Thr Asp
        210                 215                 220

Glu Glu Gln Lys Leu Arg Asn Glu Ser Arg Lys Ile Leu Gly Leu Pro
225                 230                 235                 240

Asp Leu Lys Val Ser Gly Thr Cys Val Arg Val Pro Val Phe Thr Gly
                245                 250                 255

His Thr Leu Thr Ile His Ala Glu Phe Asp Lys Ala Ile Thr Val Glu
            260                 265                 270

Gln Ala Gln Glu Ile Leu Gly Ala Ala Ser Gly Val Glu Leu Val Asp
        275                 280                 285

Val Pro Thr Pro Leu Ala Ala Ala Gly Ile Asp Glu Ser Leu Val Gly
    290                 295                 300

Arg Ile Arg Gln Asp Ser Thr Val Asp Asp Asn Arg Gly Leu Val Leu
305                 310                 315                 320

Val Val Ser Gly Asp Asn Leu Arg Lys Gly Ala Ala Leu Asn Thr Ile
                325                 330                 335

Gln Ile Ala Glu Leu Leu Val Lys
            340

<210> SEQ ID NO 5
<211> LENGTH: 906
<212> TYPE: DNA
<213> ORGANISM: Corynebacterium glutamicum
<220> FEATURE:
<221> NAME/KEY: CDS
<222> LOCATION: (1)..(906)

<400> SEQUENCE: 5 atg agc aca ggt tta aca gct aag acc gga gta gag cac ttc ggc acc      48
Met Ser Thr Gly Leu Thr Ala Lys Thr Gly Val Glu His Phe Gly Thr
1               5                   10                  15 gtt gga gta gca atg gtt act cca ttc acg gaa tcc gga gac atc gat      96
Val Gly Val Ala Met Val Thr Pro Phe Thr Glu Ser Gly Asp Ile Asp
                20                  25                  30 atc gct gct ggc cgc gaa gtc gcg gct tat ttg gtt gat aag ggc ttg     144
Ile Ala Ala Gly Arg Glu Val Ala Ala Tyr Leu Val Asp Lys Gly Leu
            35                  40                  45 gat tct ttg gtt ctc gcg ggc acc act ggt gaa tcc cca acg aca acc     192
Asp Ser Leu Val Leu Ala Gly Thr Thr Gly Glu Ser Pro Thr Thr Thr
        50                  55                  60 gcc gct gaa aaa cta gaa ctg ctc aag gcc gtt cgt gag gaa gtt ggg     240
Ala Ala Glu Lys Leu Glu Leu Leu Lys Ala Val Arg Glu Glu Val Gly
65                  70                  75                  80 gat cgg gcg aag ctc atc gcc ggt gtc gga acc aac aac acg cgg aca     288
Asp Arg Ala Lys Leu Ile Ala Gly Val Gly Thr Asn Asn Thr Arg Thr
                85                  90                  95 tct gtg gaa ctt gcg gaa gct gct gct tct gct ggc gca gac ggc ctt     336
Ser Val Glu Leu Ala Glu Ala Ala Ala Ser Ala Gly Ala Asp Gly Leu
            100                 105                 110 tta gtt gta act cct tat tac tcc aag ccg agc caa gag gga ttg ctg     384
Leu Val Val Thr Pro Tyr Tyr Ser Lys Pro Ser Gln Glu Gly Leu Leu
        115                 120                 125 gcg cac ttc ggt gca att gct gca gca aca gag gtt cca att tgt ctc     432
Ala His Phe Gly Ala Ile Ala Ala Ala Thr Glu Val Pro Ile Cys Leu
    130                 135                 140 tat gac att cct ggt cgg tca ggt att cca att gaa tct gat acc atg     480
Tyr Asp Ile Pro Gly Arg Ser Gly Ile Pro Ile Glu Ser Asp Thr Met
145                 150                 155                 160
```

```
aga cgc ctg agt gaa tta cct acg att ttg gcg gtc aag gac gcc aag     528
Arg Arg Leu Ser Glu Leu Pro Thr Ile Leu Ala Val Lys Asp Ala Lys
            165                 170                 175 ggt gac ctc gtt gca gcc acg tca ttg atc aaa gaa acg gga ctt gcc     576
Gly Asp Leu Val Ala Ala Thr Ser Leu Ile Lys Glu Thr Gly Leu Ala
        180                 185                 190 tgg tat tca ggc gat gac cca cta aac ctt gtt tgg ctt gct ttg ggc     624
Trp Tyr Ser Gly Asp Asp Pro Leu Asn Leu Val Trp Leu Ala Leu Gly
    195                 200                 205 gga tca ggt ttc att tcc gta att gga cat gca gcc ccc aca gca tta     672
Gly Ser Gly Phe Ile Ser Val Ile Gly His Ala Ala Pro Thr Ala Leu
210                 215                 220 cgt gag ttg tac aca agc ttc gag gaa ggc gac ctc gtc cgt gcg cgg     720
Arg Glu Leu Tyr Thr Ser Phe Glu Glu Gly Asp Leu Val Arg Ala Arg
225                 230                 235                 240 gaa atc aac gcc aaa cta tca ccg ctg gta gct gcc caa ggt cgc ttg     768
Glu Ile Asn Ala Lys Leu Ser Pro Leu Val Ala Ala Gln Gly Arg Leu
                245                 250                 255 ggt gga gtc agc ttg gca aaa gct gct ctg cgt ctg cag ggc atc aac     816
Gly Gly Val Ser Leu Ala Lys Ala Ala Leu Arg Leu Gln Gly Ile Asn
            260                 265                 270 gta gga gat cct cga ctt cca att atg gct cca aat gag cag gaa ctt     864
Val Gly Asp Pro Arg Leu Pro Ile Met Ala Pro Asn Glu Gln Glu Leu
        275                 280                 285 gag gct ctc cga gaa gac atg aaa aaa gct gga gtt cta taa             906
Glu Ala Leu Arg Glu Asp Met Lys Lys Ala Gly Val Leu
    290                 295                 300
```

<210> SEQ ID NO 6
<211> LENGTH: 301
<212> TYPE: PRT
<213> ORGANISM: Corynebacterium glutamicum

<400> SEQUENCE: 6

```
Met Ser Thr Gly Leu Thr Ala Lys Thr Gly Val Glu His Phe Gly Thr
1               5                   10                  15

Val Gly Val Ala Met Val Thr Pro Phe Thr Glu Ser Gly Asp Ile Asp
            20                  25                  30

Ile Ala Ala Gly Arg Glu Val Ala Ala Tyr Leu Val Asp Lys Gly Leu
        35                  40                  45

Asp Ser Leu Val Leu Ala Gly Thr Thr Gly Glu Ser Pro Thr Thr Thr
    50                  55                  60

Ala Ala Glu Lys Leu Glu Leu Leu Lys Ala Val Arg Glu Glu Val Gly
65                  70                  75                  80

Asp Arg Ala Lys Leu Ile Ala Gly Val Gly Thr Asn Asn Thr Arg Thr
                85                  90                  95

Ser Val Glu Leu Ala Glu Ala Ala Ala Ser Ala Gly Ala Asp Gly Leu
            100                 105                 110

Leu Val Val Thr Pro Tyr Tyr Ser Lys Pro Ser Gln Glu Gly Leu Leu
        115                 120                 125

Ala His Phe Gly Ala Ile Ala Ala Thr Glu Val Pro Ile Cys Leu
    130                 135                 140

Tyr Asp Ile Pro Gly Arg Ser Gly Ile Pro Ile Glu Ser Asp Thr Met
145                 150                 155                 160

Arg Arg Leu Ser Glu Leu Pro Thr Ile Leu Ala Val Lys Asp Ala Lys
                165                 170                 175

Gly Asp Leu Val Ala Ala Thr Ser Leu Ile Lys Glu Thr Gly Leu Ala
            180                 185                 190
```

-continued

```
Trp Tyr Ser Gly Asp Asp Pro Leu Asn Leu Val Trp Leu Ala Leu Gly
        195                 200                 205
Gly Ser Gly Phe Ile Ser Val Ile Gly His Ala Ala Pro Thr Ala Leu
        210                 215                 220
Arg Glu Leu Tyr Thr Ser Phe Glu Glu Gly Asp Leu Val Arg Ala Arg
225                 230                 235                 240
Glu Ile Asn Ala Lys Leu Ser Pro Leu Ala Ala Gln Gly Arg Leu
                245                 250                 255
Gly Gly Val Ser Leu Ala Lys Ala Ala Leu Arg Leu Gln Gly Ile Asn
            260                 265                 270
Val Gly Asp Pro Arg Leu Pro Ile Met Ala Pro Asn Glu Gln Glu Leu
        275                 280                 285
Glu Ala Leu Arg Glu Asp Met Lys Lys Ala Gly Val Leu
        290                 295                 300
```

<210> SEQ ID NO 7
<211> LENGTH: 747
<212> TYPE: DNA
<213> ORGANISM: Corynebacterium glutamicum
<220> FEATURE:
<221> NAME/KEY: CDS
<222> LOCATION: (1)..(747)

<400> SEQUENCE: 7

```
atg gga atc aag gtt ggc gtt ctc gga gcc aaa ggc cgt gtt ggt caa     48
Met Gly Ile Lys Val Gly Val Leu Gly Ala Lys Gly Arg Val Gly Gln
1               5                   10                  15 act att gtg gca gca gtc aat gag tcc gac gat ctg gag ctt gtt gca     96
Thr Ile Val Ala Ala Val Asn Glu Ser Asp Asp Leu Glu Leu Val Ala
            20                  25                  30 gag atc ggc gtc gac gat gat ttg agc ctt ctg gta gac aac ggc gct    144
Glu Ile Gly Val Asp Asp Asp Leu Ser Leu Leu Val Asp Asn Gly Ala
        35                  40                  45 gaa gtt gtc gtt gac ttc acc act cct aac gct gtg atg ggc aac ctg    192
Glu Val Val Val Asp Phe Thr Thr Pro Asn Ala Val Met Gly Asn Leu
    50                  55                  60 gag ttc tgc atc aac aac ggc att tct gcg gtt gtt gga acc acg ggc    240
Glu Phe Cys Ile Asn Asn Gly Ile Ser Ala Val Val Gly Thr Thr Gly
65                  70                  75                  80 ttc gat aat gct cgt ttg gag cag gtt cgc gcc tgg ctt gaa gga aaa    288
Phe Asp Asn Ala Arg Leu Glu Gln Val Arg Ala Trp Leu Glu Gly Lys
                85                  90                  95 gac aat gtc ggt gtt ctg atc gca cct aac ttt gct atc tct gcg gtg    336
Asp Asn Val Gly Val Leu Ile Ala Pro Asn Phe Ala Ile Ser Ala Val
            100                 105                 110 ttg acc atg gtc ttt tcc aag cag gct gcc cgc ttc ttc gaa tca gct    384
Leu Thr Met Val Phe Ser Lys Gln Ala Ala Arg Phe Phe Glu Ser Ala
        115                 120                 125 gaa gtt att gag ctg cac cac ccc aac aag ctg gat gca cct tca ggc    432
Glu Val Ile Glu Leu His His Pro Asn Lys Leu Asp Ala Pro Ser Gly
    130                 135                 140 acc gcg atc cac act gct cag ggc att gct gcg gca cgc aaa gaa gca    480
Thr Ala Ile His Thr Ala Gln Gly Ile Ala Ala Ala Arg Lys Glu Ala
145                 150                 155                 160 ggc atg gac gca cag cca gat gcg acc gag cag gca ctt gag ggt tcc    528
Gly Met Asp Ala Gln Pro Asp Ala Thr Glu Gln Ala Leu Glu Gly Ser
                165                 170                 175 cgt ggc gca agc gta gat gga atc cca gtt cac gca gtc cgc atg tcc    576
Arg Gly Ala Ser Val Asp Gly Ile Pro Val His Ala Val Arg Met Ser
            180                 185                 190
```

```
                       180                  185                  190
ggc atg gtt gct cac gag caa gtt atc ttt ggc acc cag ggt cag acc          624
Gly Met Val Ala His Glu Gln Val Ile Phe Gly Thr Gln Gly Gln Thr
        195                  200                  205 ttg acc atc aag cag gac tcc tat gat cgc aac tca ttt gca cca ggt          672
Leu Thr Ile Lys Gln Asp Ser Tyr Asp Arg Asn Ser Phe Ala Pro Gly
        210                  215                  220 gtc ttg gtg ggt gtg cgc aac att gca cag cac cca ggc cta gtc gta          720
Val Leu Val Gly Val Arg Asn Ile Ala Gln His Pro Gly Leu Val Val
225                  230                  235                  240 gga ctt gag cat tac cta ggc ctg taa                                      747
Gly Leu Glu His Tyr Leu Gly Leu
                245

<210> SEQ ID NO 8
<211> LENGTH: 248
<212> TYPE: PRT
<213> ORGANISM: Corynebacterium glutamicum

<400> SEQUENCE: 8

Met Gly Ile Lys Val Gly Val Leu Gly Ala Lys Gly Arg Val Gly Gln
1               5                   10                  15

Thr Ile Val Ala Ala Val Asn Glu Ser Asp Asp Leu Glu Leu Val Ala
            20                  25                  30

Glu Ile Gly Val Asp Asp Leu Ser Leu Leu Val Asp Asn Gly Ala
        35                  40                  45

Glu Val Val Val Asp Phe Thr Thr Pro Asn Ala Val Met Gly Asn Leu
    50                  55                  60

Glu Phe Cys Ile Asn Asn Gly Ile Ser Ala Val Val Gly Thr Thr Gly
65                  70                  75                  80

Phe Asp Asn Ala Arg Leu Glu Gln Val Arg Ala Trp Leu Glu Gly Lys
                85                  90                  95

Asp Asn Val Gly Val Leu Ile Ala Pro Asn Phe Ala Ile Ser Ala Val
            100                 105                 110

Leu Thr Met Val Phe Ser Lys Gln Ala Ala Arg Phe Phe Glu Ser Ala
        115                 120                 125

Glu Val Ile Glu Leu His His Pro Asn Lys Leu Asp Ala Pro Ser Gly
    130                 135                 140

Thr Ala Ile His Thr Ala Gln Gly Ile Ala Ala Ala Arg Lys Glu Ala
145                 150                 155                 160

Gly Met Asp Ala Gln Pro Asp Ala Thr Glu Gln Ala Leu Glu Gly Ser
                165                 170                 175

Arg Gly Ala Ser Val Asp Gly Ile Pro Val His Ala Val Arg Met Ser
            180                 185                 190

Gly Met Val Ala His Glu Gln Val Ile Phe Gly Thr Gln Gly Gln Thr
        195                 200                 205

Leu Thr Ile Lys Gln Asp Ser Tyr Asp Arg Asn Ser Phe Ala Pro Gly
    210                 215                 220

Val Leu Val Gly Val Arg Asn Ile Ala Gln His Pro Gly Leu Val Val
225                 230                 235                 240

Gly Leu Glu His Tyr Leu Gly Leu
                245

<210> SEQ ID NO 9
<211> LENGTH: 1023
<212> TYPE: DNA
<213> ORGANISM: Corynebacterium glutamicum
```

US 6,927,046 B1

57 58

-continued

```
<220> FEATURE:
<221> NAME/KEY: CDS
<222> LOCATION: (1)..(1023)

<400> SEQUENCE: 9 atg cat ttc ggt aag ctc gac cag gac agt gcc acc aca att ttg gag      48
Met His Phe Gly Lys Leu Asp Gln Asp Ser Ala Thr Thr Ile Leu Glu
1               5                  10                  15 gat tac aag aac atg acc aac atc cgc gta gct atc gta ggc tac gga      96
Asp Tyr Lys Asn Met Thr Asn Ile Arg Val Ala Ile Val Gly Tyr Gly
            20                  25                  30 aac ctg gga cgc agc gtc gaa aag ctt att gcc aag cag ccc gac atg     144
Asn Leu Gly Arg Ser Val Glu Lys Leu Ile Ala Lys Gln Pro Asp Met
        35                  40                  45 gac ctt gta gga atc ttc tcg cgc cgg gcc acc ctc gac aca aag acg     192
Asp Leu Val Gly Ile Phe Ser Arg Arg Ala Thr Leu Asp Thr Lys Thr
    50                  55                  60 cca gtc ttt gat gtc gcc gac gtg gac aag cac gcc gac gac gtg gac     240
Pro Val Phe Asp Val Ala Asp Val Asp Lys His Ala Asp Asp Val Asp
65                  70                  75                  80 gtg ctg ttc ctg tgc atg ggc tcc gcc acc gac atc cct gag cag gca     288
Val Leu Phe Leu Cys Met Gly Ser Ala Thr Asp Ile Pro Glu Gln Ala
                85                  90                  95 cca aag ttc gcg cag ttc gcc tgc acc gta gac acc tac gac aac cac     336
Pro Lys Phe Ala Gln Phe Ala Cys Thr Val Asp Thr Tyr Asp Asn His
            100                 105                 110 cgc gac atc cca cgc cac cgc cag gtc atg aac gaa gcc gcc acc gca     384
Arg Asp Ile Pro Arg His Arg Gln Val Met Asn Glu Ala Ala Thr Ala
        115                 120                 125 gcc ggc aac gtt gca ctg gtc tct acc ggc tgg gat cca gga atg ttc     432
Ala Gly Asn Val Ala Leu Val Ser Thr Gly Trp Asp Pro Gly Met Phe
    130                 135                 140 tcc atc aac cgc gtc tac gca gcg gca gtc tta gcc gag cac cag cag     480
Ser Ile Asn Arg Val Tyr Ala Ala Ala Val Leu Ala Glu His Gln Gln
145                 150                 155                 160 cac acc ttc tgg ggc cca ggt ttg tca cag ggc cac tcc gat gct ttg     528
His Thr Phe Trp Gly Pro Gly Leu Ser Gln Gly His Ser Asp Ala Leu
                165                 170                 175 cga cgc atc cct ggc gtt caa aag gcc gtc cag tac acc ctc cca tcc     576
Arg Arg Ile Pro Gly Val Gln Lys Ala Val Gln Tyr Thr Leu Pro Ser
            180                 185                 190 gaa gaa gcc ctg gaa aag gcc cgc cgt ggc gaa gcc ggc gac ctc acc     624
Glu Glu Ala Leu Glu Lys Ala Arg Arg Gly Glu Ala Gly Asp Leu Thr
        195                 200                 205 gga aag caa acc cac aag cgc caa tgc ttc gtg gtt gcc gac gcg gcc     672
Gly Lys Gln Thr His Lys Arg Gln Cys Phe Val Val Ala Asp Ala Ala
    210                 215                 220 gac cac gag cgc atc gaa aac gac atc cgc acc atg cct gat tac ttc     720
Asp His Glu Arg Ile Glu Asn Asp Ile Arg Thr Met Pro Asp Tyr Phe
225                 230                 235                 240 gtt ggc tac gaa gtc gaa gtc aac ttc atc gac gaa gca acc ttg gac     768
Val Gly Tyr Glu Val Glu Val Asn Phe Ile Asp Glu Ala Thr Leu Asp
                245                 250                 255 gcc gag cac acc ggc atg cca cac ggc gga cac gtg atc acc acc ggc     816
Ala Glu His Thr Gly Met Pro His Gly Gly His Val Ile Thr Thr Gly
            260                 265                 270 gac acc ggt ggc ttc aac cac acc gtg gaa tac atc ctg aag ctg gac     864
Asp Thr Gly Gly Phe Asn His Thr Val Glu Tyr Ile Leu Lys Leu Asp
        275                 280                 285 cga aac cca gat ttc acc gct tct tca cag atc gct ttc ggc cgc gca     912
```

```
Arg Asn Pro Asp Phe Thr Ala Ser Ser Gln Ile Ala Phe Gly Arg Ala
    290                 295                 300 gct cac cgc atg aag cag cag ggc caa agc ggt gct ttc acc gtc ctc      960
Ala His Arg Met Lys Gln Gln Gly Gln Ser Gly Ala Phe Thr Val Leu
305                 310                 315                 320 gaa gtt gct cca tac ttg ctc tcc ccg gag aac ttg gat gat ctg atc     1008
Glu Val Ala Pro Tyr Leu Leu Ser Pro Glu Asn Leu Asp Asp Leu Ile
                325                 330                 335 gca cgc gac gtc taa                                                 1023
Ala Arg Asp Val
            340

<210> SEQ ID NO 10
<211> LENGTH: 340
<212> TYPE: PRT
<213> ORGANISM: Corynebacterium glutamicum

<400> SEQUENCE: 10

Met His Phe Gly Lys Leu Asp Gln Asp Ser Ala Thr Thr Ile Leu Glu
1               5                   10                  15

Asp Tyr Lys Asn Met Thr Asn Ile Arg Val Ala Ile Val Gly Tyr Gly
            20                  25                  30

Asn Leu Gly Arg Ser Val Glu Lys Leu Ile Ala Lys Gln Pro Asp Met
        35                  40                  45

Asp Leu Val Gly Ile Phe Ser Arg Arg Ala Thr Leu Asp Thr Lys Thr
    50                  55                  60

Pro Val Phe Asp Val Ala Asp Val Asp Lys His Ala Asp Asp Val Asp
65                  70                  75                  80

Val Leu Phe Leu Cys Met Gly Ser Ala Thr Asp Ile Pro Glu Gln Ala
                85                  90                  95

Pro Lys Phe Ala Gln Phe Ala Cys Thr Val Asp Thr Tyr Asp Asn His
            100                 105                 110

Arg Asp Ile Pro Arg His Arg Gln Val Met Asn Glu Ala Ala Thr Ala
        115                 120                 125

Ala Gly Asn Val Ala Leu Val Ser Thr Gly Trp Asp Pro Gly Met Phe
    130                 135                 140

Ser Ile Asn Arg Val Tyr Ala Ala Val Leu Ala Glu His Gln Gln
145                 150                 155                 160

His Thr Phe Trp Gly Pro Gly Leu Ser Gln Gly His Ser Asp Ala Leu
            165                 170                 175

Arg Arg Ile Pro Gly Val Gln Lys Ala Val Gln Tyr Thr Leu Pro Ser
        180                 185                 190

Glu Glu Ala Leu Glu Lys Ala Arg Arg Gly Glu Ala Gly Asp Leu Thr
    195                 200                 205

Gly Lys Gln Thr His Lys Arg Gln Cys Phe Val Val Ala Asp Ala Ala
210                 215                 220

Asp His Glu Arg Ile Glu Asn Asp Ile Arg Thr Met Pro Asp Tyr Phe
225                 230                 235                 240

Val Gly Tyr Glu Val Glu Val Asn Phe Ile Asp Glu Ala Thr Leu Asp
            245                 250                 255

Ala Glu His Thr Gly Met Pro His Gly Gly His Val Ile Thr Thr Gly
        260                 265                 270

Asp Thr Gly Gly Phe Asn His Thr Val Glu Tyr Ile Leu Lys Leu Asp
    275                 280                 285

Arg Asn Pro Asp Phe Thr Ala Ser Ser Gln Ile Ala Phe Gly Arg Ala
    290                 295                 300
```

```
Ala His Arg Met Lys Gln Gln Gly Gln Ser Gly Ala Phe Thr Val Leu
305                 310                 315                 320

Glu Val Ala Pro Tyr Leu Leu Ser Pro Glu Asn Leu Asp Asp Leu Ile
            325                 330                 335

Ala Arg Asp Val
            340

<210> SEQ ID NO 11
<211> LENGTH: 1338
<212> TYPE: DNA
<213> ORGANISM: Corynebacterium glutamicum
<220> FEATURE:
<221> NAME/KEY: CDS
<222> LOCATION: (1)..(1338)

<400> SEQUENCE: 11 atg gct aca gtt gaa aat ttc aat gaa ctt ccc gca cac gta tgg cca      48
Met Ala Thr Val Glu Asn Phe Asn Glu Leu Pro Ala His Val Trp Pro
1               5                   10                  15 cgc aat gca gtg cgc caa gaa gac ggc gtt gtc acc gtc gct ggt gtg      96
Arg Asn Ala Val Arg Gln Glu Asp Gly Val Val Thr Val Ala Gly Val
                20                  25                  30 cct ctg cct gac ctc gct gaa gaa tac gga acc cca ctg ttc gta gtc     144
Pro Leu Pro Asp Leu Ala Glu Glu Tyr Gly Thr Pro Leu Phe Val Val
            35                  40                  45 gac gag gac gat ttc cgt tcc cgc tgt cgc gac atg gct acc gca ttc     192
Asp Glu Asp Asp Phe Arg Ser Arg Cys Arg Asp Met Ala Thr Ala Phe
        50                  55                  60 ggt gga cca ggc aat gtg cac tac gca tcc aaa gcg ttc ctg acc aag     240
Gly Gly Pro Gly Asn Val His Tyr Ala Ser Lys Ala Phe Leu Thr Lys
65                  70                  75                  80 acc att gca cgt tgg gtt gat gaa gag ggg ctg gca ctg gac att gcg     288
Thr Ile Ala Arg Trp Val Asp Glu Glu Gly Leu Ala Leu Asp Ile Ala
                85                  90                  95 tcc atc aat gaa ctg ggc att gcc ctg gcc gct ggt ttc ccg gcc agc     336
Ser Ile Asn Glu Leu Gly Ile Ala Leu Ala Ala Gly Phe Pro Ala Ser
            100                 105                 110 cgt atc acc gcg cac ggc aac aac aaa ggc gta gag ttc ctg cgc gcg     384
Arg Ile Thr Ala His Gly Asn Asn Lys Gly Val Glu Phe Leu Arg Ala
        115                 120                 125 ttg gtt caa aac ggt gtc ggg cat gtg gtg ctg gac tcc gcg cag gaa     432
Leu Val Gln Asn Gly Val Gly His Val Val Leu Asp Ser Ala Gln Glu
    130                 135                 140 ttg gaa ctg ctg gat tac gtt gcc gct ggt gaa ggc aag atc cag gac     480
Leu Glu Leu Leu Asp Tyr Val Ala Ala Gly Glu Gly Lys Ile Gln Asp
145                 150                 155                 160 gtg ttg atc cgc gtg aag cca ggt atc gaa gcc cac acc cac gag ttc     528
Val Leu Ile Arg Val Lys Pro Gly Ile Glu Ala His Thr His Glu Phe
                165                 170                 175 atc gcc act agc cac gaa gac cag aag ttc gga ttc tcc ctg gca tcc     576
Ile Ala Thr Ser His Glu Asp Gln Lys Phe Gly Phe Ser Leu Ala Ser
            180                 185                 190 ggt tcc gca ttc gaa gca gcg aaa gca gcc aac aat gca gag aac ttg     624
Gly Ser Ala Phe Glu Ala Ala Lys Ala Ala Asn Asn Ala Glu Asn Leu
        195                 200                 205 aac ctg gtt ggt ctg cac tgc cat gtt ggt tcc cag gtg ttc gac gcc     672
Asn Leu Val Gly Leu His Cys His Val Gly Ser Gln Val Phe Asp Ala
    210                 215                 220 gaa ggc ttc aag ctg gca gca gag cgc gtg ttg ggc ctg tac tca cag     720
Glu Gly Phe Lys Leu Ala Ala Glu Arg Val Leu Gly Leu Tyr Ser Gln
```

-continued

```
                      225                 230                 235                 240
atc cac agc gaa cta ggt gtc gcc ctt cct gag ctg gac ctc ggt ggc          768
Ile His Ser Glu Leu Gly Val Ala Leu Pro Glu Leu Asp Leu Gly Gly
                245                 250                 255 gga tac ggc atc gcc tac act gca gat gag gaa cca ctc aac gtc gca          816
Gly Tyr Gly Ile Ala Tyr Thr Ala Asp Glu Glu Pro Leu Asn Val Ala
            260                 265                 270 gaa gtc gcc tcc gac cta ctc acc gca gtc gga aaa atg gca gcg gaa          864
Glu Val Ala Ser Asp Leu Leu Thr Ala Val Gly Lys Met Ala Ala Glu
        275                 280                 285 cta ggc atc gac gca cca acc gtg ctt gtt gag ccc ggc cgc gct atc          912
Leu Gly Ile Asp Ala Pro Thr Val Leu Val Glu Pro Gly Arg Ala Ile
    290                 295                 300 gca ggc ccc tcc acc gtg acc atc tac gaa gtc ggc acc acc aaa aac          960
Ala Gly Pro Ser Thr Val Thr Ile Tyr Glu Val Gly Thr Thr Lys Asn
305                 310                 315                 320 gtc cac gta gac gac gac aaa acc cgc cgc tac gta gcc gtc gac gga         1008
Val His Val Asp Asp Asp Lys Thr Arg Arg Tyr Val Ala Val Asp Gly
                325                 330                 335 ggc atg tcc gac aac atc cgc cca gca ctc tac ggc tcc gaa tac gac         1056
Gly Met Ser Asp Asn Ile Arg Pro Ala Leu Tyr Gly Ser Glu Tyr Asp
            340                 345                 350 gcc cgc gta gta tcc cgc ttc gcc gaa gga gac cca gta agc acc cgc         1104
Ala Arg Val Val Ser Arg Phe Ala Glu Gly Asp Pro Val Ser Thr Arg
        355                 360                 365 atc gtg ggc tcc cac tgc gaa tcc ggc gat atc ctg atc aac gat gaa         1152
Ile Val Gly Ser His Cys Glu Ser Gly Asp Ile Leu Ile Asn Asp Glu
    370                 375                 380 atc tac cca tct gac atc acc agc ggc gac ttc ctc gca ctc gca gcc         1200
Ile Tyr Pro Ser Asp Ile Thr Ser Gly Asp Phe Leu Ala Leu Ala Ala
385                 390                 395                 400 acc ggc gca tac tgc tac gcc atg agc tcc cgc tac aac gcc ttc aca         1248
Thr Gly Ala Tyr Cys Tyr Ala Met Ser Ser Arg Tyr Asn Ala Phe Thr
                405                 410                 415 cgg ccc gcc gtc gtg tcc gtc cgc gct ggc agc tcc cgc ctc atg ctg         1296
Arg Pro Ala Val Val Ser Val Arg Ala Gly Ser Ser Arg Leu Met Leu
            420                 425                 430 cgc cgc gaa acc ctc gac gac atc ctc tca cta gag gca taa                 1338
Arg Arg Glu Thr Leu Asp Asp Ile Leu Ser Leu Glu Ala
        435                 440                 445
```

<210> SEQ ID NO 12
<211> LENGTH: 445
<212> TYPE: PRT
<213> ORGANISM: Corynebacterium glutamicum

<400> SEQUENCE: 12

```
Met Ala Thr Val Glu Asn Phe Asn Glu Leu Pro Ala His Val Trp Pro
1               5                   10                  15

Arg Asn Ala Val Arg Gln Glu Asp Gly Val Val Thr Val Ala Gly Val
                20                  25                  30

Pro Leu Pro Asp Leu Ala Glu Glu Tyr Gly Thr Pro Leu Phe Val Val
            35                  40                  45

Asp Glu Asp Asp Phe Arg Ser Arg Cys Arg Asp Met Ala Thr Ala Phe
        50                  55                  60

Gly Gly Pro Gly Asn Val His Tyr Ala Ser Lys Ala Phe Leu Thr Lys
65                  70                  75                  80

Thr Ile Ala Arg Trp Val Asp Glu Glu Gly Leu Ala Leu Asp Ile Ala
                85                  90                  95
```

```
Ser Ile Asn Glu Leu Gly Ile Ala Leu Ala Ala Gly Phe Pro Ala Ser
            100                 105                 110

Arg Ile Thr Ala His Gly Asn Asn Lys Gly Val Glu Phe Leu Arg Ala
        115                 120                 125

Leu Val Gln Asn Gly Val Gly His Val Leu Asp Ser Ala Gln Glu
    130                 135                 140

Leu Glu Leu Leu Asp Tyr Val Ala Ala Gly Gly Lys Ile Gln Asp
145                 150                 155                 160

Val Leu Ile Arg Val Lys Pro Gly Ile Glu Ala His Thr His Glu Phe
                165                 170                 175

Ile Ala Thr Ser His Glu Asp Gln Lys Phe Gly Phe Ser Leu Ala Ser
            180                 185                 190

Gly Ser Ala Phe Glu Ala Ala Lys Ala Ala Asn Asn Ala Glu Asn Leu
        195                 200                 205

Asn Leu Val Gly Leu His Cys His Val Gly Ser Gln Val Phe Asp Ala
    210                 215                 220

Glu Gly Phe Lys Leu Ala Ala Glu Arg Val Leu Gly Leu Tyr Ser Gln
225                 230                 235                 240

Ile His Ser Glu Leu Gly Val Ala Leu Pro Glu Leu Asp Leu Gly Gly
                245                 250                 255

Gly Tyr Gly Ile Ala Tyr Thr Ala Asp Glu Pro Leu Asn Val Ala
            260                 265                 270

Glu Val Ala Ser Asp Leu Leu Thr Ala Val Gly Lys Met Ala Ala Glu
        275                 280                 285

Leu Gly Ile Asp Ala Pro Thr Val Leu Val Glu Pro Gly Arg Ala Ile
    290                 295                 300

Ala Gly Pro Ser Thr Val Thr Ile Tyr Glu Val Gly Thr Thr Lys Asn
305                 310                 315                 320

Val His Val Asp Asp Lys Thr Arg Arg Tyr Val Ala Val Asp Gly
                325                 330                 335

Gly Met Ser Asp Asn Ile Arg Pro Ala Leu Tyr Gly Ser Glu Tyr Asp
            340                 345                 350

Ala Arg Val Val Ser Arg Phe Ala Glu Gly Asp Pro Val Ser Thr Arg
        355                 360                 365

Ile Val Gly Ser His Cys Glu Ser Gly Asp Ile Leu Ile Asn Asp Glu
    370                 375                 380

Ile Tyr Pro Ser Asp Ile Thr Ser Gly Asp Phe Leu Ala Leu Ala Ala
385                 390                 395                 400

Thr Gly Ala Tyr Cys Tyr Ala Met Ser Ser Arg Tyr Asn Ala Phe Thr
                405                 410                 415

Arg Pro Ala Val Val Ser Val Arg Ala Gly Ser Ser Arg Leu Met Leu
            420                 425                 430

Arg Arg Glu Thr Leu Asp Asp Ile Leu Ser Leu Glu Ala
        435                 440                 445

<210> SEQ ID NO 13
<211> LENGTH: 1338
<212> TYPE: DNA
<213> ORGANISM: Corynebacterium glutamicum
<220> FEATURE:
<221> NAME/KEY: CDS
<222> LOCATION: (1)..(1338)

<400> SEQUENCE: 13 atg gct aca gtt gaa aat ttc aat gaa ctt ccc gca cac gta tgg cca       48
```

```
Met Ala Thr Val Glu Asn Phe Asn Glu Leu Pro Ala His Val Trp Pro
1               5                  10                 15 cgc aat gcc gtg cgc caa gaa gac ggc gtt gtc acc gtc gct ggt gtg    96
Arg Asn Ala Val Arg Gln Glu Asp Gly Val Val Thr Val Ala Gly Val
                20                  25                 30 cct ctg cct gac ctc gct gaa gaa tac gga acc cca ctg ttc gta gtc    144
Pro Leu Pro Asp Leu Ala Glu Glu Tyr Gly Thr Pro Leu Phe Val Val
            35                  40                  45 gac gag gac gat ttc cgt tcc cgc tgt cgc gac atg gct acc gca ttc    192
Asp Glu Asp Asp Phe Arg Ser Arg Cys Arg Asp Met Ala Thr Ala Phe
50                  55                  60 ggt gga cca ggc aat gtg cac tac gca tct aaa gcg ttc ctg acc aag    240
Gly Gly Pro Gly Asn Val His Tyr Ala Ser Lys Ala Phe Leu Thr Lys
65                  70                  75                  80 acc att gca cgt tgg gtt gat gaa gag ggg ctg gca ctg gac att gca    288
Thr Ile Ala Arg Trp Val Asp Glu Glu Gly Leu Ala Leu Asp Ile Ala
                85                  90                  95 tcc atc aac gaa ctg ggc att gcc ctg gcc gct ggt ttc ccc gcc agc    336
Ser Ile Asn Glu Leu Gly Ile Ala Leu Ala Ala Gly Phe Pro Ala Ser
            100                 105                 110 cgt atc acc gcg cac ggc aac aac aaa ggc gta gag ttc ctg cgc gcg    384
Arg Ile Thr Ala His Gly Asn Asn Lys Gly Val Glu Phe Leu Arg Ala
        115                 120                 125 ttg gtt caa aac ggt gtg gga cac gtg gtg ctg gac tcc gca cag gaa    432
Leu Val Gln Asn Gly Val Gly His Val Val Leu Asp Ser Ala Gln Glu
130                 135                 140 cta gaa ctg ttg gat tac gtt gcc gct ggt gaa ggc aag att cag gac    480
Leu Glu Leu Leu Asp Tyr Val Ala Ala Gly Glu Gly Lys Ile Gln Asp
145                 150                 155                 160 gtg ttg atc cgc gta aag cca ggc atc gaa gca cac acc cac gag ttc    528
Val Leu Ile Arg Val Lys Pro Gly Ile Glu Ala His Thr His Glu Phe
                165                 170                 175 atc gcc act agc cac gaa gac cag aag ttc gga ttc tcc ctg gca tcc    576
Ile Ala Thr Ser His Glu Asp Gln Lys Phe Gly Phe Ser Leu Ala Ser
            180                 185                 190 ggt tcc gca ttc gaa gca gca aaa gcc gcc aac aac gca gaa aac ctg    624
Gly Ser Ala Phe Glu Ala Ala Lys Ala Ala Asn Asn Ala Glu Asn Leu
        195                 200                 205 aac ctg gtt ggc ctg cac tgc cac gtt ggt tcc cag gtg ttc gac gcc    672
Asn Leu Val Gly Leu His Cys His Val Gly Ser Gln Val Phe Asp Ala
210                 215                 220 gaa ggc ttc aag ctg gca gca gaa cgc gtg ttg ggc ctg tac tca cag    720
Glu Gly Phe Lys Leu Ala Ala Glu Arg Val Leu Gly Leu Tyr Ser Gln
225                 230                 235                 240 atc cac agc gaa ctg ggc gtt gcc ctt cct gaa ctg gat ctc ggt ggc    768
Ile His Ser Glu Leu Gly Val Ala Leu Pro Glu Leu Asp Leu Gly Gly
                245                 250                 255 gga tac ggc att gcc tat acc gca gct gaa gaa cca ctc aac gtc gca    816
Gly Tyr Gly Ile Ala Tyr Thr Ala Ala Glu Glu Pro Leu Asn Val Ala
            260                 265                 270 gaa gtt gcc tcc gac ctg ctc acc gca gtc gga aaa atg gca gcg gaa    864
Glu Val Ala Ser Asp Leu Leu Thr Ala Val Gly Lys Met Ala Ala Glu
        275                 280                 285 cta ggc atc gac gca cca acc gtg ctt gtt gag ccc ggc cgc gct atc    912
Leu Gly Ile Asp Ala Pro Thr Val Leu Val Glu Pro Gly Arg Ala Ile
290                 295                 300 gca ggc ccc tcc acc gtg acc atc tac gaa gtc ggc acc acc aaa gac    960
Ala Gly Pro Ser Thr Val Thr Ile Tyr Glu Val Gly Thr Thr Lys Asp
305                 310                 315                 320
```

```
gtc cac gta gac gac gac aaa acc cgc cgt tac atc gcc gtg gac gga    1008
Val His Val Asp Asp Asp Lys Thr Arg Arg Tyr Ile Ala Val Asp Gly
                325                 330                 335 ggc atg tcc gac aac atc cgc cca gca ctc tac ggc tcc gaa tac gac    1056
Gly Met Ser Asp Asn Ile Arg Pro Ala Leu Tyr Gly Ser Glu Tyr Asp
            340                 345                 350 gcc cgc gta gta tcc cgc ttc gcc gaa gga gac cca gta agc acc cgc    1104
Ala Arg Val Val Ser Arg Phe Ala Glu Gly Asp Pro Val Ser Thr Arg
        355                 360                 365 atc gtg ggc tcc cac tgc gaa tcc ggc gat atc ctg atc aac gat gaa    1152
Ile Val Gly Ser His Cys Glu Ser Gly Asp Ile Leu Ile Asn Asp Glu
    370                 375                 380 atc tac cca tct gac atc acc agc ggc gac ttc ctt gca ctc gca gcc    1200
Ile Tyr Pro Ser Asp Ile Thr Ser Gly Asp Phe Leu Ala Leu Ala Ala
385                 390                 395                 400 acc ggc gca tac tgc tac gcc atg agc tcc cgc tac aac gcc ttc aca    1248
Thr Gly Ala Tyr Cys Tyr Ala Met Ser Ser Arg Tyr Asn Ala Phe Thr
                405                 410                 415 cgg ccc gcc gtc gtg tcc gtc cgc gct ggc agc tcc cgc ctc atg ctg    1296
Arg Pro Ala Val Val Ser Val Arg Ala Gly Ser Ser Arg Leu Met Leu
            420                 425                 430 cgc cgc gaa acg ctc gac gac atc ctc tca cta gag gca taa            1338
Arg Arg Glu Thr Leu Asp Asp Ile Leu Ser Leu Glu Ala
        435                 440                 445

<210> SEQ ID NO 14
<211> LENGTH: 445
<212> TYPE: PRT
<213> ORGANISM: Corynebacterium glutamicum

<400> SEQUENCE: 14

Met Ala Thr Val Glu Asn Phe Asn Glu Leu Pro Ala His Val Trp Pro
1               5                   10                  15

Arg Asn Ala Val Arg Gln Glu Asp Gly Val Val Thr Val Ala Gly Val
                20                  25                  30

Pro Leu Pro Asp Leu Ala Glu Glu Tyr Gly Thr Pro Leu Phe Val Val
            35                  40                  45

Asp Glu Asp Asp Phe Arg Ser Arg Cys Arg Asp Met Ala Thr Ala Phe
        50                  55                  60

Gly Gly Pro Gly Asn Val His Tyr Ala Ser Lys Ala Phe Leu Thr Lys
65                  70                  75                  80

Thr Ile Ala Arg Trp Val Asp Glu Glu Gly Leu Ala Leu Asp Ile Ala
                85                  90                  95

Ser Ile Asn Glu Leu Gly Ile Ala Leu Ala Ala Gly Phe Pro Ala Ser
            100                 105                 110

Arg Ile Thr Ala His Gly Asn Asn Lys Gly Val Glu Phe Leu Arg Ala
        115                 120                 125

Leu Val Gln Asn Gly Val Gly His Val Val Leu Asp Ser Ala Gln Glu
    130                 135                 140

Leu Glu Leu Leu Asp Tyr Val Ala Ala Gly Glu Gly Lys Ile Gln Asp
145                 150                 155                 160

Val Leu Ile Arg Val Lys Pro Gly Ile Glu Ala His Thr His Glu Phe
                165                 170                 175

Ile Ala Thr Ser His Glu Asp Gln Lys Phe Gly Phe Ser Leu Ala Ser
            180                 185                 190

Gly Ser Ala Phe Glu Ala Ala Lys Ala Ala Asn Asn Ala Glu Asn Leu
        195                 200                 205
```

-continued

```
Asn Leu Val Gly Leu His Cys His Val Gly Ser Gln Val Phe Asp Ala
    210                 215                 220
Glu Gly Phe Lys Leu Ala Ala Glu Arg Val Leu Gly Leu Tyr Ser Gln
225                 230                 235                 240
Ile His Ser Glu Leu Gly Val Ala Leu Pro Glu Leu Asp Leu Gly Gly
                245                 250                 255
Gly Tyr Gly Ile Ala Tyr Thr Ala Ala Glu Pro Leu Asn Val Ala
            260                 265                 270
Glu Val Ala Ser Asp Leu Leu Thr Ala Val Gly Lys Met Ala Ala Glu
        275                 280                 285
Leu Gly Ile Asp Ala Pro Thr Val Leu Val Glu Pro Gly Arg Ala Ile
    290                 295                 300
Ala Gly Pro Ser Thr Val Thr Ile Tyr Glu Val Gly Thr Thr Lys Asp
305                 310                 315                 320
Val His Val Asp Asp Lys Thr Arg Arg Tyr Ile Ala Val Asp Gly
                325                 330                 335
Gly Met Ser Asp Asn Ile Arg Pro Ala Leu Tyr Gly Ser Glu Tyr Asp
            340                 345                 350
Ala Arg Val Val Ser Arg Phe Ala Glu Gly Asp Pro Val Ser Thr Arg
        355                 360                 365
Ile Val Gly Ser His Cys Glu Ser Gly Asp Ile Leu Ile Asn Asp Glu
    370                 375                 380
Ile Tyr Pro Ser Asp Ile Thr Ser Gly Asp Phe Leu Ala Leu Ala Ala
385                 390                 395                 400
Thr Gly Ala Tyr Cys Tyr Ala Met Ser Ser Arg Tyr Asn Ala Phe Thr
                405                 410                 415
Arg Pro Ala Val Val Ser Val Arg Ala Gly Ser Ser Arg Leu Met Leu
            420                 425                 430
Arg Arg Glu Thr Leu Asp Asp Ile Leu Ser Leu Glu Ala
        435                 440                 445
```

<210> SEQ ID NO 15
<211> LENGTH: 753
<212> TYPE: DNA
<213> ORGANISM: Corynebacterium glutamicum
<220> FEATURE:
<221> NAME/KEY: CDS
<222> LOCATION: (1)..(753)

<400> SEQUENCE: 15

```
gtg gcc gaa caa gtt aaa ttg agc gtg gag ttg ata gcg tgc agt tct    48
Met Ala Glu Gln Val Lys Leu Ser Val Glu Leu Ile Ala Cys Ser Ser
1               5                   10                  15 ttt act cca ccc gct gat gtt gag tgg tca act gat gtt gag ggc gcg    96
Phe Thr Pro Pro Ala Asp Val Glu Trp Ser Thr Asp Val Glu Gly Ala
            20                  25                  30 gaa gca ctc gtc gag ttt gcg ggt cgt gcc tgc tac gaa act ttt gat   144
Glu Ala Leu Val Glu Phe Ala Gly Arg Ala Cys Tyr Glu Thr Phe Asp
        35                  40                  45 aag ccg aac cct cga act gct tcc aat gct gcg tat ctg cgc cac atc   192
Lys Pro Asn Pro Arg Thr Ala Ser Asn Ala Ala Tyr Leu Arg His Ile
    50                  55                  60 atg gaa gtg ggg cac act gct ttg ctt gag cat gcc aat gcc acg atg   240
Met Glu Val Gly His Thr Ala Leu Leu Glu His Ala Asn Ala Thr Met
65                  70                  75                  80 tat atc cga ggc att tct cgg tcc gcg acc cat gaa ttg gtc cga cac   288
Tyr Ile Arg Gly Ile Ser Arg Ser Ala Thr His Glu Leu Val Arg His
                85                  90                  95
```

```
cgc cat ttt tcc ttc tct caa ctg tct cag cgt ttc gtg cac agc gga         336
Arg His Phe Ser Phe Ser Gln Leu Ser Gln Arg Phe Val His Ser Gly
            100                 105                 110 gaa tcg gaa gta gtg gtg ccc act ctc atc gat gaa gat ccg cag ttg         384
Glu Ser Glu Val Val Val Pro Thr Leu Ile Asp Glu Asp Pro Gln Leu
        115                 120                 125 cgt gaa ctt ttc atg cac gcc atg gat gag tct cgg ttc gct ttc aat         432
Arg Glu Leu Phe Met His Ala Met Asp Glu Ser Arg Phe Ala Phe Asn
    130                 135                 140 gag ctg ctt aat gcg ctg gaa gaa aaa ctt ggc gat gaa ccg aat gca         480
Glu Leu Leu Asn Ala Leu Glu Glu Lys Leu Gly Asp Glu Pro Asn Ala
145                 150                 155                 160 ctt tta agg aaa aag cag gct cgt caa gca gct cgc gct gtg ctg ccc         528
Leu Leu Arg Lys Lys Gln Ala Arg Gln Ala Ala Arg Ala Val Leu Pro
                165                 170                 175 aac gct aca gag tcc aga atc gtg gtg tct gga aac ttc cgc acc tgg         576
Asn Ala Thr Glu Ser Arg Ile Val Val Ser Gly Asn Phe Arg Thr Trp
            180                 185                 190 agg cat ttc att ggc atg cga gcc agt gaa cat gca gac gtc gaa atc         624
Arg His Phe Ile Gly Met Arg Ala Ser Glu His Ala Asp Val Glu Ile
        195                 200                 205 cgc gaa gta gcg gta gga tgt tta aga aag ctg cag gta gca gcg cca         672
Arg Glu Val Ala Val Gly Cys Leu Arg Lys Leu Gln Val Ala Ala Pro
    210                 215                 220 act gtt ttc ggt gat ttt gag att gaa act ttg gca gac gga tcg caa         720
Thr Val Phe Gly Asp Phe Glu Ile Glu Thr Leu Ala Asp Gly Ser Gln
225                 230                 235                 240 atg gca aca agc ccg tat gtc atg gac ttt taa                             753
Met Ala Thr Ser Pro Tyr Val Met Asp Phe
                245                 250

<210> SEQ ID NO 16
<211> LENGTH: 250
<212> TYPE: PRT
<213> ORGANISM: Corynebacterium glutamicum

<400> SEQUENCE: 16

Met Ala Glu Gln Val Lys Leu Ser Val Glu Leu Ile Ala Cys Ser Ser
1               5                   10                  15

Phe Thr Pro Pro Ala Asp Val Glu Trp Ser Thr Asp Val Glu Gly Ala
            20                  25                  30

Glu Ala Leu Val Glu Phe Ala Gly Arg Ala Cys Tyr Glu Thr Phe Asp
        35                  40                  45

Lys Pro Asn Pro Arg Thr Ala Ser Asn Ala Ala Tyr Leu Arg His Ile
    50                  55                  60

Met Glu Val Gly His Thr Ala Leu Leu Glu His Ala Asn Ala Thr Met
65                  70                  75                  80

Tyr Ile Arg Gly Ile Ser Arg Ser Ala Thr His Glu Leu Val Arg His
                85                  90                  95

Arg His Phe Ser Phe Ser Gln Leu Ser Gln Arg Phe Val His Ser Gly
            100                 105                 110

Glu Ser Glu Val Val Val Pro Thr Leu Ile Asp Glu Asp Pro Gln Leu
        115                 120                 125

Arg Glu Leu Phe Met His Ala Met Asp Glu Ser Arg Phe Ala Phe Asn
    130                 135                 140

Glu Leu Leu Asn Ala Leu Glu Glu Lys Leu Gly Asp Glu Pro Asn Ala
145                 150                 155                 160
```

-continued

```
Leu Leu Arg Lys Lys Gln Ala Arg Gln Ala Ala Arg Ala Val Leu Pro
            165                 170                 175

Asn Ala Thr Glu Ser Arg Ile Val Val Ser Gly Asn Phe Arg Thr Trp
        180                 185                 190

Arg His Phe Ile Gly Met Arg Ala Ser Glu His Ala Asp Val Glu Ile
        195                 200                 205

Arg Glu Val Ala Val Gly Cys Leu Arg Lys Leu Gln Val Ala Ala Pro
    210                 215                 220

Thr Val Phe Gly Asp Phe Glu Ile Glu Thr Leu Ala Asp Gly Ser Gln
225                 230                 235                 240

Met Ala Thr Ser Pro Tyr Val Met Asp Phe
            245                 250

<210> SEQ ID NO 17
<211> LENGTH: 551
<212> TYPE: DNA
<213> ORGANISM: Corynebacterium glutamicum

<400> SEQUENCE: 17
aaccggtgtg gagccgacca ttccgcgagg ctgcactgca acgaggtcgt agttttggta      60
catggcttct ggccagttca tggattggct gccgaagaag ctataggcat cgccaccagg     120
gccaccggag ttaccgaaga tggtgccgtg cttttcgcct tgggcaggga ccttgacaaa     180
gcccacgctg atatcgccaa gtgagggatc agaatagtgc atgggcacgt cgatgctgcc     240
acattgagcg gaggcaatat ctacctgagg tgggcattct tcccagcgga tgttttcttg     300
cgctgctgca gtgggcattg ataccaaaaa ggggctaagc gcagtcgagg cggcaagaac     360
tgctactacc ttttttattg tcgaacgggg cattacggct ccaaggacgt ttgttttctg     420
ggtcagttac cccaaaaagc atatacagag accaatgatt tttcattaaa aaggcaggga     480
tttgttataa gtatgggtcg tattctgtgc gacgggtgta cctcggctag aatttctccc     540
catgacacca g                                                          551

<210> SEQ ID NO 18
<211> LENGTH: 365
<212> TYPE: DNA
<213> ORGANISM: Corynebacterium glutamicum
<220> FEATURE:
<221> NAME/KEY: CDS
<222> LOCATION: (1)..(365)

<400> SEQUENCE: 18 gtg gcc gaa caa gtt aaa ttg agc gtg gag ttg ata gcg tgc agt tct       48
Met Ala Glu Gln Val Lys Leu Ser Val Glu Leu Ile Ala Cys Ser Ser
1               5                  10                  15 ttt act cca ccc gct gat gtt gag tgg tca act gat gtt gag ggc gcg       96
Phe Thr Pro Pro Ala Asp Val Glu Trp Ser Thr Asp Val Glu Gly Ala
            20                  25                  30 gaa gca ctc gtc gag ttt gcg ggt cgt gcc tgc tac gaa act ttt gat      144
Glu Ala Leu Val Glu Phe Ala Gly Arg Ala Cys Tyr Glu Thr Phe Asp
        35                  40                  45 aag ccg aac cct cga act gct tcc aat gct gcg tat ctg cgc cac atc      192
Lys Pro Asn Pro Arg Thr Ala Ser Asn Ala Ala Tyr Leu Arg His Ile
    50                  55                  60 atg gaa gtg ggg cac act gct ttg ctt gag cat gcc aat gcc acg atg      240
Met Glu Val Gly His Thr Ala Leu Leu Glu His Ala Asn Ala Thr Met
65                  70                  75                  80 tat atc cga ggc att tct cgg tcc gcg acc cat gaa ttg gtc cga cac      288
Tyr Ile Arg Gly Ile Ser Arg Ser Ala Thr His Glu Leu Val Arg His
```

```
                  85                  90                  95
cgc cat ttt tcc ttc tct caa ctg tct cag cgt ttc gtg cac agc gga    336
Arg His Phe Ser Phe Ser Gln Leu Ser Gln Arg Phe Val His Ser Gly
            100                 105                 110 gaa tcg gaa gta gtg gtg ccc act ctc at                             365
Glu Ser Glu Val Val Val Pro Thr Leu Ile
        115                 120

<210> SEQ ID NO 19
<211> LENGTH: 122
<212> TYPE: PRT
<213> ORGANISM: Corynebacterium glutamicum

<400> SEQUENCE: 19

Met Ala Glu Gln Val Lys Leu Ser Val Glu Leu Ile Ala Cys Ser Ser
1               5                   10                  15

Phe Thr Pro Pro Ala Asp Val Glu Trp Ser Thr Asp Val Glu Gly Ala
            20                  25                  30

Glu Ala Leu Val Glu Phe Ala Gly Arg Ala Cys Tyr Glu Thr Phe Asp
        35                  40                  45

Lys Pro Asn Pro Arg Thr Ala Ser Asn Ala Ala Tyr Leu Arg His Ile
    50                  55                  60

Met Glu Val Gly His Thr Ala Leu Leu Glu His Ala Asn Ala Thr Met
65                  70                  75                  80

Tyr Ile Arg Gly Ile Ser Arg Ser Ala Thr His Glu Leu Val Arg His
                85                  90                  95

Arg His Phe Ser Phe Ser Gln Leu Ser Gln Arg Phe Val His Ser Gly
            100                 105                 110

Glu Ser Glu Val Val Val Pro Thr Leu Ile
        115                 120

<210> SEQ ID NO 20
<211> LENGTH: 833
<212> TYPE: DNA
<213> ORGANISM: Corynebacterium glutamicum
<220> FEATURE:
<221> NAME/KEY: CDS
<222> LOCATION: (1)..(833)

<400> SEQUENCE: 20 atg gct aca gtt gaa aat ttc aat gaa ctt ccc gca cac gta tgg cca    48
Met Ala Thr Val Glu Asn Phe Asn Glu Leu Pro Ala His Val Trp Pro
1               5                   10                  15 cgc aat gca gtg cgc caa gaa gac ggc gtt gtc acc gtc gct ggt gtg    96
Arg Asn Ala Val Arg Gln Glu Asp Gly Val Val Thr Val Ala Gly Val
            20                  25                  30 cct ctg cct gac ctc gct gaa gaa tac gga acc cca ctg ttc gta gtc    144
Pro Leu Pro Asp Leu Ala Glu Glu Tyr Gly Thr Pro Leu Phe Val Val
        35                  40                  45 gac gag gac gat ttc cgt tcc cgc tgt cgc gac atg gct acc gca ttc    192
Asp Glu Asp Asp Phe Arg Ser Arg Cys Arg Asp Met Ala Thr Ala Phe
    50                  55                  60 ggt gga cca ggc aat gtg cac tac gca tcc aaa gcg ttc ctg acc aag    240
Gly Gly Pro Gly Asn Val His Tyr Ala Ser Lys Ala Phe Leu Thr Lys
65                  70                  75                  80 acc att gca cgt tgg gtt gat gaa gag ggg ctg gca ctg gac att gcg    288
Thr Ile Ala Arg Trp Val Asp Glu Glu Gly Leu Ala Leu Asp Ile Ala
                85                  90                  95 tcc atc aat gaa ctg ggc att gcc ctg gcc gct ggt ttc ccg gcc agc    336
Ser Ile Asn Glu Leu Gly Ile Ala Leu Ala Ala Gly Phe Pro Ala Ser
```

```
cgt atc acc gcg cac ggc aac aac aaa ggc gta gag ttc ctg cgc gcg       384
Arg Ile Thr Ala His Gly Asn Asn Lys Gly Val Glu Phe Leu Arg Ala
            115                 120                 125 ttg gtt caa aac ggt gtc ggg cat gtg gtg ctg gac tcc gcg cag gaa       432
Leu Val Gln Asn Gly Val Gly His Val Val Leu Asp Ser Ala Gln Glu
    130                 135                 140 ttg gaa ctg ctg gat tac gtt gcc gct ggt gaa ggc aag atc cag gac       480
Leu Glu Leu Leu Asp Tyr Val Ala Ala Gly Glu Gly Lys Ile Gln Asp
145                 150                 155                 160 gtg ttg atc cgc gtg aag cca ggt atc gaa gcc cac acc cac gag ttc       528
Val Leu Ile Arg Val Lys Pro Gly Ile Glu Ala His Thr His Glu Phe
                165                 170                 175 atc gcc act agc cac gaa gac cag aag ttc gga ttc tcc ctg gca tcc       576
Ile Ala Thr Ser His Glu Asp Gln Lys Phe Gly Phe Ser Leu Ala Ser
            180                 185                 190 ggt tcc gca ttc gaa gca gcg aaa gca gcc aac aat gca gag aac ttg       624
Gly Ser Ala Phe Glu Ala Ala Lys Ala Ala Asn Asn Ala Glu Asn Leu
    195                 200                 205 aac ctg gtt ggt ctg cac tgc cat gtt ggt tcc cag gtg ttc gac gcc       672
Asn Leu Val Gly Leu His Cys His Val Gly Ser Gln Val Phe Asp Ala
210                 215                 220 gaa ggc ttc aag ctg gca gca gag cgc gtg ttg ggc ctg tac tca cag       720
Glu Gly Phe Lys Leu Ala Ala Glu Arg Val Leu Gly Leu Tyr Ser Gln
225                 230                 235                 240 atc cac agc gaa cta ggt gtc gcc ctt cct gag ctg gac ctc ggt ggc       768
Ile His Ser Glu Leu Gly Val Ala Leu Pro Glu Leu Asp Leu Gly Gly
                245                 250                 255 gga tac ggc atc gcc tac act gca gat gag gaa cca ctc aac gtc gca       816
Gly Tyr Gly Ile Ala Tyr Thr Ala Asp Glu Glu Pro Leu Asn Val Ala
            260                 265                 270 gaa gtc gcc tcc gac ct                                                833
Glu Val Ala Ser Asp Leu
            275
```

<210> SEQ ID NO 21
<211> LENGTH: 278
<212> TYPE: PRT
<213> ORGANISM: Corynebacterium glutamicum

<400> SEQUENCE: 21

```
Met Ala Thr Val Glu Asn Phe Asn Glu Leu Pro Ala His Val Trp Pro
1               5                   10                  15

Arg Asn Ala Val Arg Gln Glu Asp Gly Val Val Thr Val Ala Gly Val
                20                  25                  30

Pro Leu Pro Asp Leu Ala Glu Glu Tyr Gly Thr Pro Leu Phe Val Val
            35                  40                  45

Asp Glu Asp Asp Phe Arg Ser Arg Cys Arg Asp Met Ala Thr Ala Phe
        50                  55                  60

Gly Gly Pro Gly Asn Val His Tyr Ala Ser Lys Ala Phe Leu Thr Lys
65                  70                  75                  80

Thr Ile Ala Arg Trp Val Asp Glu Glu Gly Leu Ala Leu Asp Ile Ala
                85                  90                  95

Ser Ile Asn Glu Leu Gly Ile Ala Leu Ala Ala Gly Phe Pro Ala Ser
            100                 105                 110

Arg Ile Thr Ala His Gly Asn Asn Lys Gly Val Glu Phe Leu Arg Ala
        115                 120                 125

Leu Val Gln Asn Gly Val Gly His Val Val Leu Asp Ser Ala Gln Glu
```

```
                130                 135                 140
Leu Glu Leu Leu Asp Tyr Val Ala Ala Gly Gly Lys Ile Gln Asp
145                 150                 155                 160

Val Leu Ile Arg Val Lys Pro Gly Ile Glu Ala His Thr His Glu Phe
                165                 170                 175

Ile Ala Thr Ser His Glu Asp Gln Lys Phe Gly Phe Ser Leu Ala Ser
                180                 185                 190

Gly Ser Ala Phe Glu Ala Ala Lys Ala Ala Asn Asn Ala Glu Asn Leu
                195                 200                 205

Asn Leu Val Gly Leu His Cys His Val Gly Ser Gln Val Phe Asp Ala
210                 215                 220

Glu Gly Phe Lys Leu Ala Ala Glu Arg Val Leu Gly Leu Tyr Ser Gln
225                 230                 235                 240

Ile His Ser Glu Leu Gly Val Ala Leu Pro Glu Leu Asp Leu Gly Gly
                245                 250                 255

Gly Tyr Gly Ile Ala Tyr Thr Ala Asp Glu Glu Pro Leu Asn Val Ala
                260                 265                 270

Glu Val Ala Ser Asp Leu
        275

<210> SEQ ID NO 22
<211> LENGTH: 28
<212> TYPE: DNA
<213> ORGANISM: Artificial Sequence
<220> FEATURE:
<223> OTHER INFORMATION: Primer

<400> SEQUENCE: 22
gggtacctcg cgaagtagca cctgtcac                                    28

<210> SEQ ID NO 23
<211> LENGTH: 26
<212> TYPE: DNA
<213> ORGANISM: Artificial Sequence
<220> FEATURE:
<223> OTHER INFORMATION: Primer

<400> SEQUENCE: 23
gcggatcccc catcgcccct caaaga                                      26

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
aacgggcggt gaagggcaac t                                           21

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
tgaaagacag gggtatccag a                                           21

<210> SEQ ID NO 26
```

```
<211> LENGTH: 24
<212> TYPE: DNA
<213> ORGANISM: Artificial Sequence
<220> FEATURE:
<223> OTHER INFORMATION: Primer

<400> SEQUENCE: 26
ccatggtacc aagtgcgtgg cgag                                              24

<210> SEQ ID NO 27
<211> LENGTH: 25
<212> TYPE: DNA
<213> ORGANISM: Artificial Sequence
<220> FEATURE:
<223> OTHER INFORMATION: Primer

<400> SEQUENCE: 27
ccatggtacc acactgtttc cttgc                                             25

<210> SEQ ID NO 28
<211> LENGTH: 36
<212> TYPE: DNA
<213> ORGANISM: Artificial Sequence
<220> FEATURE:
<223> OTHER INFORMATION: Primer

<400> SEQUENCE: 28
ctggttccgg cgagtggagc cgaccattcc gcgagg                                 36

<210> SEQ ID NO 29
<211> LENGTH: 36
<212> TYPE: DNA
<213> ORGANISM: Artificial Sequence
<220> FEATURE:
<223> OTHER INFORMATION: Primer

<400> SEQUENCE: 29
ctcgctccgg cgaggtcgga ggcaacttct gcgacg                                 36

<210> SEQ ID NO 30
<211> LENGTH: 6
<212> TYPE: DNA
<213> ORGANISM: Artificial Sequence
<220> FEATURE:
<223> OTHER INFORMATION: Primer

<400> SEQUENCE: 30 ggtacc                                                                   6

<210> SEQ ID NO 31
<211> LENGTH: 18
<212> TYPE: DNA
<213> ORGANISM: Artificial Sequence
<220> FEATURE:
<223> OTHER INFORMATION: Primer

<400> SEQUENCE: 31
ggatcttcac ctagatcc                                                     18

<210> SEQ ID NO 32
<211> LENGTH: 16
<212> TYPE: DNA
<213> ORGANISM: Artificial Sequence
<220> FEATURE:
<223> OTHER INFORMATION: Primer

<400> SEQUENCE: 32
```

-continued

```
ccctgataaa tgcttc                                                    16

<210> SEQ ID NO 33
<211> LENGTH: 25
<212> TYPE: DNA
<213> ORGANISM: Artificial Sequence
<220> FEATURE:
<223> OTHER INFORMATION: Primer

<400> SEQUENCE: 33
ccggagaaga tgtaacaatg gctac                                          25

<210> SEQ ID NO 34
<211> LENGTH: 25
<212> TYPE: DNA
<213> ORGANISM: Artificial Sequence
<220> FEATURE:
<223> OTHER INFORMATION: Primer

<400> SEQUENCE: 34
cctcgactgc agacccctag acacc                                          25

<210> SEQ ID NO 35
<211> LENGTH: 421
<212> TYPE: PRT
<213> ORGANISM: Corynebacterium glutamicum

<400> SEQUENCE: 35
```

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

```
Ile Ala Gly Ser Met Glu Asp Ile Pro Val Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
        290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
                420

<210> SEQ ID NO 36
<211> LENGTH: 421
<212> TYPE: PRT
<213> ORGANISM: Corynebacterium glutamicum

<400> SEQUENCE: 36

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
                20                  25                  30

Gly Asn Asp Val Val Val Cys Ser Ala Met Gly Asp Thr Thr Asp
            35                  40                  45

Glu Leu Leu Glu Leu Ala Ala Ala Val Asn Pro Val Pro Pro Ala Arg
        50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
```

-continued

```
                180                 185                 190
Leu Glu Lys Leu Ser Phe Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
        290                 295                 300

Asp Gly Thr Thr Asp Ile Thr Phe Thr Cys Pro Arg Ala Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Asp Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 37
<211> LENGTH: 421
<212> TYPE: PRT
<213> ORGANISM: Corynebacterium glutamicum

<400> SEQUENCE: 37

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125
```

-continued

```
Lys Ile Cys Ile Val Ala Gly Phe Gln Gly Val Asn Lys Glu Thr Arg
    130                 135                 140
Asp Val Thr Thr Leu Gly Arg Gly Gly Ser Asp Thr Thr Ala Val Ala
145                 150                 155                 160
Leu Ala Ala Ala Leu Asn Ala Asp Val Cys Glu Ile Tyr Ser Asp Val
                165                 170                 175
Asp Gly Val Tyr Thr Ala Asp Pro Arg Ile Val Pro Asn Ala Gln Lys
                180                 185                 190
Leu Glu Lys Leu Ser Phe Glu Glu Met Leu Glu Leu Ala Ala Val Gly
            195                 200                 205
Ser Lys Ile Leu Val Leu Arg Ser Val Glu Tyr Ala Arg Ala Phe Asn
    210                 215                 220
Val Pro Leu Arg Val Arg Ser Ser Tyr Ser Asn Asp Pro Gly Thr Leu
225                 230                 235                 240
Ile Ala Gly Ser Met Glu Asp Ile Pro Val Glu Glu Ala Val Leu Thr
                245                 250                 255
Gly Val Ala Thr Asp Lys Ser Glu Ala Lys Val Thr Val Leu Gly Ile
                260                 265                 270
Ser Asp Lys Pro Gly Glu Ala Ala Lys Val Phe Arg Ala Leu Ala Asp
            275                 280                 285
Ala Glu Ile Asn Ile Asp Met Val Leu Gln Asn Val Ser Ser Val Glu
    290                 295                 300
Asp Gly Thr Thr Asp Ile Thr Phe Thr Cys Pro Arg Ala Asp Gly Arg
305                 310                 315                 320
Arg Ala Met Glu Ile Leu Lys Lys Leu Gln Val Gln Gly Asn Trp Thr
                325                 330                 335
Asn Val Leu Tyr Asp Asp Gln Val Gly Lys Val Ser Leu Val Gly Ala
                340                 345                 350
Gly Met Lys Ser His Pro Gly Val Thr Ala Glu Phe Met Glu Ala Leu
            355                 360                 365
Arg Asp Val Asn Val Asn Ile Glu Leu Ile Ser Thr Ser Glu Ile Arg
    370                 375                 380
Ile Ser Val Leu Ile Arg Glu Asp Asp Leu Asp Ala Ala Ala Arg Ala
385                 390                 395                 400
Leu His Glu Gln Phe Gln Leu Gly Gly Glu Asp Glu Ala Val Val Tyr
                405                 410                 415
Ala Gly Thr Gly Arg
                420
```